United States Patent
Jackson et al.

(10) Patent No.: US 11,266,337 B2
(45) Date of Patent: Mar. 8, 2022

(54) SYSTEMS, METHODS, AND DEVICES FOR SAMPLE COLLECTION, STABILIZATION AND PRESERVATION

(71) Applicant: Drawbridge Health, Inc., Menlo Park, CA (US)

(72) Inventors: Alicia Jackson, Menlo Park, CA (US); Rowan Chapman, Menlo Park, CA (US); Diana Maichin, San Francisco, CA (US); Harry Glorikian, Lexington, MA (US)

(73) Assignee: DRAWBRIDGE HEALTH, INC., Summerville, SC (US)

( * ) Notice: Subject to any disclaimer, the term of this patent is extended or adjusted under 35 U.S.C. 154(b) by 0 days.

(21) Appl. No.: 15/261,707

(22) Filed: Sep. 9, 2016

(65) Prior Publication Data

US 2017/0067803 A1   Mar. 9, 2017

Related U.S. Application Data

(60) Provisional application No. 62/216,312, filed on Sep. 9, 2015, provisional application No. 62/260,172, filed
(Continued)

(51) Int. Cl.
*C12Q 1/68* (2018.01)
*A61B 5/15* (2006.01)
*A61B 5/151* (2006.01)

(52) U.S. Cl.
CPC .. *A61B 5/150984* (2013.01); *A61B 5/150022* (2013.01); *A61B 5/150083* (2013.01);
(Continued)

(58) Field of Classification Search
CPC ....................................................... A61B 5/00
(Continued)

(56) References Cited

U.S. PATENT DOCUMENTS 2,849,334 A    8/1958  Hart
3,070,486 A   12/1962  Novak
(Continued)

FOREIGN PATENT DOCUMENTS

CN         1278649 C    10/2006
CN       101404935 A     4/2009
(Continued)

OTHER PUBLICATIONS

Nabatiyan et al. (Membrane-based plasma collection device for point-of-care diagnosis of HIV, J Virol Methods. Apr. 2011;173(1):37-42. Epub Jan. 8, 2011).*
(Continued)

*Primary Examiner* — Aaron A Priest
(74) *Attorney, Agent, or Firm* — Wilson Sonsini Goodrich & Rosati

(57) ABSTRACT

Herein, systems and methods are disclosed including a sample acquisition component (SAC) for user-friendly sample collection, a separation component for optional separation of plasma, and one or more stabilization components for stabilizing analytes. In a particular embodiment, the system and methods are directed towards sample collection and stabilization with optional sample separation. Other embodiments can perform any combination of collection, separation, stabilization or detection.

20 Claims, 12 Drawing Sheets

Related U.S. Application Data on Nov. 25, 2015, provisional application No. 62/367,056, filed on Jul. 26, 2016, provisional application No. 62/368,817, filed on Jul. 29, 2016.

(52) U.S. Cl.
CPC ...... *A61B 5/15113* (2013.01); *A61B 5/15142* (2013.01); *A61B 5/15144* (2013.01); *A61B 5/150358* (2013.01); *A61B 5/150389* (2013.01); *A61B 5/150412* (2013.01); *A61B 5/150503* (2013.01); *A61B 5/150755* (2013.01); *A61B 5/150786* (2013.01); *A61B 5/150793* (2013.01)

(58) Field of Classification Search
USPC ......................................................... 435/6.1
See application file for complete search history.

(56) References Cited

U.S. PATENT DOCUMENTS

| | | |
|---|---|---|
| 3,227,075 A | 1/1966 | Guastella et al. |
| 3,300,474 A | 1/1967 | Flodin et al. |
| 3,623,475 A | 11/1971 | Sanz et al. |
| 3,645,692 A | 2/1972 | Stork et al. |
| 4,257,426 A | 3/1981 | Bailey |
| 4,540,506 A | 9/1985 | Jacobson et al. |
| 4,972,843 A | 11/1990 | Broden |
| 5,141,850 A | 8/1992 | Cole et al. |
| 5,173,422 A | 12/1992 | Knowles et al. |
| 5,234,809 A | 8/1993 | Boom et al. |
| 5,252,489 A | 10/1993 | Macri |
| 5,320,607 A | 6/1994 | Ishibashi |
| 5,494,646 A | 2/1996 | Seymour |
| 5,496,562 A | 3/1996 | Burgoyne |
| 5,567,615 A | 10/1996 | Degen et al. |
| 5,593,824 A | 1/1997 | Treml et al. |
| 5,636,640 A | 6/1997 | Staehlin |
| 5,662,127 A | 9/1997 | De Vaughn |
| 5,680,872 A | 10/1997 | Sesekura et al. |
| 5,701,910 A | 12/1997 | Powles et al. |
| 5,709,699 A | 1/1998 | Warner |
| 5,725,774 A | 3/1998 | Neyer |
| 5,756,126 A | 5/1998 | Burgoyne |
| 5,804,684 A | 9/1998 | Su |
| 5,807,527 A | 9/1998 | Burgoyne |
| 5,906,742 A | 5/1999 | Wang et al. |
| 5,938,679 A | 8/1999 | Freeman et al. |
| 5,939,259 A | 8/1999 | Harvey et al. |
| 5,951,582 A | 9/1999 | Thorne et al. |
| 5,971,941 A | 10/1999 | Simons et al. |
| 5,972,386 A | 10/1999 | Burgoyne |
| 5,976,572 A | 11/1999 | Burgoyne |
| 5,981,218 A | 11/1999 | Rio et al. |
| 5,984,940 A | 11/1999 | Davis et al. |
| 5,985,327 A | 11/1999 | Burgoyne |
| 6,004,278 A | 12/1999 | Botich et al. |
| 6,004,574 A | 12/1999 | Baeckstroem et al. |
| 6,036,659 A | 3/2000 | Ray et al. |
| 6,036,924 A | 3/2000 | Simons et al. |
| 6,063,039 A | 5/2000 | Cunningham et al. |
| 6,093,156 A | 7/2000 | Cunningham et al. |
| 6,129,710 A | 10/2000 | Padgett et al. |
| 6,132,449 A | 10/2000 | Lum et al. |
| 6,152,942 A | 11/2000 | Brenneman et al. |
| 6,155,992 A | 12/2000 | Henning et al. |
| 6,168,922 B1 | 1/2001 | Harvey et al. |
| 6,258,045 B1 | 7/2001 | Ray et al. |
| 6,261,245 B1 | 7/2001 | Kawai et al. |
| 6,283,926 B1 | 9/2001 | Cunningham et al. |
| 6,294,203 B1 | 9/2001 | Burgoyne |
| 6,309,887 B1 | 10/2001 | Ray |
| 6,332,871 B1 | 12/2001 | Douglas et al. |
| 6,334,856 B1 | 1/2002 | Allen et al. |
| 6,340,354 B1 | 1/2002 | Rambin |
| 6,364,890 B1 | 4/2002 | Lum et al. |
| 6,419,661 B1 | 7/2002 | Kuhr et al. |
| 6,472,220 B1 | 10/2002 | Simons et al. |
| 6,485,439 B1 | 11/2002 | Roe et al. |
| 6,506,168 B1 | 1/2003 | Fathallah et al. |
| 6,528,641 B2 | 3/2003 | Lader |
| 6,558,361 B1 | 5/2003 | Yeshurun |
| 6,591,124 B2 | 7/2003 | Sherman et al. |
| 6,602,718 B1 | 8/2003 | Augello et al. |
| 6,645,717 B1 | 11/2003 | Smith et al. |
| 6,719,771 B1 | 4/2004 | Crossman |
| 6,743,211 B1 | 6/2004 | Prausnitz et al. |
| 6,752,817 B2 | 6/2004 | Flora et al. |
| 6,776,959 B1 | 8/2004 | Helftenbein |
| 6,793,633 B2 | 9/2004 | Douglas et al. |
| 6,794,140 B1 | 9/2004 | Goldsborough |
| 6,866,675 B2 | 3/2005 | Perez et al. |
| 6,867,290 B2 | 3/2005 | Goldsborough et al. |
| 6,890,319 B1 | 5/2005 | Crocker |
| 6,988,996 B2 | 1/2006 | Roe et al. |
| 7,025,774 B2 | 4/2006 | Freeman et al. |
| 7,047,070 B2 | 5/2006 | Wilkinson et al. |
| 7,056,306 B1 | 6/2006 | Halseth et al. |
| 7,077,828 B2 | 7/2006 | Kuhr et al. |
| 7,163,515 B2 | 1/2007 | McNenny |
| 7,163,793 B2 | 1/2007 | Kudlicki et al. |
| 7,211,052 B2 | 5/2007 | Roe |
| 7,235,056 B2 | 6/2007 | Duchon et al. |
| D546,440 S | 7/2007 | Burnside |
| 7,244,568 B2 | 7/2007 | Goldsborough |
| 7,250,270 B2 | 7/2007 | Goldrick et al. |
| D548,339 S | 8/2007 | Stonier et al. |
| 7,258,693 B2 | 8/2007 | Freeman et al. |
| 7,282,371 B2 | 10/2007 | Helftenbein |
| 7,291,497 B2 | 11/2007 | Holmes et al. |
| 7,344,499 B1 | 3/2008 | Prausnitz et al. |
| 7,374,546 B2 | 5/2008 | Roe et al. |
| 7,455,663 B2 | 11/2008 | Bikovsky |
| 7,473,397 B2 | 1/2009 | Griffin et al. |
| 7,589,184 B2 | 9/2009 | Hogan et al. |
| 7,638,307 B2 | 12/2009 | Hantash |
| 7,666,149 B2 | 2/2010 | Simons et al. |
| 7,666,150 B2 | 2/2010 | Douglas et al. |
| 7,682,318 B2 | 3/2010 | Alden et al. |
| 7,695,442 B2 | 4/2010 | Wong et al. |
| 7,758,516 B2 | 7/2010 | Perez |
| 7,758,518 B2 | 7/2010 | Perez et al. |
| 7,766,846 B2 | 8/2010 | Wong et al. |
| 7,822,454 B1 | 10/2010 | Alden et al. |
| 7,828,749 B2 | 11/2010 | Douglas et al. |
| 7,833,170 B2 | 11/2010 | Matsumoto et al. |
| 7,892,185 B2 | 2/2011 | Freeman et al. |
| 7,922,462 B2 | 4/2011 | Preuthun et al. |
| 7,955,347 B2 | 6/2011 | Stout |
| 8,025,850 B2 | 9/2011 | Chan et al. |
| 8,048,681 B2 | 11/2011 | Yamashita et al. |
| 8,062,608 B2 | 11/2011 | Pankow |
| 8,088,576 B2 | 1/2012 | Gumbrecht et al. |
| 8,142,723 B2 | 3/2012 | Menon et al. |
| 8,158,357 B2 | 4/2012 | Birnboim et al. |
| 8,283,165 B2 | 10/2012 | Hogan et al. |
| 8,328,023 B2 | 12/2012 | Weiss et al. |
| 8,333,712 B2 | 12/2012 | Imamura et al. |
| 8,337,419 B2 | 12/2012 | Freeman et al. |
| 8,337,420 B2 | 12/2012 | Freeman |
| 8,337,464 B2 | 12/2012 | Young et al. |
| 8,360,991 B2 | 1/2013 | Freeman et al. |
| 8,431,384 B2 | 4/2013 | Hogan et al. |
| 8,469,986 B2 | 6/2013 | Schraga |
| 8,470,536 B2 | 6/2013 | Birnboim et al. |
| 8,474,332 B2 | 7/2013 | Bente, IV et al. |
| 8,519,125 B2 | 8/2013 | Whitney et al. |
| 8,561,795 B2 | 10/2013 | Schott |
| 8,574,169 B2 | 11/2013 | Hoenes |
| 8,636,041 B2 | 1/2014 | Yodfat |
| 8,636,673 B2 | 1/2014 | Freeman et al. |
| 8,657,763 B2 | 2/2014 | Jacobs |
| 8,663,538 B2 | 3/2014 | Amirouche et al. |
| 8,696,596 B2 | 4/2014 | Douglas et al. |

(56) References Cited

U.S. PATENT DOCUMENTS

| | | |
|---|---|---|
| 8,708,928 B2 | 4/2014 | Videbaek et al. |
| 8,709,363 B2 * | 4/2014 | Petersen ............... B01L 7/52 |
| | | 422/554 |
| 8,808,202 B2 | 8/2014 | Brancazio |
| 8,821,412 B2 | 9/2014 | Gonzalez-Zugasti et al. |
| 8,827,971 B2 | 9/2014 | Gonzalez-Zugasti et al. |
| 8,835,146 B2 * | 9/2014 | Battrell ............ C12N 9/1252 |
| | | 435/188 |
| 8,845,550 B2 | 9/2014 | Freeman et al. |
| 8,852,123 B2 | 10/2014 | Roe et al. |
| 8,900,856 B2 | 12/2014 | Muller-Cohn et al. |
| 8,932,313 B2 | 1/2015 | Weiss et al. |
| 8,951,719 B2 | 2/2015 | Hogan et al. |
| 8,961,787 B2 | 2/2015 | Wood et al. |
| 8,979,770 B2 * | 3/2015 | Fare ................. C12N 15/1017 |
| | | 600/584 |
| 8,998,851 B2 | 4/2015 | Constantineau et al. |
| 9,023,292 B2 | 5/2015 | Rostaing et al. |
| 9,033,898 B2 | 5/2015 | Chickering, III et al. |
| 9,040,236 B2 | 5/2015 | Hill et al. |
| 9,040,675 B2 | 5/2015 | Bales et al. |
| 9,040,679 B2 | 5/2015 | Kvam et al. |
| 9,041,541 B2 | 5/2015 | Levinson et al. |
| 9,044,738 B2 | 6/2015 | Li et al. |
| 9,078,426 B2 | 7/2015 | Muller-Cohn et al. |
| 9,113,836 B2 | 8/2015 | Bernstein et al. |
| 9,119,578 B2 | 9/2015 | Haghgooie et al. |
| 9,176,126 B2 | 11/2015 | Holmes et al. |
| 9,192,254 B2 | 11/2015 | Gilbert et al. |
| 9,217,167 B2 | 12/2015 | Heller et al. |
| 9,289,763 B2 | 3/2016 | Berthier et al. |
| 9,295,417 B2 | 3/2016 | Haghgooie et al. |
| 9,314,764 B2 * | 4/2016 | Hess .................... B01L 13/02 |
| 9,353,393 B2 | 5/2016 | Nelson et al. |
| 9,359,649 B2 | 6/2016 | Lloyd, Jr. et al. |
| 9,380,972 B2 | 7/2016 | Fletcher et al. |
| 9,408,568 B2 | 8/2016 | Fletcher et al. |
| 9,415,392 B2 | 8/2016 | Ismagilov et al. |
| 9,427,184 B2 | 8/2016 | Holmes et al. |
| 9,480,966 B2 | 11/2016 | Kovacs et al. |
| 9,480,981 B2 | 11/2016 | Lenigk et al. |
| 9,517,026 B2 | 12/2016 | Gelfand et al. |
| 9,534,214 B2 | 1/2017 | Li et al. |
| 9,535,052 B2 * | 1/2017 | Singh ................. G01N 33/491 |
| 9,554,736 B2 | 1/2017 | Gupta et al. |
| 9,623,409 B2 | 4/2017 | Khattak et al. |
| 9,629,579 B2 | 4/2017 | Volkmuth et al. |
| 9,636,062 B2 | 5/2017 | Holmes et al. |
| 9,707,384 B2 | 7/2017 | La et al. |
| 9,718,058 B2 | 8/2017 | Khattak et al. |
| 9,730,624 B2 | 8/2017 | Gonzalez-Zugasti et al. |
| 9,730,625 B2 | 8/2017 | Krasnow et al. |
| 9,775,551 B2 | 10/2017 | Bernstein et al. |
| 9,795,960 B2 | 10/2017 | Maillefer et al. |
| 9,901,922 B2 | 2/2018 | Lenigk et al. |
| 9,938,568 B2 | 4/2018 | Heller et al. |
| 9,950,321 B2 | 4/2018 | Griffin et al. |
| 9,970,794 B2 | 5/2018 | DeKalb |
| 10,076,630 B2 | 9/2018 | Young et al. |
| 10,183,127 B2 | 1/2019 | Martin et al. |
| 10,188,335 B2 | 1/2019 | Haghgooie et al. |
| 10,335,078 B2 | 7/2019 | Kvam et al. |
| 10,335,784 B2 | 7/2019 | Maillefer et al. |
| 10,350,592 B2 | 7/2019 | Lenigk et al. |
| 10,371,608 B2 | 8/2019 | Algotsson et al. |
| 10,426,390 B2 | 10/2019 | Berthier et al. |
| D870,264 S | 12/2019 | Fedor et al. |
| 10,492,716 B2 | 12/2019 | Berthier et al. |
| 10,543,310 B2 | 1/2020 | Bernstein et al. |
| 10,569,012 B2 | 2/2020 | Schabbach et al. |
| 10,597,697 B2 | 3/2020 | Nelson et al. |
| 10,625,242 B2 | 4/2020 | Kovacs et al. |
| 10,638,963 B2 | 5/2020 | Beyerlein et al. |
| 10,655,167 B2 | 5/2020 | Heller et al. |
| D892,310 S | 8/2020 | Jordan et al. |
| 10,737,021 B2 | 8/2020 | Deck |
| 10,876,938 B2 | 12/2020 | Horton et al. |
| 10,888,259 B2 | 1/2021 | Jordan et al. |
| 10,898,643 B2 | 1/2021 | Gyrn et al. |
| 10,932,710 B2 | 3/2021 | Jordan et al. |
| 10,939,860 B2 | 3/2021 | Levinson et al. |
| 10,940,264 B2 | 3/2021 | Smith et al. |
| 11,033,212 B2 | 6/2021 | Berthier et al. |
| 2001/0007746 A1 | 7/2001 | Smith et al. |
| 2001/0039010 A1 | 11/2001 | Burgoyne |
| 2002/0146696 A1 | 10/2002 | Burgoyne et al. |
| 2003/0134312 A1 | 7/2003 | Burgoyne |
| 2003/0143566 A1 | 7/2003 | Helftenbein |
| 2003/0198968 A1 | 10/2003 | Matson |
| 2003/0212345 A1 | 11/2003 | McAllister et al. |
| 2003/0215358 A1 | 11/2003 | Schulman et al. |
| 2004/0009496 A1 | 1/2004 | Eiblmaier et al. |
| 2004/0087990 A1 | 5/2004 | Boecker et al. |
| 2004/0096914 A1 | 5/2004 | Fang et al. |
| 2004/0101895 A1 | 5/2004 | Fomovskaia et al. |
| 2004/0112237 A1 | 6/2004 | Chaug et al. |
| 2004/0126783 A1 | 7/2004 | Bortolin et al. |
| 2004/0202576 A1 | 10/2004 | Aceti et al. |
| 2004/0219534 A1 | 11/2004 | Belly et al. |
| 2004/0235034 A1 | 11/2004 | Kuno et al. |
| 2005/0009045 A1 | 1/2005 | Greenfield et al. |
| 2005/0065466 A1 | 3/2005 | Vedrine |
| 2005/0112034 A1 | 5/2005 | Mccormick |
| 2005/0123965 A1 | 6/2005 | Yamashita et al. |
| 2005/0222539 A1 | 10/2005 | Gonzales et al. |
| 2005/0245844 A1 | 11/2005 | Mace et al. |
| 2006/0030790 A1 | 2/2006 | Braig et al. |
| 2006/0068399 A1 * | 3/2006 | McMillan ............. C12Q 1/6846 |
| | | 435/6.11 |
| 2006/0099567 A1 | 5/2006 | Muller-Cohn et al. |
| 2006/0147918 A1 | 7/2006 | Goldsborough |
| 2006/0178599 A1 | 8/2006 | Faupel et al. |
| 2006/0200044 A1 | 9/2006 | Freeman et al. |
| 2006/0234251 A1 | 10/2006 | Akhavan-Tafti |
| 2006/0240451 A1 | 10/2006 | Jendrisak et al. |
| 2006/0293722 A1 | 12/2006 | Slatkine et al. |
| 2007/0087357 A1 | 4/2007 | Clark et al. |
| 2007/0088248 A1 | 4/2007 | Glenn et al. |
| 2007/0106071 A1 | 5/2007 | Yamashita et al. |
| 2007/0117173 A1 | 5/2007 | Levison et al. |
| 2007/0123803 A1 | 5/2007 | Fujiwara et al. |
| 2008/0003602 A1 | 1/2008 | Nelson et al. |
| 2008/0027368 A1 | 1/2008 | Kollar et al. |
| 2008/0081976 A1 | 4/2008 | Hodges et al. |
| 2008/0145272 A1 | 6/2008 | Feaster et al. |
| 2008/0176209 A1 | 7/2008 | Muller et al. |
| 2008/0262097 A1 | 10/2008 | Eady et al. |
| 2008/0286150 A1 | 11/2008 | Pankow |
| 2009/0024098 A1 | 1/2009 | Bizup et al. |
| 2009/0043087 A1 | 2/2009 | Davis et al. |
| 2009/0053704 A1 | 2/2009 | Novoradovskaya et al. |
| 2009/0104637 A1 | 4/2009 | Ismagilov et al. |
| 2009/0130720 A1 | 5/2009 | Nelson et al. |
| 2009/0143570 A1 | 6/2009 | Jiang et al. |
| 2009/0155838 A1 | 6/2009 | Hale |
| 2009/0162924 A1 | 6/2009 | Birnboim |
| 2009/0208919 A1 | 8/2009 | Utermohlen et al. |
| 2009/0221976 A1 | 9/2009 | Linden |
| 2009/0246750 A1 | 10/2009 | Lloyd et al. |
| 2009/0291427 A1 | 11/2009 | Muller-Cohn et al. |
| 2009/0299224 A1 | 12/2009 | Yoo |
| 2010/0010374 A1 | 1/2010 | Escutia et al. |
| 2010/0042073 A1 | 2/2010 | Oster et al. |
| 2010/0099074 A1 | 4/2010 | Nolan et al. |
| 2010/0099149 A1 | 4/2010 | Birnboim et al. |
| 2010/0121283 A1 | 5/2010 | Hamatake et al. |
| 2010/0145230 A1 | 6/2010 | Wong et al. |
| 2010/0173392 A1 | 7/2010 | Davis et al. |
| 2010/0209930 A1 | 8/2010 | Fernando |
| 2010/0209957 A1 | 8/2010 | Hogan et al. |
| 2010/0248363 A1 | 9/2010 | Hogan et al. |
| 2010/0256465 A1 | 10/2010 | Bernstein et al. |
| 2010/0256524 A1 | 10/2010 | Levinson et al. |
| 2010/0261988 A1 | 10/2010 | Tamir |

(56) References Cited

U.S. PATENT DOCUMENTS

| | | |
|---|---|---|
| 2010/0297710 A1 | 11/2010 | Hoyal-Wrightson et al. |
| 2010/0323343 A1 | 12/2010 | Egan et al. |
| 2011/0009847 A1 | 1/2011 | Levinson et al. |
| 2011/0027771 A1 | 2/2011 | Deng |
| 2011/0054157 A1 | 3/2011 | Bitner |
| 2011/0059441 A1 | 3/2011 | Pelton et al. |
| 2011/0070585 A1 | 3/2011 | Ollikka et al. |
| 2011/0081363 A1 | 4/2011 | Whitney et al. |
| 2011/0091990 A1 | 4/2011 | Dastane et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0118677 A1 | 5/2011 | Wiley et al. |
| 2011/0125058 A1 | 5/2011 | Levinson et al. |
| 2011/0125059 A1 | 5/2011 | Petrich et al. |
| 2011/0130558 A1 | 6/2011 | Ritt et al. |
| 2011/0172508 A1 | 7/2011 | Chickering, III et al. |
| 2011/0172510 A1 | 7/2011 | Chickering, III et al. |
| 2011/0183338 A1 | 7/2011 | Bischoff |
| 2011/0194996 A1 | 8/2011 | Selinfreund et al. |
| 2011/0212002 A1 | 9/2011 | Curry et al. |
| 2011/0224106 A1 | 9/2011 | Eshoo et al. |
| 2011/0244467 A1 | 10/2011 | Haswell |
| 2011/0288389 A9 | 11/2011 | Levinson et al. |
| 2011/0306853 A1 | 12/2011 | Black et al. |
| 2012/0010529 A1* | 1/2012 | Chickering, III .... A61B 5/1411 600/576 |
| 2012/0016308 A1 | 1/2012 | Schott |
| 2012/0024788 A1 | 2/2012 | Kelso et al. |
| 2012/0039809 A1 | 2/2012 | Levinson et al. |
| 2012/0041338 A1 | 2/2012 | Chickering, III et al. |
| 2012/0052572 A1 | 3/2012 | Whitney et al. |
| 2012/0059160 A1 | 3/2012 | Bitner et al. |
| 2012/0074073 A1 | 3/2012 | Coull et al. |
| 2012/0138862 A1 | 6/2012 | Hogan |
| 2012/0149128 A1 | 6/2012 | Manneh |
| 2012/0152743 A1 | 6/2012 | Finehout et al. |
| 2012/0158100 A1 | 6/2012 | Schomacker |
| 2012/0164691 A1 | 6/2012 | Eshoo et al. |
| 2012/0237939 A1 | 9/2012 | Reed et al. |
| 2012/0271125 A1 | 10/2012 | Bernstein et al. |
| 2012/0275955 A1 | 11/2012 | Haghgooie et al. |
| 2012/0277629 A1* | 11/2012 | Bernstein .......... B01L 3/502753 600/578 |
| 2012/0288889 A1 | 11/2012 | Miyamura |
| 2012/0289690 A1 | 11/2012 | Page et al. |
| 2013/0018279 A1 | 1/2013 | Plante et al. |
| 2013/0102501 A1 | 4/2013 | Craighead et al. |
| 2013/0143226 A1 | 6/2013 | Hill et al. |
| 2013/0150811 A1 | 6/2013 | Horgan |
| 2013/0158468 A1 | 6/2013 | Bernstein et al. |
| 2013/0158482 A1 | 6/2013 | Davis et al. |
| 2013/0172698 A1 | 7/2013 | Reynolds et al. |
| 2013/0190578 A1 | 7/2013 | Freeman et al. |
| 2013/0209997 A1 | 8/2013 | Whitney et al. |
| 2013/0211289 A1* | 8/2013 | Moga ................. A61B 5/15146 600/578 |
| 2013/0280725 A1 | 10/2013 | Ismagilov et al. |
| 2013/0289257 A1 | 10/2013 | Bales et al. |
| 2013/0289265 A1 | 10/2013 | Li et al. |
| 2013/0309679 A1 | 11/2013 | Ismagilov et al. |
| 2013/0323723 A1 | 12/2013 | Horton et al. |
| 2013/0330750 A1 | 12/2013 | Horton et al. |
| 2013/0337432 A1 | 12/2013 | Cook et al. |
| 2013/0338351 A1 | 12/2013 | Kvam et al. |
| 2014/0000392 A1 | 1/2014 | Harvey et al. |
| 2014/0038172 A1 | 2/2014 | De et al. |
| 2014/0038306 A1 | 2/2014 | Berthier et al. |
| 2014/0039172 A1 | 2/2014 | Nelson et al. |
| 2014/0080112 A1 | 3/2014 | Ryan et al. |
| 2014/0100525 A1 | 4/2014 | Freeman |
| 2014/0207086 A1 | 7/2014 | Stats et al. |
| 2014/0227686 A1 | 8/2014 | Saghbini et al. |
| 2014/0227687 A1 | 8/2014 | Horlitz et al. |
| 2014/0234942 A1* | 8/2014 | Kovacs ................. B01J 20/22 435/207 |
| 2014/0272925 A1 | 9/2014 | Menon et al. |
| 2014/0273058 A1 | 9/2014 | Menon et al. |
| 2014/0295429 A1 | 10/2014 | Hogan et al. |
| 2014/0302521 A1 | 10/2014 | Algotsson et al. |
| 2014/0305197 A1 | 10/2014 | Fletcher et al. |
| 2014/0305823 A1 | 10/2014 | Gelfand et al. |
| 2014/0308164 A1 | 10/2014 | Wilkinson et al. |
| 2014/0309555 A1 | 10/2014 | Gelfand et al. |
| 2014/0309556 A1 | 10/2014 | Fletcher et al. |
| 2014/0309557 A1 | 10/2014 | Fletcher et al. |
| 2014/0309558 A1 | 10/2014 | Fletcher et al. |
| 2014/0323911 A1 | 10/2014 | Sloan et al. |
| 2014/0323913 A1 | 10/2014 | Holmes et al. |
| 2014/0336536 A1 | 11/2014 | Brancazio |
| 2014/0342371 A1 | 11/2014 | Holmes |
| 2014/0343481 A1 | 11/2014 | Ignon |
| 2014/0358036 A1 | 12/2014 | Holmes |
| 2015/0031035 A1* | 1/2015 | Kvam ................. B01L 3/5023 435/6.12 |
| 2015/0038876 A1 | 2/2015 | Gonzalez-Zugasti et al. |
| 2015/0056614 A1 | 2/2015 | Mikolajczyk et al. |
| 2015/0057510 A1 | 2/2015 | Levinson et al. |
| 2015/0076054 A1 | 3/2015 | Anekal et al. |
| 2015/0079194 A1* | 3/2015 | Hanna ................. B01D 69/02 424/530 |
| 2015/0087944 A1 | 3/2015 | Levinson et al. |
| 2015/0118683 A1 | 4/2015 | Li et al. |
| 2015/0119566 A1 | 4/2015 | Li et al. |
| 2015/0125882 A1 | 5/2015 | Bornheimer et al. |
| 2015/0132860 A1 | 5/2015 | Cook et al. |
| 2015/0158902 A1 | 6/2015 | Hogan et al. |
| 2015/0164398 A1 | 6/2015 | Ko et al. |
| 2015/0165346 A1 | 6/2015 | Puleo et al. |
| 2015/0211967 A1 | 7/2015 | Gooley et al. |
| 2015/0259671 A1 | 9/2015 | Puleo et al. |
| 2015/0273467 A1 | 10/2015 | Sloan et al. |
| 2015/0299693 A1 | 10/2015 | Chen et al. |
| 2015/0313522 A1 | 11/2015 | Bernstein et al. |
| 2015/0320349 A1 | 11/2015 | Haghgooie et al. |
| 2016/0023209 A1 | 1/2016 | Lenigk et al. |
| 2016/0029936 A1 | 2/2016 | Kvam et al. |
| 2016/0030895 A1* | 2/2016 | Griffin ................. B01L 3/5023 210/335 |
| 2016/0038068 A1 | 2/2016 | Chickering, III et al. |
| 2016/0053307 A1 | 2/2016 | Heller et al. |
| 2016/0135446 A1 | 5/2016 | Muller-Cohn et al. |
| 2016/0143568 A1 | 5/2016 | List |
| 2016/0174888 A1 | 6/2016 | Berthier et al. |
| 2016/0230219 A1 | 8/2016 | Nelson et al. |
| 2016/0262676 A1 | 9/2016 | Haghgooie et al. |
| 2016/0290901 A1 | 10/2016 | Dick et al. |
| 2016/0292393 A1 | 10/2016 | Balwani |
| 2016/0313298 A1 | 10/2016 | Wright et al. |
| 2017/0021067 A1 | 1/2017 | Todd et al. |
| 2017/0021333 A1 | 1/2017 | Li et al. |
| 2017/0035337 A1 | 2/2017 | Wilkinson et al. |
| 2017/0095190 A1 | 4/2017 | Sloan et al. |
| 2017/0120022 A1 | 5/2017 | Chickering, III et al. |
| 2017/0120023 A1 | 5/2017 | Davis et al. |
| 2017/0127991 A1 | 5/2017 | Bernstein et al. |
| 2017/0172481 A1 | 6/2017 | Berthier et al. |
| 2017/0203292 A1 | 7/2017 | Lenigk et al. |
| 2017/0211059 A1 | 7/2017 | Kvam et al. |
| 2017/0224264 A1 | 8/2017 | Brancazio |
| 2017/0282177 A1 | 10/2017 | Bedrio |
| 2017/0298415 A1 | 10/2017 | Heller et al. |
| 2017/0335313 A1* | 11/2017 | Qian ................. C12N 15/1017 |
| 2017/0354361 A1* | 12/2017 | Tan ................. A61B 5/150343 |
| 2018/0008183 A1 | 1/2018 | Chickering, III et al. |
| 2018/0074042 A1 | 3/2018 | Kelso et al. |
| 2018/0078241 A1 | 3/2018 | Moga et al. |
| 2018/0078751 A1 | 3/2018 | Fedor et al. |
| 2018/0223349 A1 | 8/2018 | Heller et al. |
| 2019/0000365 A1 | 1/2019 | Beyerlein et al. |
| 2019/0159709 A1 | 5/2019 | Barone et al. |
| 2019/0336058 A1 | 11/2019 | Haghgooie et al. |
| 2020/0037940 A1 | 2/2020 | Berthier et al. |

(56) References Cited

U.S. PATENT DOCUMENTS

| | | | |
|---|---|---|---|
| 2020/0085414 A1 | 3/2020 | Berthier et al. |
| 2020/0163603 A1 | 5/2020 | Jordan et al. |
| 2020/0164359 A1 | 5/2020 | Jordan et al. |
| 2020/0164362 A1 | 5/2020 | Jordan et al. |
| 2020/0323473 A1 | 10/2020 | Berthier et al. |
| 2021/0106261 A1 | 4/2021 | Queval |
| 2021/0137435 A1 | 5/2021 | Queval |
| 2021/0177383 A1 | 6/2021 | Moga et al. |

FOREIGN PATENT DOCUMENTS

| | | |
|---|---|---|
| CN | 101203177 B | 5/2010 |
| CN | 1968652 B | 6/2010 |
| CN | 101878304 A | 11/2010 |
| CN | 101674773 B | 7/2012 |
| CN | 101454038 B | 11/2012 |
| CN | 102803483 A | 11/2012 |
| CN | 103173432 A | 6/2013 |
| CN | 103370007 A | 10/2013 |
| CN | 103380376 A | 10/2013 |
| CN | 203838155 U | 9/2014 |
| CN | 104107058 A | 10/2014 |
| CN | 102405018 B | 11/2014 |
| CN | 102497814 B | 1/2015 |
| CN | 102309330 B | 4/2015 |
| CN | 102791197 B | 3/2016 |
| CN | 103068308 B | 3/2016 |
| CN | 103874460 B | 6/2016 |
| CN | 102648015 B | 10/2016 |
| CN | 102405015 B | 1/2017 |
| CN | 102811754 B | 5/2017 |
| CN | 103260516 B | 5/2017 |
| CN | 103874461 B | 5/2017 |
| CN | 107115115 A | 9/2017 |
| CN | 107260186 A | 10/2017 |
| CN | 107708560 A | 2/2018 |
| EP | 0392377 A2 | 10/1990 |
| EP | 1437093 A1 | 7/2004 |
| EP | 1484111 A1 | 12/2004 |
| EP | 1559784 A2 | 8/2005 |
| EP | 1746419 A1 | 1/2007 |
| EP | 2040076 A2 | 3/2009 |
| EP | 2376689 A1 | 10/2011 |
| EP | 2388312 A1 | 11/2011 |
| EP | 2396430 A1 | 12/2011 |
| EP | 2701601 A1 | 3/2014 |
| EP | 2702406 A1 | 3/2014 |
| EP | 2593014 B1 | 11/2015 |
| EP | 3106092 A2 | 12/2016 |
| EP | 3174463 A1 | 6/2017 |
| EP | 2493536 B1 | 9/2017 |
| EP | 3235429 A1 | 10/2017 |
| EP | 3236259 A1 | 10/2017 |
| EP | 3087919 B1 | 9/2018 |
| EP | 3393342 A1 | 10/2018 |
| EP | 3490453 A1 | 6/2019 |
| EP | 3515521 A1 | 7/2019 |
| EP | 3566649 A1 | 11/2019 |
| EP | 3760106 A2 | 1/2021 |
| EP | 3769682 A1 | 1/2021 |
| EP | 3793442 A1 | 3/2021 |
| EP | 3820368 A1 | 5/2021 |
| EP | 3821804 A1 | 5/2021 |
| GB | 1356346 A | 6/1974 |
| GB | 1601283 A | 10/1981 |
| GB | WO 9640077 A2 * | 12/1996 ............ A61K 9/2018 |
| GB | 2381482 A | 5/2003 |
| JP | S5319092 A | 2/1978 |
| JP | S6188896 A | 5/1986 |
| JP | H01291164 A | 11/1989 |
| JP | H03503212 A | 7/1991 |
| JP | H10179722 A | 7/1998 |
| JP | 2002085384 A | 3/2002 |
| JP | 2004329213 A | 11/2004 |
| JP | 2007502428 A | 2/2007 |
| JP | 2007124952 A | 5/2007 |
| JP | 2008022988 A | 2/2008 |
| JP | 2008099988 A | 5/2008 |
| JP | 2008099991 A | 5/2008 |
| JP | 2008099992 A | 5/2008 |
| JP | 4189321 B2 | 12/2008 |
| JP | 2010536377 A | 12/2010 |
| JP | 2011521709 A | 7/2011 |
| JP | 2012523851 A | 10/2012 |
| JP | 5282088 B2 | 9/2013 |
| JP | 5416222 B2 | 2/2014 |
| JP | 2014516644 A | 7/2014 |
| JP | 5766178 B2 | 8/2015 |
| JP | 6058063 B2 | 1/2017 |
| JP | 2017522117 A | 8/2017 |
| SE | WO 2015162093 A1 * | 10/2015 ............ C07K 7/06 |
| WO | WO-9118091 A1 | 11/1991 |
| WO | WO-9202175 A1 | 2/1992 |
| WO | WO-9624062 A1 | 8/1996 |
| WO | WO-9824366 A2 | 6/1998 |
| WO | WO-9824493 A1 | 6/1998 |
| WO | WO-0021664 A1 | 4/2000 |
| WO | WO-0066606 A1 | 11/2000 |
| WO | WO-0074763 A2 | 12/2000 |
| WO | WO-0143643 A1 | 6/2001 |
| WO | WO-03020924 A2 | 3/2003 |
| WO | WO-03086443 A1 | 10/2003 |
| WO | WO-03094770 A1 | 11/2003 |
| WO | WO-2004066822 A2 | 8/2004 |
| WO | WO-2005066636 A1 | 7/2005 |
| WO | WO-2005095653 A2 | 10/2005 |
| WO | WO-2005116651 A2 | 12/2005 |
| WO | WO-2006047787 A2 | 5/2006 |
| WO | WO-2006071776 A2 | 7/2006 |
| WO | WO-2006118622 A1 | 11/2006 |
| WO | WO-2006118707 A2 | 11/2006 |
| WO | WO-2007008722 A2 | 1/2007 |
| WO | WO-2007035585 A2 | 3/2007 |
| WO | WO-2007056338 A2 | 5/2007 |
| WO | WO-2008045505 A2 | 4/2008 |
| WO | WO-2008075213 A2 | 6/2008 |
| WO | WO-2008084219 A1 | 7/2008 |
| WO | WO-2008144439 A1 | 11/2008 |
| WO | WO-2009027950 A2 | 3/2009 |
| WO | WO-2009029433 A2 | 3/2009 |
| WO | WO-2009090174 A1 | 7/2009 |
| WO | WO-2009148624 A1 | 12/2009 |
| WO | WO-2009155612 A2 | 12/2009 |
| WO | WO-2010031007 A2 | 3/2010 |
| WO | WO-2010074773 A1 | 7/2010 |
| WO | WO-2010094040 A1 | 8/2010 |
| WO | WO-2010101620 A2 | 9/2010 |
| WO | WO-2010123908 A1 | 10/2010 |
| WO | WO-2010132508 A2 | 11/2010 |
| WO | WO-2010144682 A1 | 12/2010 |
| WO | WO-2011019656 A1 | 2/2011 |
| WO | WO-2011026169 A1 | 3/2011 |
| WO | WO-2011088211 A2 | 7/2011 |
| WO | WO-2011131720 A1 | 10/2011 |
| WO | WO-2012075471 A1 | 6/2012 |
| WO | WO-2012113906 A2 | 8/2012 |
| WO | WO-2012113907 A2 | 8/2012 |
| WO | WO-2012113911 A1 | 8/2012 |
| WO | WO-2012135815 A2 | 10/2012 |
| WO | WO-2012149126 A1 | 11/2012 |
| WO | WO-2012149134 A1 | 11/2012 |
| WO | WO-2012154362 A1 | 11/2012 |
| WO | WO-2013066249 A1 | 5/2013 |
| WO | WO-2013123187 A1 | 8/2013 |
| WO | WO-2013165870 A1 | 11/2013 |
| WO | WO-2014088606 A2 | 6/2014 |
| WO | WO-2014099121 A1 | 6/2014 |
| WO | WO-2014153181 A1 | 9/2014 |
| WO | WO-2015013486 A1 | 1/2015 |
| WO | WO-2015013604 A1 | 1/2015 |
| WO | WO-2015022410 A1 | 2/2015 |
| WO | WO-2015095853 A1 | 6/2015 |
| WO | WO-2015108598 A2 | 7/2015 |
| WO | WO-2015110833 A1 | 7/2015 |

(56) References Cited

FOREIGN PATENT DOCUMENTS

| | | |
|---|---|---|
| WO | WO-2015162093 A1 | 10/2015 |
| WO | WO-2015191633 A1 | 12/2015 |
| WO | WO-2016012392 A1 | 1/2016 |
| WO | WO-2016012394 A1 | 1/2016 |
| WO | WO-2016019388 A1 | 2/2016 |
| WO | WO-2016020354 A1 | 2/2016 |
| WO | WO-2016053638 A1 | 4/2016 |
| WO | WO-2016134324 A1 | 8/2016 |
| WO | WO-2016180990 A1 | 11/2016 |
| WO | WO-2017024115 A1 | 2/2017 |
| WO | WO-2017044887 A1 | 3/2017 |
| WO | WO-2017079114 A1 | 5/2017 |
| WO | WO-2017083252 A1 | 5/2017 |
| WO | WO-2017112793 A1 | 6/2017 |
| WO | WO-2017214338 A1 | 12/2017 |
| WO | WO-2018022535 A1 | 2/2018 |
| WO | WO-2018132515 A1 | 7/2018 |
| WO | WO-2019220340 A1 | 11/2019 |
| WO | WO-2020056382 A1 | 3/2020 |
| WO | WO-2021188594 A1 | 9/2021 |

OTHER PUBLICATIONS

Tao et al. (Evaluation of a solid matrix for collection and ambient storage of RNA from whole blood, BMC Clin Pathol. May 13, 2014;14:22. eCollection 2014).*
Begolo et al. (A microfluidic device for dry sample preservation in remote settings, Lab Chip, 2013, 13, 4331-4342, published Sep. 17, 2013).*
Homsy et al. (Development and validation of a low cost blood filtration element separating plasma from undiluted whole blood, Biomicrofluidics. Mar. 2012;6(1):12804-128049. doi: 10.1063/1.3672188. Epub Mar. 15, 2012).*
University of Wisconsin-Madison (Biomedical engineers offer much-needed update for blood-sampling process, published May 15, 2014, available at https://www.engr.wisc.edu/biomedical-engineers-offer-much-needed-update-for-blood-sampling-process/).*
Dauner et al. (Evaluation of nucleic acid stabilization products for ambient temperature shipping and storage of viral RNA and antibody in a dried whole blood format, Am J Trop Med Hyg. Jul. 2015;93(1):46-53. Epub May 4, 2015).*
GenTegra (Tasso and GenTegra simplify blood draws, awarded $3M expansion, attached, Apr. 7, 2015).*
Cowans, et al. Evaluation of a dried blood spot assay to measure prenatal screening markers pregnancy-associated plasma protein a and free β-subunit of human chorionic gonadotropin. Clin Chem. Jun. 2013;59(6):968-75. doi: 10.1373/clinchem.2012.194894. Epub Feb. 20, 2013.
Lo, et al. Quantitative analysis of fetal DNA in maternal plasma and serum: implications for noninvasive prenatal diagnosis. Am J Hum Genet. Apr. 1998;62(4):768-75.
Norwitz, et al. Noninvasive prenatal testing: the future is now. Rev Obstet Gynecol. 2013;6(2):48-62.
Tao, et al. Evaluation of a solid matrix for collection and ambient storage of RNA from whole blood. BMC Clin Pathol. 2014; 14: 22. Published online May 13, 2014. doi: 10.1186/1472-6890-14-22.
Innovac Quick Draw: Available at http://www.innovativemedtech.com/products/innovac-quick-draw/. Captured: Sep. 1, 2015; Accessed: Nov. 1, 2016.
"International search report with written opinion dated Jan. 10, 2017 for PCT/US2016/051157".
MicroPoint: One-step body fluid sampling platform. Available at http://www.micropointtech.com/our-products/one-step-blood-sampling-platform; Captured: Aug. 1, 2015; Accessed: Nov. 1, 2015.
MICROSAFE capillaries from Safe-Tec, LLC: available at http://www.safe-tecinc.com/microsafe. Captured: May 5, 2015. Accessed: Nov. 1, 2016.
Patel, Prachi. Paper Diagnostics That Cost Pennies. Scientific American 315, 40 (2016); Published online: Nov. 15, 2016; doi:10.1038/scientificamerican1216-40.

Affan, et al. Comparability of HbA1c and lipids measured with dried blood spot versus venous samples: a systematic review and meta-analysis. BMC Clin Pathol. May 1, 20142;14:21. doi: 10.1186/1472-6890-14-21. eCollection 2014.
Ambion Technotes. Maximize Your RNA Yield: What Yield to Expect. vol. No. 8, Issue No. 3, pp. 1, 13-14, I, May 18, 2001.
American Diabetes Association. Standards of Medical Care in Diabetes—2017 Abridged for Primary Care Providers. Clinical Diabetes Jan. 2017; 35(1): 5-26. https://doi.org/10.2337/cd16-0067.
Beck, et al. Profile of the circulating DNA in apparently healthy individuals. Clin Chem. Apr. 2009;55(4):730-8. doi: 10.1373/clinchem.2008.113597. Epub Jan. 30, 2009.
Blondal, et al. Isolation and characterization of a thermostable RNA ligase 1 from a Thermus scotoductus bacteriophage TS2126 with good single-stranded DNA ligation properties. Nucleic Acids Res. 2005; 33(1): 135-142. Published online Jan. 7, 2005. doi: 10.1093/nar/gki149.
Canadian Diabetes Association. Diabetes association 2013 clinical practice guidelines for the the prevention and management of diabetes in Canada. Canadian Journal of Diabetes. Apr. 2013, vol. 37. 227 pages.
Chiu, et al. Effects of blood-processing protocols on fetal and total DNA quantification in maternal plasma. Clin Chem. Sep. 2001;47(9):1607-13.
Cline, et al. New Water-Soluble Phosphines as Reductants of Peptide and Protein Disulfide Bonds: Reactivity and Permeability. 2004, Biochemistry 43, pp. 15195-15203.
Communication Pursuant to Article 94(3) EPC dated Apr. 10, 2017 for European Patent Application No. EP14750104.3.
Dictionary.com. Definition of the word "tissue". Accessed May 25, 2015. URL:< http://www.dictionary.com/browse/tissue?s=t>.
Editors of Consumer Guide. How to Remove Milk and Cream Stains. Howstuffworks.com. Published Mar. 23, 2006. Accessed May 25, 2015. URL:< http://home.howstuffworks.com/how-to-remove-milk-and-cream-stains.htm>.
Epicentre®. CircLigaseTM II ssDNA Ligase: Cat. Nos. CL9021K and CL9025K. 2011. 5 pages.
Eross, et al. Colorimetric measurement of glycosylated protein in whole blood, red blood cells, plasma and dried blood. Ann Clin Biochem. Nov. 1984;21 (Pt 6):477-83.
European Search Report dated Jan. 29, 2015 for European Patent Application No. EP13784927.9.
European Search Report dated May 19, 2015 for EP No. 12846138.1.
Examination Report dated Feb. 9, 2017 for Australian Patent Application No. AU2015250915.
Examination Report dated May 29, 2017 for Singaporean Patent Application No. SG11201600615V.
Extended European Search Report and Search Opinion dated Jun. 28, 2016 for European Patent Application No. EP13865596.4.
Fetzer, Susan Jane. Reducing the Pain of Venipuncture. J Perianesth Nurs 14 (2), 95-112. 4 1999.
Gadkar, et al. A novel method to perform genomic walks using a combination of single strand DNA circularization and rolling circle amplification. J Microbiol Methods. Oct. 2011;87(1):38-43. doi: 10.1016/j.mimet.2011.07.003. Epub Jul. 14, 2011.
Gay, et al. Accuracy of a filter paper method for measuring glycosylated hemoglobin. Diabetes Care. Jan. 1992;15(1):108-10.
Goodhousekeeping.com. Stain Buster—Blood. 2007, accessed May 25, 2015. URL:<http://www.goodhousekeeping.com/stain-buster/>.
Guthrie, et al. A Simple Phenylalanine Method for Detecting Phenylketonuria in Large Populations of Newborn Infants. Pediatrics. Sep. 1963;32:338-43.
Hewitt, et al. Tissue handling and specimen preparation in surgical pathology: issues concerning the recovery of nucleic acids from formalin-fixed, paraffin-embedded tissue. Arch Pathol Lab Med. Dec. 2008;132(12):1929-35. doi: 10.1043/1543-2165-132.12.1929. http://www.whatman.com/DMPK.aspx and FTA DMPK Card Selection. 2017. URL:<http://www.gelifesciences.com/webapp/wcs/stores/servlet/CategoryDisplay?categoryId=104363&catalogId=10101&productId=&top=Y&storeId=11787&langId=-1 >.
Hu, et al. Validation and Modification of Dried Blood Spot-Based Glycosylated Hemoglobin Assay for the Longitudinal Aging Study

(56) References Cited

OTHER PUBLICATIONS in India. Am J Hum Biol. Jul. 8, 2015; 27(4): 579-581. Published online Dec. 3, 2014. doi: 10.1002/ajhb.22664.
International Preliminary Report on Patentability dated Jan. 26, 2016 for International PCT Patent Application No. PCT/US2014/047953.
International Search Report and Written Opinion dated Jan. 29, 2014 for International PCT Patent Application No. PCT/US2013/065821.
International Search Report and Written Opinion dated Jun. 19, 2015 for International PCT Patent Application No. PCT/EP2015/058518.
International Search Report and Written Opinion dated Jul. 10, 2015 for International PCT Patent Application No. PCT/US2014/062570.
International Search Report and Written Opinion dated Sep. 6, 2013 for International PCT Patent Application No. PCT/US2013/038576.
International Search Report and Written Opinion dated Nov. 6, 2014 for International PCT Patent Application No. PCT/US2014/047953.
International Search Report and Written Opinion dated Dec. 19, 2014 for International PCT Patent Application No. PCT/EP2014/067453.
International Search Report dated Mar. 4, 2013 for International PCT Application No. PCT/SE2012/051168.
Invitation to Respond to Written Opinion dated Nov. 21, 2016 for Singaporean Patent Application No. SG11201600615V.
Invitation to Respond to Written Opinion dated Dec. 19, 2016 for Singaporean Patent Application No. SG11201601114P.
Jeppsson, et al. Capillary blood on filter paper for determination of HbA1c by ion exchange chromatography. Diabetes Care. Feb. 1996;19(2):142-5.
Jones, et al. Analysis of Hemoglobin A1c from Dried Blood Spot Samples with the Tina-quant® II Immunoturbidimetric Method.J Diabetes Sci Technol. Mar. 2010; 4(2): 244-249. Published online Mar. 1, 2010. doi: 10.1177/193229681000400203.
King, et al. The UK Prospective Diabetes Study (UKPDS): clinical and therapeutic implications for type 2 diabetes. Br J Clin Pharmacol. Nov. 1999; 48(5): 643-648. doi: 10.1046/j.1365-2125.1999.00092.x.
Kuhn, et al. Template-independent ligation of single-stranded DNA by T4 DNA ligase. FEBS J. Dec. 2005;272(23):5991-6000.
Kumar, et al. Inhibition of mammalian ribonucleases by endogenous adenosine dinucleotides. 2003, Biochemical and Biophysical Research Communications 300 ,pp. 81-86.
Lam, et al. EDTA is a better anticoagulant than heparin or citrate for delayed blood processing for plasma DNA analysis. Clin Chem. Jan. 2004;50(1):256-7.
Li, et al. Kinetics of RNA degradation by specific base catalysis of transesterification involving the 2'-hydroxyl group. Journal American Chemistry Society, 1999, 121 (23), pp. 5364-5372.
Li, et al. Whole Genome Amplification of Plasma-Circulating DNA Enables Expanded Screening for Allelic Imbalance in Plasma. J Mol Diagn. Feb. 2006; 8(1): 22-30. doi: 10.2353/jmoldx.2006.050074.
Little, et al. Collection of blood on filter paper for measurement of glycated hemoglobin by affinity chromatography. Clin Chem. May 1986;32(5):869-71.
Lloyd, et al. Formula Tolerance in Postbreastfed and Exclusively Formula-fed Infants. Pediatrics. Jan. 1999, vol. 103, Issue 1.
Mastronardi, et al. The use of dried blood spot sampling for the measurement of HbA1 c: a cross-sectional study. BMC Clinical Pathology, Jul. 8, 2015, 15:13. DOI: 10.1186/s12907-015-0013-5.
Matsubara, et al. Dried blood spot on filter paper as a source of mRNA. Nucleic Acids Research, vol. 20, Issue 8, Apr. 25, 1992. p. 1998, 1 page.
McDade, et al. What a drop can do: dried blood spots as a minimally invasive method for integrating biomarkers into population-based research. Demography. Nov. 2007;44(4):899-925.
McDade. What a drop. Demography. Nov. 2007; 44(4): 899-925.
Mollmann, et al. The stability of insulin in solid formulations containing melezitose and starch. Effect of processing and excipients. Drug Development and Industrial Pharmacy, vol. 32, No. 6, 01-Jun. 2006, 7 pages.
Nakamoto, et al. Detection of Tumor DNA in Plasma Using Whole Genome Amplification. Bulletin of Tokyo Dental College, Jan. 2006, vol. No. 47, Issue No. 3, pp. 125-131.
Natarajan, et al. Paper-based archiving of mammalian and plant samples for RNA analysis. BioTechniques, 2000, 29 pp. 1328-1333.
Nathan, et al. Intensive Diabetes Treatment and Cardiovascular Disease in Patients with Type 1 Diabetes. N Engl J Med, Dec. 22, 2005; 353:2643-2653. DOI: 10.1056/NEJMoa052187.
Notice of Allowance dated Apr. 22, 2015 for U.S. Appl. No. 13/721,948.
Notice of Allowance dated Apr. 22, 2015 for U.S. Appl. No. 13/968,497.
Notice of Allowance dated Apr. 23, 2015 for U.S. Appl. No. 13/460,076.
Notice of Allowance dated Sep. 22, 2016 for U.S. Appl. No. 14/068,633.
Notice of Allowance dated Sep. 23, 2016 for U.S. Appl. No. 14/261,900.
Notice of Allowance dated Dec. 9, 2016 for U.S. Appl. No. 13/952,173.
Notice of Allowance dated Dec. 17, 2014 for U.S. Appl. No. 13/460,076.
Notice of Allowance dated Dec. 17, 2014 for U.S. Appl. No. 13/968,497.
Notification of Reasons for Refusal dated Feb. 7, 2017 for Japanese Patent Application No. JP2015-510354.
Nunez, et al. Application of Circular Ligase to Provide Template for Rolling Circle Amplification of Low Amounts of Fragmented DNA. The Nineteenth International Symposium on Human Identification, 2008, 7 pages.
Office Action dated Jan. 6, 2016 for U.S. Appl. No. 13/985,089.
Office Action dated Feb. 24, 2017 for U.S. Appl. No. 13/985,089.
Office Action dated Apr. 10, 2015 for U.S. Appl. No. 14/355,027.
Office Action dated Apr. 18, 2016 for U.S. Appl. No. 14/355,027.
Office Action dated Apr. 30, 2015 for U.S. Appl. No. 13/952,173.
Office Action dated May 23, 2014 for U.S. Appl. No. 13/460,076.
Office Action dated Jun. 3, 2016 for U.S. Appl. No. 14/068,633.
Office Action dated Jun. 3, 2016 for U.S. Appl. No. 14/261,900.
Office Action dated Jun. 5, 2014 for U.S. Appl. No. 13/721,948.
Office Action dated Jun. 5, 2014 for U.S. Appl. No. 13/968,497.
Office Action dated Jun. 6, 2017 for U.S. Appl. No. 15/285,986.
Office Action dated Jun. 18, 2015 for U.S. Appl. No. 13/985,089.
Office Action dated Jul. 14, 2016 for U.S. Appl. No. 13/952,173.
Office Action dated Sep. 6, 2016 for U.S. Appl. No. 14/355,027.
Office Action dated Oct. 8, 2015 for U.S. Appl. No. 13/952,173.
Office Action dated Oct. 13, 2015 for U.S. Appl. No. 14/355,027.
Office Action dated Oct. 28, 2014 for U.S. Appl. No. 13/460,076.
Office Action dated Oct. 29, 2014 for U.S. Appl. No. 13/721,948.
Office Action dated Oct. 29, 2014 for U.S. Appl. No. 13/968,497.
Office Action dated Nov. 12, 2015 for U.S. Appl. No. 14/068,633.
Office Action dated Dec. 17, 2015 for U.S. Appl. No. 14/261,900.
Rohlfing, et al. Defining the relationship between plasma glucose and HbA(1c): analysis of glucose profiles and HbA(1c) in the Diabetes Control and Complications Trial. Diabetes Care. Feb. 2002;25(2):275-8.
Sambrook, et al. Molecular Cloning: a Laboratory Manual. 2nd edition. Cold Spring Harbor, New York, Cold Spring Harbor Laboratory Press, Dec. 1989, vol. 1, p. 7.2, 7.3, 7.4 and 7.5.
Senese, Fred. What is cellulose? General Chemistry Online. Accessed Jun. 1, 2015. URL:< http://antoine.frostburg.edu/chem/senese/101/consumer/faq/what-is-cellulose.shtml>.
Shaklai, et al. Nonenzymatic glycosylation of human serum albumin alters its conformation and function. J Biol Chem. Mar. 25, 1984;259(6):3812-7.
Shore, et al. DNA flexibility studied by covalent closure of short fragments into circles, Proc Natl Acad Sci U S A. Aug. 1981;78(8):4833-7.

(56) References Cited

OTHER PUBLICATIONS

Shore, et al. Energetics of DNA twisting. I. Relation between twist and cyclization probablity, J Mol Biol. Nov. 15, 1983;170(4):957-81.
Shuman, Stewart. DNA ligases: progress and prospects, J Biol Chem. Jun. 26, 2009;284(26):17365-9. doi: 10.1074/jbc.R900017200. Epub Mar. 27, 2009.
SMIT. Polymer Size. Macromolecules. 1992; 25(13):3585-3590.
Tan, et al. DNA, RNA, and Protein Extraction: The Past and The Present. Journal of Biomedicine and Biotechnology, 2009, pp. 1-10.
Tate, et al. Evaluation of circular DNA substrates for whole genome amplification prior to forensic analysis. Forensic Science International: Genetics. vol. 6, Issue 2, Mar. 2012, pp. 185-190.
The Diabetes Control and Complications Trial Research Group. The Effect of Intensive Treatment of Diabetes on the Development and Progression of Long-Term Complications in Insulin-Dependent Diabetes Mellitus. N Engl J Med 1993; 329:977-986. Sep. 30, 1993. DOI:10.1056/NEJM199309303291401.
Torchia, et al. Archaeal RNA ligase is a homodimeric protein that catalyzes intramolecular ligation of single-stranded RNA and DNA. Nucleic Acids Res. Nov. 2008;36(19):6218-27. doi: 10.1093/nar/gkn602. Epub Oct. 1, 2008.
Wang, et al. Balanced-PCR amplification allows unbiased identification of genomic copy changes in minute cell and tissue samples. Nucleic Acids Res. 2004; 32(9): e76. Published online May 21, 2004. doi: 10.1093/nar/gnh070.
Weiss, et al. Ezymatic breakage and joining of deoxyribonucleic acid. VII. Properties of the enzyme-adenylate intermediate in the polynucleotide ligase reaction. J Biol Chern. Sep. 10, 1968;243(17):4556-63.
Written Opinion dated Dec. 19, 2016 for Singapore Patent Application No. SG11201601114P.
Xue, et al. Optimizing the yield and utility of circulating cell-free DNA from plasma and serum. Clin Chim Acta. Jun. 27, 2009;404(2):100-4. doi: 10.1016/j.cca.2009.02.018. Epub Mar. 10, 2009.
Zale, et al. Why does ribonuclease irreversibly inactivate at high temperatures? Biochemistry, 1986, 25 (19), pp. 5432-5444.
Zhang, et al. RNA analysis from newborn screening dried blood specimens. Human Genetics, vol. 89, Issue 3, May 1992, pp. 311-314.
Zhelkovsky, et al. Structure-function analysis of Methanobacterium thermoautotrophicum RNA ligase—engineering a thermostable ATP independent enzyme. BMC Mol Biol. Jul. 18, 2012;13:24. doi: 10.1186/1471-2199-13-24.
KUMAR.S et al., Novel Stabilizers from Saccharides for Lyophilized Formulation with Therapeutic Protein A Case Study, International Journal of Pharmaceutical Innovations, (2013), 3(3): 130-137.
AMBION. RNAqueousTM-4PCR Instruction Manual passage. RNAqueous-4PCR Instruction Manual, pp. 1-29, Apr. 18, 2002.
European Examination Report dated Oct. 25, 2017 for European Patent Application No. EP14752322.9, General Electric Company, 7 Pages.
European Office Action dated Jan. 24, 2018 for European Patent Application No. EP15717489.7, General Electric Company, 7 Pages.
Fernando, et al. A new methodology to preserve the original proportion and integrity of cell-free fetal DNA in maternal plasma during sample processing and storage. Prenat Diagn. May 2010;30(5):418-24. doi: 10.1002/pd.2484.
Fienniges, et al. Electron Beam Irradiation of Cellulosic Materials—Opportunities and Limitations. Materials, vol. No. 6, pp. 1584-1598, Apr. 29, 2013.
Granath, Kirsti A. Solution properties of balanced dextrans. Journal of Colloid Science. Aug. 1958; 13(4): pp. 308-328.
Hardin, et al. Whole genome microarray analysis, from neonatal blood cards. BMC Genet. Jul. 22, 2009;10:38. doi: 10.1186/1471-2156-10-38. 8 Pages.
Japanese Search Report dated Aug. 2, 2017 for Japanese Patent Application No. JP2015510354. 17 Pages.

Johanson, et al. DNA Elution from Buccal Cells Stored on Whatman FTA Classic Cards using a Modified Methanol Fixation Method. Biotechniques, vol. No. 46, Issue No. 4, pp. 309-311, Apr. 2009.
Johnson, et al. Improved Technique Utilizing Nonfat Dry Milk for Analysis of Proteins and Nucleic Acids Transferred to Nitrocellulose. Gene Analysis Techniques 1 (1):3-8. Jan. 1984. DOI: 10.1016/0735-0651 (84)90049-9.
JP Office Action for JP Application No. 2013-554907 dated Dec. 22, 2015 (2 pages).
Miles, et al. Improved Elution of DNA from Whatman FTA Cards Using PrepGEM/ForensicGEM Storage Card Extraction Kits. ZyGEM, Oct. 1, 2012. 2 Pages.
Miller, et al. Collection and laboratory methods for dried blood spots for hemoglobin A1c and total and high-density lipoprotein cholesterol in population-based surveys. Clin Chim Acta. May 20, 2015;445:143-54. doi: 10.1016/j.cca.2015.03.028. Epub Mar. 27, 2015.
Office Action dated Mar. 30, 2016 for U.S. Appl. No. 13/985,908. 9 Pages.
Office Action dated May 5, 2017 for U.S. Appl. No. 13/985,908. 11 Pages.
Office Action dated Jul. 17, 2015 for Chinese Patent Application No. CN201380022584.6. 20 Pages.
Office Action dated Sep. 9, 2015 for U.S. Appl. No. 13/985,908. 12 Pages.
Office Action dated Oct. 26, 2016 for U.S. Appl. No. 13/985,908. 13 Pages.
Sauer, et al. Single molecule DNA sequencing in submicrometer channels: state of the art and future prospects. Journal of Biotechnology. vol. 86, Issue 3, Apr. 13, 2001, pp. 181-201.
Wolfgramm, et al. Simplified Buccal DNA Extraction with FTA Elute Cards. Forensic Science International: Genetics, vol. No. 3, Issue No. 2, pp. 125-127, Mar. 1, 2009.
Written Opinion dated Apr. 7, 2017 for Singaporean Patent Application No. SG11201608021T. 7 Pages.
"Written Opinion dated Jul. 20, 2017 for Singaporean Patent Application No. SG11201608021T". 7 Pages.
Written Opinion dated Nov. 16, 2016 for Singaporean Patent Application No. SG11201601114P. 7 Pages.
Brockbank, William. The Ancient Art of Cupping. Journal of Chinese Medicine. No. 21, May 1986. Extracted from "Ancient Therapeutic Arts" 1954).
Co-pending U.S. Appl. No. 29/655,964, filed Jul. 9, 2018.
Co-pending U.S. Appl. No. 16/211,866, filed Dec. 6, 2018.
Harvey, et al. Impregnated 903 blood collection paper A tool for DNA preparation from dried blood spots for PCR amplification. 1995. Clinical Chemistry 41 (S6 Part 2): S108.
Hogan et al. Next-Generation Biospecimen Preservation at Ambient Temperature Based on the Use of Micron-Scale Scaffolds. integenX (Mar. 14, 2012). 21 slides.
Page, et al. The importance of careful blood processing in isolation of cell-free DNA. Ann N Y Acad Sci. Sep. 2006;1075:313-7.
PCT/EP2015/058518 International Preliminary Report on Patentability dated Oct. 25, 2016.
PCT/US2018/013223 International Search Report and Written Opinion dated May 31, 2018.
Sambrook, et al. Molecular Cloning: a Laboratory Manual. 2nd edition. Cold Spring Harbor, New York, Cold Spring Harbor Laboratory Press, Dec. 1989, vol. 1, p. 7.3, 7.4 and 7.5.
U.S. Appl. No. 15/285,986 Office Action dated Aug. 2, 2018.
U.S. Appl. No. 15/463,943 Office Action dated Jul. 27, 2018.
U.S. Appl. No. 15/285,986 Office Action dated Jan. 16, 2018.
Wang et al. Minimally invasive extraction of dermal interstitial fluid for glucose monitoring using microneedles. Diabetes Technol Ther. Feb. 2005;7(1):131-41.
Weigl et al. Point-of-Care Diagnostics in Low-Resource Settings and Their Impact on Care in the Age of the Noncommunicable and Chronic Disease Epidemic. J Lab Autom. Jun. 2014; 19(3):248-57.
Yan et al. Evaluation needle length and density of microneedle arrays in the pretreatment of skin fortransdermal drug delivery. Int J Pharm. May 31, 2010;391(1-2):7-12.
U.S. Appl. No. 15/285,986 Office Action dated Feb. 26, 2019.
U.S. Appl. No. 16/104,846 Office Action dated Feb. 27, 2019.

(56) References Cited

OTHER PUBLICATIONS

European Office Action dated Sep. 27, 2018 for European Patent Application No. EP15717489.7, 5 Pages.
PCT/US2018/013223 International Preliminary Report on Patentability dated Jul. 16, 2019.
U.S. Appl. No. 16/104,846 Office Action dated Jul. 19, 2019.
U.S. Appl. No. 15/285,986 Notice of Allowance dated Nov. 7, 2019.
U.S. Appl. No. 15/463,943 Office Action dated Oct. 15, 2019.
GB1615387.6 Office Action dated Jun. 14, 2019.
EP16845220.9 Extended European Search Report dated Apr. 18, 2019.
Co-pending U.S. Appl. No. 29/740,373, filed Jul. 2, 2020.
GB1911162.4 Office Action dated Dec. 17, 2019.
GB2000728.2 Office Action dated Jan. 28, 2020.
GB2008501.5 Office Action and Search Report dated Jun. 30, 2020.
U.S. Appl. No. 16/104,846 Notice of Allowance dated Feb. 24, 2020.
U.S. Appl. No. 15/285,986 Notice of Allowance dated Feb. 18, 2020.
U.S. Appl. No. 16/685,893 Office Action dated Feb. 4, 2020.
U.S. Appl. No. 16/685,954 Office Action dated Feb. 6, 2020.
U.S. Appl. No. 16/685,999 Office Action dated Feb. 4, 2020.
U.S. Appl. No. 16/685,999 Office Action dated Jul. 22, 2020.
U.S. Appl. No. 29/655,964 Notice of Allowance dated Apr. 15, 2020.
Vivid Plasma Separation Membrane. Product Data. PALL Life Sciences (Copyright 2009). 6 pages.
EP18738600.8 Extended European Search Report dated Sep. 23, 2020.
EP20175443.9 Extended European Search Report dated Nov. 19, 2020.
CN2016800651404 Office Action and Search Report dated Jan. 12, 2021 (wi partial English translation).
JP2018-512965 Office Action dated Aug. 3, 2020 (w/ English translation).
JP2018-512965 Office Action dated Mar. 31, 2021 (w/ English translation).
U.S. Appl. No. 29/740,373 Office Action dated Mar. 30, 2021.
U.S. Appl. No. 16/685,893 Notice of Allowance dated Nov. 24, 2020.
U.S. Appl. No. 16/685,893 Notice of Allowance dated Oct. 23, 2020.
U.S. Appl. No. 16/685,954 Office Action dated Oct. 21, 2020.
U.S. Appl. No. 16/685,999 Notice of Allowance dated Nov. 24, 2020.
U.S. Appl. No. 16/685,999 Notice of Allowance dated Oct. 21, 2020.
CN2016800651404 Office Action and Search Report dated Sep. 15, 2021 (w/ partial English translation).
CN201880006612.8 Office Action with Search Report dated Jul. 16, 2021 (w/ partial English translation).
EP18738600.8 Office Action dated Jul. 2, 2021.
GB2020581.1 Office Action dated Jul. 12, 2021.
GB2020581.1 Search Report dated Apr. 19, 2021.
GB2020582.9 Office Action and Search Report dated Apr. 19, 2021.
PCT/US2021/022631 International Search Report and Written Opinion dated Aug. 17, 2021.
U.S. Appl. No. 16/685,954 Office Action dated May 19, 2021.

\* cited by examiner

FIG. 7

| Applicable Tests |
|---|
| NMR LipoProfile w/IR Markers |
| Liver Fibrosis, Fibro Test-ActiTest Panel |
| Trimipramine, Serum |
| Imipramine and Desipramine, Serum |
| Desipramine, Serum |
| Nortriptyline, Serum |
| Doxepin and Nordoxepin, Serum |
| Amitriptyline and Nortriptyline, Serum |
| Tick-Borne Disease Antibodies Panel, Serum |
| Ehrlichia Antibody Panel, Serum |
| Clomipramine, Serum |
| Opiates, Serum or Plasma, Quantitative |
| Alpha-Globin Gene Analysis |
| ROMA (Risk of Ovarian Malignancy Algorithm) |
| Thiopurine Methyltransferase (TPMT), Erythrocytes |
| Bile Acids, Urine |
| VHL Gene, Full Gene Analysis |
| CASR Gene, Full Gene Analysis |
| SDHB Gene, Full Gene Analysis |
| SDHC Gene, Full Gene Analysis |
| SDHB, SDHC, SDHD Gene Panel |
| SDHD Gene, Full Gene Analysis |
| VHL Gene, Erythrocytosis Mutation Analysis |
| MGMT Promoter Methylation, Tumor |
| Rufinamide, Serum |
| Mucopolysaccharidosis IIIB, Full Gene Analysis |
| Hurler Syndrome, Full Gene Analysis |
| Mucopolysaccharidosis VI, Full Gene Analysis |
| Multiple Sulfatase Deficiency, Full Gene Analysis |
| UBE3A Gene, Full Gene Analysis |
| Very Long Chain Acyl-CoA Dehydrogenase Deficiency, Full Gene Analysis |
| Wilson Disease, Full Gene Analysis |
| FTCD Gene, Full Gene Analysis |
| Progranulin Gene (GRN), Full Gene Analysis |
| Tay-Sachs Disease, HEXA Gene, Full Gene Analysis |
| MAPT Gene, Sequence Analysis, 7 Exon Screening Panel |
| Medium-Chain Acyl-CoA Dehydrogenase (MCAD) Deficiency Full Gene Analysis |

| Applicable Tests |
|---|
| Methylmalonic Aciduria and Homocystinuria, cblC Type, Full Gene Analysis |
| Methylmalonic Aciduria and Homocystinuria, cblD Type, Full Gene Analysis |
| Mucopolysaccharidosis IIIA, Full Gene Analysis |
| Alanine:Glyoxylate Aminotransferase (AGXT) Mutation Analysis (G170R), Blood |
| CDKN1C Gene, Full Gene Analysis |
| Carnitine Palmitoyltransferase II Deficiency, Full Gene Analysis |
| Fabry Disease, Full Gene Analysis |
| Ferrochelatase (FECH) Gene, Full Gene Analysis |
| Pompe Disease, Full Gene Analysis |
| GALT Gene, Full Gene Analysis |
| MLH1 Gene, Full Gene Analysis |
| MSH2 Gene, Full Gene Analysis |
| MSH6 Gene, Full Gene Analysis |
| APC Gene, Full Gene Analysis |
| MLYCD Gene, Full Gene Analysis |
| MECP2 Gene, Full Gene Analysis |
| GNPTAB Gene, Full Gene Analysis |
| Niemann-Pick Type C Disease, Full Gene Analysis |
| PMS2 Gene, Full Gene Analysis |
| SEPT9 Gene, Mutation Screen |
| X-Linked Adrenoleukodystrophy, Full Gene Analysis |
| MLH1/MSH2 Genes, Full Gene Analysis |
| Biotinidase Deficiency, BTD Full Gene Analysis |
| Carnitine-Acylcarnitine Translocase Deficiency, Full Gene Analysis |
| CFTR Gene, Full Gene Analysis |
| Krabbe Disease, Full Gene Analysis and Large (30 kb) Deletion, PCR |
| Gaucher Disease, Full Gene Analysis |
| GRHPR Gene, Full Gene Analysis |
| HOXB13 Mutation Analysis (G84E) |
| Hunter Syndrome, Full Gene Analysis |
| AGXT Gene, Full Gene Analysis |
| Autosomal Recessive Polycystic Kidney Disease (ARPKD), Full Gene Analysis |
| ARSA Gene, Full Gene Analysis |

(Fig. 7 continued)

| Applicable Tests |
|---|
| Prader-Willi/Angelman Syndrome, Molecular Analysis |
| Chromosomal Microarray, Tumor, Fresh or Frozen using Affymetrix Cytoscan HD |
| Chromosomal Microarray, Autopsy, Products of Conception, or Stillbirth |
| Chromosomal Microarray, Tumor, FFPE |
| Duchenne/Becker Muscular Dystrophy DMD Gene, Large Deletion and Duplication Analysis |
| Hereditary Pancreatitis Panel |
| Familial Mutation, Targeted Testing |
| Newborn Aneuploidy Detection, FISH |
| Prenatal Aneuploidy Detection, FISH |
| Plasma Cell Proliferative Disorder (PCPD), FISH |
| Fragile X, Follow up Analysis |
| TNFRSF1A Gene, Full Gene Analysis |
| Beta-Globin Gene, Large Deletion/Duplication |
| Known 45,X, Mosaicism Reflex Analysis, FISH |
| RET Proto-Oncogene, Full Gene Analysis |
| Short-Chain Acyl-CoA Dehydrogenase (SCAD) Deficiency, Full Gene Analysis |
| Niemann-Pick Disease, Types A and B, Full Gene Analysis |
| MLH1 Hypermethylation Analysis, Blood |
| Beckwith-Wiedemann Syndrome (BWS)/Russell-Silver Syndrome (RSS) Molecular Analysis |
| C9orf72, Follow Up Analysis |
| Alveolar Rhabdomyosarcoma by Reverse Transcriptase PCR (RT-PCR) |
| Desmoplastic Small Round-Cell Tumor by Reverse Transcriptase PCR (RT-PCR) |
| Ewing Sarcoma, by Reverse Transcriptase PCR (RT-PCR) |
| Synovial Sarcoma by Reverse Transcriptase PCR (RT-PCR) |
| Mesenchymal Chondrosarcoma, by Reverse Transcriptase PCR (RT-PCR) |
| CTRC Gene, Full Gene Analysis |
| FLG Gene, Mutation Analysis |
| SPINK1 Gene, Full Gene Analysis |
| Microsatellite Instability (MSI)/Immunohistochemistry (IHC) Profile-Lynch/Hereditary Nonpolyposis Colorectal Cancer (HNPCC) Screen |
| Mismatch Repair (MMR) Protein Immunohistochemistry Only, Tumor |

| Applicable Tests |
|---|
| RAS/RAF Targeted Gene Panel by Next Generation Sequencing, Tumor |
| GNAQ/GNA11 Mutation Analysis, Uveal Melanoma |
| MLH1 Hypermethylation and BRAF Mutation Analysis, Tumor |
| MLH1 Hypermethylation Analysis, Tumor |
| Microsatellite Instability (MSI), Tumor |
| C9orf72 Hexanucleotide Repeat, Molecular Analysis |
| KRAS Mutation Analysis, 7 Mutation Panel, Colorectal |
| KRAS Mutation Analysis, 7 Mutation Panel, Other (Non-Colorectal) |
| EGFR Gene, Mutation Analysis, 29 Mutation Panel, Tumor |
| Lung Cancer, EGFR with ALK Reflex, Tumor |
| Birt-Hogg-Dube Syndrome, Full Gene Analysis |
| Specimen Source Identification |
| BRAF Mutation Analysis (V600E), Tumor |
| Hereditary Colon Cancer CGH Array |
| Slide Review in Molecular Genetics (Bill Only) |
| MLH-1, Immunostain (Bill Only) |
| MSH-2, Immunostain (Bill Only) |
| MSH-6, Immunostain (Bill Only) |
| PMS-2, Immunostain (Bill Only) |
| Spinobulbar Muscular Atrophy (Kennedy Disease), Molecular Analysis |
| BRAF Mutation Analysis (V600), Melanoma |
| Solid Tumor Targeted Cancer Gene Panel by Next Generation Sequencing |
| Beta-Catenin, Fibromatosis, Mutation Analysis |
| MEFV Gene, Full Gene Analysis |
| PRSS1 Gene, Full Gene Analysis |
| BRAF Analysis (Bill Only) |
| MLH1 Hypermethylation Analysis (Bill Only) |
| IDH1/2, Mutation Analysis |
| FOXL2, Granulosa Cell Tumor, c.402C->G Mutation Analysis |
| Melanoma Targeted Gene Panel by Next Generation Sequencing, Tumor |
| GIST Targeted Gene Panel by Next Generation Sequencing, Tumor |
| PTEN Gene, Full Gene Analysis |
| SMAD4 Gene, Full Gene Analysis |
| STK11 Gene, Full Gene Analysis |
| Mucopolysaccharidosis IIID, Full Gene Analysis |
| PDGFRA Exon 18, Mutation Analysis |

(Fig. 7 continued)

| Applicable Tests |
|---|
| PDGFRA Exon 14, Mutation Analysis |
| PDGFRA Exon 12, Mutation Analysis |
| KIT Exon 17, Mutation Analysis |
| KIT Exon 13, Mutation Analysis |
| Bloom Syndrome, Mutation Analysis, 2281 delATCTGAinsTAGATTC (2281del6/ins7) |
| TTR Gene, Full Gene Analysis |
| Apolipoprotein A-II (APOA2) Gene, Full Gene Analysis |
| Apolipoprotein A-I (APOA1) Gene, Full Gene Analysis |
| MLH3 Gene, Full Gene Analysis |
| TP53 Gene, Full Gene Analysis |
| Acute Porphyria, Multi-Gene Panel |
| PPOX Gene, Full Gene Analysis |
| Chromosome Analysis, Sister Chromatid Exchange (SCE) for Bloom Syndrome, Blood |
| Gaucher Disease, Mutation Analysis, GBA |
| Lysozyme (LYZ) Gene, Full Gene Analysis |
| Gelsolin (GSN) Gene, Full Gene Analysis |
| Familial Dysautonomia, Mutation Analysis, IVS20(+6T->C) and R696P |
| Fanconi Anemia C Mutation Analysis, IVS4(+4)A->T and 322delG |
| Canavan Disease, Mutation Analysis, ASPA |
| Hereditary Colon Cancer Multi-Gene Panel |
| CPOX Gene, Full Gene Analysis |
| CHEK2 Gene, Full Gene Analysis |
| Chromosomal Microarray, Prenatal, Amniotic Fluid/Chorionic Villus Sampling |
| Chromosomal Microarray, Hematologic Disorders |
| Steroid Sulfatase Deficiency, Xp22.3 Deletion, FISH |
| Myeloma, FISH, Fixed Cells |
| Chromosome Analysis, Autopsy, Products of Conception, or Stillbirth |
| CHIC2 (4q12) Deletion (FIP1L1 and PDGFRA Fusion), FISH |
| XX/XY in Opposite Sex Bone Marrow Transplantation, FISH |
| Mayo Stratification for Myeloma and Risk-Adapted Therapy Report |
| Hematologic Disorders, Fluorescence In Situ Hybridization (FISH) Hold, Bone Marrow or Peripheral Blood |
| Hematologic Disorders, Chromosome Hold, Bone Marrow or Peripheral Blood |

| Applicable Tests |
|---|
| Chromosome Analysis, Rearrangement in Ataxia Telangiectasia, Blood |
| AXIN2 Gene, Full Gene Analysis |
| BMPR1A Gene, Full Gene Analysis |
| CDH1 Gene, Full Gene Analysis |
| Dentatorubral-Pallidoluysian Atrophy (DRPLA) Gene Analysis |
| Isovaleryl-CoA Dehydrogenase (IVD) Mutation Analysis (A282V) |
| Y Chromosome Microdeletions, Molecular Detection |
| Chromosomal Microarray, Congenital, Blood |
| Chromosomal Microarray (CMA) Familial Testing, FISH |
| Parental Sample Prep for Prenatal Microarray Testing |
| Uniparental Disomy |
| HMBS Gene, Full Gene Analysis |
| MYH Gene Analysis for Multiple Adenoma, Y165C and G382D |
| Alpha-Globin Gene Analysis |
| Huntington Disease, Molecular Analysis |
| Fibrinogen Alpha-Chain (FGA) Gene, Full Gene Analysis |
| Apolipoprotein E Genotyping, Blood |
| Lung Cancer, ALK (2p23) Rearrangement, FISH, Tissue |
| Melanoma, FISH, Tissue |
| FGFR1 (8p11.2) Amplification, FISH, Tissue |
| MDM2 (12q15) Amplification, Well-Differentiated Liposarcoma/Atypical Lipomatous Tumor, FISH, Tissue |
| Medulloblastoma, FISH, Tissue |
| MET (7q31), FISH, Tissue |
| Zygosity Testing (Multiple Births) |
| DNA Extraction, Metabolic Hematolog |
| Synovial Sarcoma (SS), 18q11.2 (SS18 or SYT) Rearrangement, FISH, Tissue |
| Products of Conception (POC) Aneuploidy Detection, FISH, Paraffin-Embedded Tissue |
| Angiosarcoma, MYC (8q24) Amplification, FISH, Tissue |
| 1p/19q Deletion in Gliomas, FISH, Tissue |
| HER2 Amplification Associated with Gastroesophageal Cancer, FISH, Tissue |
| HER2 Amplification, Miscellaneous Tumor, FISH, Tissue |

(Fig. 7 continued)

| Applicable Tests |
|---|
| HER2 Amplification Associated with Urothelial Carcinoma, FISH, Tissue |
| HER2 Amplification Associated with Breast Cancer, FISH, Tissue |
| Fragile X Syndrome, Molecular Analysis |
| Hemochromatosis HFE Gene Analysis, Blood |
| Mucolipidosis IV, Mutation Analysis, IVS3(-2)A->G and del6.4kb |
| Niemann-Pick Disease, Types A and B, Mutation Analysis |
| Tay-Sachs Disease, Mutation Analysis, HEXA |
| Galactosemia Gene Analysis (14-Mutation Panel) |
| Maternal Cell Contamination, Molecular Analysis |
| DNA Analysis, Blood |
| Peripheral T-Cell Lymphoma (PTCL), TP63 (3q28) Rearrangement, FISH, Tissue |
| Endometrial Stromal Tumors (EST), 7p15 (JAZF1), 6p21.32 (PHF1), 17p13.3 (YWHAE) Rearrangement, FISH, Tissue |
| T-Cell Lymphoma, FISH, Tissue |
| Ashkenazi Jewish Mutation Analysis Panel Without Cystic Fibrosis (CF) |
| Cystic Fibrosis Mutation Analysis, 106-Mutation Panel |
| 22q11.2 Deletion/Duplication, FISH |
| Williams Syndrome, 7q11.23 Deletion, FISH |
| Alveolar Soft Part Sarcoma (ASPS)/Renal Cell Carcinoma (RCC), Xp11.23 (TFE3), FISH, Tissue |
| PDGFRB/TEL Translocation (5;12) for Chronic Myelomonocytic Leukemia (CMML), FISH |
| BCR/ABL1 Translocation (9;22), FISH |
| 15q Deletion, Type I and Type II Characterization, Prader-Willi/Angelman Syndromes, FISH |
| X and Y Aneuploidy Detection, Buccal Smear, FISH |
| Chromosome Analysis, Amniotic Fluid |
| Chromosome Analysis, Body Fluid |
| Chromosome Analysis, Chorionic Villus Sampling |
| Chromosome Analysis, Lymphoid Tissue |
| Chromosome Analysis, Solid Tumors |
| Chromosome Analysis, Skin Biopsy |
| Amniotic Fluid Culture for Genetic Testing |
| Fibroblast Culture for Genetic Testing |

| Applicable Tests |
|---|
| 15q11.2 Duplication, FISH |
| Ewing Sarcoma (EWS), 22q12 (EWSR1) Rearrangement, FISH, Tissue |
| B-Cell Lymphoma, FISH, Tissue |
| MAML2 (11q21) Rearrangement, Mucoepidermoid Carcinoma (MEC), FISH, Tissue |
| PDGFB (22q13), Dermatofibrosarcoma Protuberans/Giant Cell Fibroblastoma, FISH, Tissue |
| USP6 (17p13), Aneurysmal Bone Cyst and Nodular Fasciitis, FISH, Tissue |
| Lung Cancer, RET (10q11) Rearrangement, FISH, Tissue |
| Plasma Cell Proliferative Disorder, FISH, Tissue |
| Myeloid Sarcoma, FISH, Tissue |
| Cutaneous Anaplastic Large Cell Lymphoma, 6p25.3 (DUSP22 or IRF4) Rearrangement, FISH, Tissue |
| Germ Cell Tumor (GCT), Isochromosome 12p, FISH, Tissue |
| Low-Grade Fibromyxoid Sarcoma (LGFMS), 16p11.2 (FUS or TLS) Rearrangement, FISH, Tissue |
| Alveolar Rhabdomyosarcoma (ARMS), 13q14 (FOXO1 or FKHR) Rearrangement, FISH, Tissue |
| Subtelomeric Region Anomalies, FISH |
| Wolf-Hirschhorn Syndrome, 4p16.3 Deletion, FISH |
| X-Inactivation (XIST), Xq13.2 Deletion, FISH |
| Uveal Melanoma, Chromosome 3 Monosomy, FISH, Tissue |
| MYB (6q23) Rearrangement FISH, Tissue |
| Lung Cancer, ROS1 (6q22) Rearrangement, FISH, Tissue |
| Chromosome Analysis, Hematologic Disorders, Blood |
| Smith-Magenis/Potocki-Lupski Syndromes, 17p11.2 Deletion/Duplication, FISH |
| Kallmann Syndrome, Xp22.3 Deletion, FISH |
| Miller-Dieker Syndrome, 17p13.3 Deletion, FISH |
| 1p36.3 Microdeletion Syndrome, FISH |
| Products of Conception (POC) Aneuploidy Detection, FISH, Fresh Tissue |
| Sex-Determining Region Y, Yp11.3 Deletion, FISH |

(Fig. 7 continued)

| Applicable Tests |
|---|
| Cri-du-chat, 5p Deletion, FISH |
| Chromosome Analysis, Hematologic Disorders, Bone Marrow |
| Chromosome Analysis, Congenital Disorders, Blood |
| Small Lymphocytic Lymphoma, FISH, Tissue |
| Sex Chromosome Determination, FISH, Tissue |
| Myxoid/Round Cell Liposarcoma, 12q13 (DDIT3 or CHOP) Rearrangement, FISH, Tissue |
| Neuroblastoma, 2p24 (MYCN) Amplification, FISH |
| Inflammatory Myofibroblastic Tumors (IMT), 2p23 (ALK) Rearrangement, FISH, Tissue |
| FGFR1 (8p11.2) Rearrangement, FISH |
| Imatinib Mesylate Responsive Genes, FISH |
| Neuroblastoma, 2p24 (MYCN) Amplification, FISH, Blood or Bone Marrow |
| B-Cell Acute Lymphoblastic Leukemia (B-ALL), FISH |
| UroVysion for Detection of Bladder Cancer, Urine |
| Circulating Tumor Cells (CTC) for Prostate Cancer by CellSearch, Blood |
| Circulating Tumor Cells (CTC) for Colorectal Cancer by CellSearch, Blood |
| Circulating Tumor Cells (CTC) for Breast Cancer by CellSearch, Blood |
| T-Cell Acute Lymphoblastic Leukemia (T-ALL), FISH |
| Myelodysplastic Syndrome (MDS), FISH |
| T-Cell Lymphoma, FISH, Blood or Bone Marrow |
| Chronic Lymphocytic Leukemia (CLL), FISH |
| B-Cell Lymphoma, FISH, Blood or Bone Marrow |
| Acute Myeloid Leukemia (AML), FISH |
| KIT Exon 8, Mutation Analysis |
| KIT Exon 11, Mutation Analysis |
| KIT Exon 9, Mutation Analysis |
| Insulin, Free and Total, Serum |
| Oxysterols, Blood Spots |
| Hypersensitivity Pneumonitis IgG Antibodies, Serum |
| Thermoactinomyces vulgaris, IgG Antibodies, Serum |
| Adenosine Deaminase, Pericardial Fluid |
| Adenosine Deaminase, Peritoneal Fluid |
| Adenosine Deaminase, Pleural Fluid |

| Applicable Tests |
|---|
| Lipoprotein-Associated Phospholipase A2 Activity, Serum |
| Phospholipase A2 Receptor Antibodies, Serum |
| Phospholipase A2 Receptor, Enzyme Linked Immunosorbent Assay, Serum |
| Phospholipase A2 Receptor, Indirect Immunofluorescence Assay, Serum |
| OncoHeme Next Generation Sequencing (NGS), Hematologic Neoplasms |
| Anaplasma phagocytophilum (Human Granulocytic Ehrlichiosis) Antibody, Serum |
| Trichrome Water Soluble Stain (Bill Only) |
| Muscle Consult, Outside Slide (Bill Only) |
| Muscle Consult, w/USS Prof (Bill Only) |
| Muscle Consult, w/Complex Rvw of Hx (Bill Only) |
| Muscle Consult, w/Slide Prep (Bill Only) |
| NADH Dehydrogenase Stain (Bill Only) |
| Oil Red O Stain (Bill Only) |
| Periodic Acid-Schiff Stain (Bill Only) |
| Phosphorylase Stain (Bill Only) |
| Succinic Dehydrogenase Stain (Bill Only) |
| TB ATPase Stain (Bill Only) |
| Acid Phosphatase Stain (Bill Only) |
| Alizarin Red Stain (Bill Only) |
| Alpha-Naphthyl Stain (Bill Only) |
| Acetate Non-Specific Esterase Stain (Bill Only) |
| ATPase Acid Alkaline Stain (Bill Only) |
| Congo Red Stain (Bill Only) |
| Cytochrome Oxidase Stain (Bill Only) |
| Muscle, Level IV Consult (Bill Only) |
| Alpha-Glycerophosphate Stain (Bill Only) |
| PAS Diastase Stain (Bill Only) |
| Phosphofructokinase Stain |
| Lactate Dehydrogenase Stain |
| Aldolase Stain |
| AMP Deaminase ST |
| HIV-1 RNA Quantification, Plasma |
| Phospholipase A2 Receptor (PLA2R) Immunofluorescent Stain, Renal |
| Barbiturates, Screen, Urine |
| Caffeine, Serum |
| Valproic Acid, Free, Serum |
| Valproic Acid, Free and Total, Serum |
| Benzodiazepines, Screen, Urine |
| Amikacin, Trough, Serum |
| Amikacin, Peak, Serum |
| Amikacin, Random, Serum |

(Fig. 7 continued)

| Applicable Tests |
|---|
| Carbamazepine-10,11-Epoxide, Serum |
| Carbamazepine Profile, Serum |
| Procainamide and N-acetylprocainamide, Serum |
| N-acetylprocainamide, Serum |
| Carbamazepine, Free, Serum |
| Carbamazepine, Free and Total, Serum |
| Ethanol, Screen, Urine |
| Procainamide plus NAPA, Serum |
| Amphetamines, Screen, Urine |
| Ethanol, Serum |
| Cocaine, Screen, Urine |
| Phenytoin, Total and Free, Serum |
| Phenytoin, Total and Phenobarbital Group, Serum |
| Phenytoin, Free, Serum |
| Primidone, Serum |
| Primidone and Phenobarbital, Serum |
| Ethosuximide, Serum |
| Lidocaine, Serum |
| Quinidine, Serum |
| Tetrahydrocannabinol, Screen, Urine |
| Phencyclidine, Screen, Urine |
| Opiates, Screen, Urine |
| Methotrexate, Serum |
| Gentamicin, Random, Serum |
| Vancomycin, Peak, Serum |
| Vancomycin, Trough, Serum |
| Vancomycin, Random, Serum |
| Tobramycin, Trough, Serum |
| Valproic Acid, Total, Serum |
| Tobramycin, Peak, Serum |
| Salicylate, Serum |
| Tobramycin, Random, Serum |
| Theophylline, Serum |
| Gentamicin, Trough, Serum |
| Lithium, Serum |
| Phenytoin, Total, Serum |
| Gentamicin, Peak, Serum |
| Carbamazepine, Total, Serum |
| Phenobarbital, Serum |
| HIV-1 RNA Quantification with Reflex to HIV-1 Genotypic Drug Resistance, Plasma |
| Acetaminophen, Serum |
| HIV-1 RNA Detection and Quantification, Plasma |
| HIV-1 Genotypic Protease and Reverse Transcriptase Inhibitor Drug Resistance, Plasma |
| Diphtheria Toxoid IgG Antibody, Serum |

| Applicable Tests |
|---|
| Tetanus Toxoid IgG Antibody, Serum |
| Diphtheria/Tetanus Antibody Panel, Serum |
| Methadone and Metabolites, Serum |

SYSTEMS, METHODS, AND DEVICES FOR SAMPLE COLLECTION, STABILIZATION AND PRESERVATION

CROSS-REFERENCE

The present application claims priority to U.S. provisional patent application No. 62/216,312, filed Sep. 9, 2015; and claims priority to U.S. provisional patent application No. 62/260,172, filed Nov. 25, 2015; and claims priority to U.S. provisional patent application No. 62/367,056, filed on Jul. 26, 2016; and claims priority to U.S. provisional patent application No. 62/368,817, filed on Jul. 29, 2016; the entire disclosures of which are incorporated herein by reference.

BACKGROUND OF THE INVENTION

Medical diagnostic tests can save lives; unfortunately they are not readily available to everyone. The growing costs of healthcare and availability of treatment can make it difficult for individuals around the world to receive adequate treatment. Having a simple blood panel done can require multiple visits to a medical doctor, first for blood collection then a follow up consultation or additional tests. The rising tangible costs of healthcare can be an additional deterrent; many patients cannot afford the time and cost of multiple visits to a doctor, and can put off tests until they experience symptoms that require medical treatment. New treatment paradigms can address the needs of the patient by reducing the time, cost and availability burdens. Improving patient access to diagnostics can improve the likelihood that tests will be conducted before symptoms appear which in turn can result in patients receiving treatment far earlier than previously possible. Early detection can facilitate early treatment, which in turn can ensure a better prognosis for the patient and an overall reduction in the cost of treatment.

Provided herein are improved solutions to enable a patient to collect, prepare, store, detect and analyze their own blood samples without the assistance of a medical practitioner or access to a medical facility.

SUMMARY OF THE INVENTION

The present invention generally relates to medical systems, devices and methods, and more particularly relates to a system and methods for user-mediated collection, separation, and stabilization of a blood sample. Specifically, the herein disclosed system, device and methods provide for an integrated device comprising a sample acquisition component, a sample separation component and a blood stabilization component incorporated within an integrated device configured to collect blood from a subject upon actuation, and stabilize the blood for further processing within or outside the device.

These and other embodiments are described in further detail in the following description related to the appended drawing figures.

In one aspect, a method is disclosed. The method involves deploying a sample acquisition and stabilization system with a tag to a subject wherein the system includes a blood collection unit configured for collecting a blood sample from the subject, an optional separation module for separating one or more components from the collected blood sample, and a stabilization matrix configured for stabilizing the one or more components from the collected blood sample wherein the tag comprises a label associated with an assay. The method further involves collecting the deployed tagged sample acquisition and stabilization system, performing one or more assays on the one or more stabilized components based on the tag, and providing a report on the one or more assays performed. The method can further involve separating the stabilization matrix from the system prior to one of the aforementioned method steps. The tag can be on the stabilization matrix. Optionally, when the separation module is present, the tag can be on the optional separation module. The stabilization matrix can be configured to perform multiple assays. The method can further involve identifying stabilized bio-components within the blood sample based on the tag present in a deployed sample acquisition and stabilization system and from that identification determining a stabilized component-specific assay to perform. The sample acquisition and stabilization system can be labeled with an RFID transmitter, a color label, a barcode, or a second label that differs from the sample tag.

In another aspect, a method for performing analysis on one or more bio-components from a bio-sample from a subject is disclosed. The method involves obtaining a sampling device which includes a sample acquisition component and a stabilization matrix which includes one or more stabilizing reagents configured to selectively stabilize at least one bio-component selected from the group consisting of: RNA, DNA, and protein. The method further involves performing one or more assays on the at least one stabilized bio-component in or on the sampling device at a location remote from one of the above-mentioned method steps. The one or more stabilization reagents can be disposed on or are integrated with a solid matrix and are in a substantially dry state. The solid matrix can be configured to substantially stabilize RNA for at least 11 days at 37 degrees Celsius. The assays performed in or on the device can include one or more of: PCR, DNA sequencing, RNA expression analysis, and RT-PCR.

In another aspect a method for performing analysis on one or more bio-components from a bio-sample from a subject is disclosed. The method involves obtaining a sampling device which includes a sample acquisition component and a stabilization matrix which includes one or more stabilizing reagents configured to selectively stabilize one or more bio-components selected from the group consisting of: RNA, DNA, and protein. The method further involves removing from the sampling device the stabilization matrix with the one or more bio-components; and performing one or more assays on the stabilization matrix. The stabilization matrix can be removed from the sampling device at a location remote from where one of the above-mentioned steps is carried out.

In another aspect, a method is disclosed which involves receiving, under ambient conditions, a substantially dry solid matrix comprising one or more stabilization reagents that selectively stabilize one or more bio-components selected from the group consisting of: DNA, RNA and protein, and performing one or more assays directly off of the dry solid matrix for analyzing the one or more selectively stabilized bio-components. The stabilization reagent can include a solid substrate comprising melezitose under a substantially dry state with water content of less than 2%. The stabilization reagent can be coupled to a sample acquisition component which includes a solid matrix for extraction and storage of nucleic acids from the biological sample, wherein the solid matrix has an RNA Integrity Number (RIN) of at least 4.

In another aspect, a device for point-of-care or self-administered collection and stabilization of a bio-sample is disclosed and embodiments are illustrated herein. The device includes a sample acquisition component comprising a body and a plunger, wherein the body comprises a proximal end, a distal end, an outer body surface extending between the proximal and distal ends, a base comprising at least one aperture and attached to the distal end, and a lumen defined within the body surface, wherein the plunger is disposed within the lumen, wherein the plunger comprises a proximal end, a distal end, and at least one needle connected to either end, wherein the at least one needle is configured to pass through the at least one aperture in the base when the plunger is actuated. The device includes a sample stabilization component which includes a reagent and a substrate configured such that components of a bio-sample are extracted and stabilized as the bio-sample migrates through the matrix from a point of collection; wherein the sample stabilization component is disposed within the lumen of the body such that actuation of the plunger drives the bio-sample through the matrix to further facilitate separation of the bio-sample.

In another aspect, a kit for collecting and stabilizing a sample is disclosed. The kit includes a sample acquisition component with one or more piercing elements configured for penetrating skin to expose blood, and a sample stabilization component, wherein the sample stabilization component comprises a solid substrate comprising melezitose under a substantially dry state. The solid substrate can include one or more of a lysis reagent and a biomolecule stabilizing reagent. Optionally, the melezitose can be present at a concentration in a range of 10 to 30%. The solid substrate can be configured for preserving enzyme activity. The kit can further include a plasma separation component.

In another aspect, a kit for collecting and stabilizing a biological sample is disclosed. The kit includes a sample acquisition component with one or more piercing elements configured for penetrating skin to expose blood, and a sample stabilization component comprising a solid matrix for selectively stabilizing one or more of the following bio-components: RNA, DNA, and protein. The solid matrix can selectively stabilize RNA and RNA obtained from the solid matrix can have a RIN number greater than 4. The kit can further include a plasma separation component. RNA obtained from the solid matrix can have a RIN of at least 5 or of at least 6, or of at least 7, or have a RIN of greater than 7. The solid matrix can further include at least one protein denaturant present in the solid matrix in a dry state. The solid matrix can further include at least one reducing agent in the solid matrix in a dry state. The solid matrix can further include at least one UV protectant in the solid matrix in a dry state. The solid matrix can further include at least one buffer present in the solid matrix in a dry state. The buffer can be an acid-titrated buffer reagent that generates a pH in a range from 3 to 6. The solid matrix can be comprised of cellulose, cellulose acetate, glass fiber, or a combination thereof. The solid matrix can be a porous matrix. The solid matrix can be a non-dissolvable dry solid material. The solid matrix can be configured to provide an acidic pH upon hydration. The solid matrix can be configured to extract nucleic acids from a sample, and preserve the nucleic acids in a substantially dry state at ambient temperature. The sample acquisition component can be connected to the sample stabilization component.

In another aspect, a system for collecting and stabilizing a sample is disclosed. The system includes a sample acquisition component with one or more piercing elements configured for penetrating skin to expose blood, and a sample stabilization component coupled to the sample acquisition component, wherein the sample stabilization component comprises a solid substrate comprising melezitose under a substantially dry state with a water content of less than 2%. The solid substrate can include a lysis reagent, one or more biomolecule stabilizing reagents, or a combination thereof. The concentration of melezitose can be present in a range of 10 to 30%. The solid substrate can be configured for preserving enzyme activity.

In another aspect, a system for collecting and stabilizing a biological sample is disclosed. The system includes a sample acquisition component with one or more piercing elements configured for penetrating skin to expose blood, and a sample stabilization component coupled to the sample acquisition component comprising a solid matrix for extraction and storage of a nucleic acid from the biological sample, wherein RNA obtained from the solid matrix has a RIN of at least 4. RNA obtained from the solid matrix can have a RIN of at least 5, or of at least 6, or of at least 7, or can be greater than 7 The solid matrix can further include at least one protein denaturant present in the solid matrix in a dry state. The solid matrix can further include at least one reducing agent in the solid matrix in a dry state. The solid matrix can further include at least one UV protectant in the solid matrix in a dry state. The solid matrix can further include at least one buffer disposed on or impregnated within the solid matrix, wherein the solid matrix is substantially dry with a water content of less than 2%. The buffer can be an acid-titrated buffer reagent that generates a pH in a range from 3 to 6. The solid matrix can be comprised of cellulose, cellulose acetate, glass fiber, or a combination thereof. The solid matrix can also be a porous matrix. The solid matrix can be a non-dissolvable dry solid material. The solid matrix can be configured to provide an acidic pH upon hydration. The solid matrix can be configured to extract a nucleic acid from a sample, and preserve the nucleic acid in a substantially dry state at ambient temperature. The sample acquisition component can be connected to the sample stabilization component.

In another aspect, a system for collecting and stabilizing a biological sample is disclosed. The system includes a sample acquisition component with one or more piercing elements configured for penetrating skin to expose blood, and a sample separation component coupled to the sample acquisition component, wherein the sample acquisition component comprises two or more partially overlapping membranes configured such that one component of the biological sample is collected on a first membrane and the remainder of the sample is collected on a second membrane.

In another aspect, a method is disclosed which involves deploying a tagged sample acquisition and stabilization system to a subject wherein the system includes a blood collection unit configured for collecting a blood sample from the subject, an optional separation module for separating one or more components from the collected blood sample, and a stabilization matrix configured for stabilizing one or more components from the blood sample wherein the tagged sample acquisition and stabilization system comprises a label associated with an assay. The method further includes collecting a deployed tagged sample acquisition and stabilization system, performing one or more assays on the one or more stabilized components based on the tag, and providing a report on the one or more assays performed. The method can further involve separating the stabilization matrix from the system prior to one of the above-mentioned method steps. Optionally, the tag can be on the stabilization matrix. Optionally, when the separation module is present, the tag can be on the optional separation module. The stabilization matrix can be configured to perform multiple assays. The method can further involve identifying stabilized bio-components within the blood sample based on the tag present in a deployed sample acquisition and stabilization system and from that identification determining a stabilized component-specific assay to perform. The sample stabilization system can be labeled with an RFID transmitter, a color label, a barcode, or a second label that differs from the sample tag.

In another aspect, a method for performing analysis on one or more bio-components from a bio-sample from a subject is disclosed. The method involves obtaining a sampling device which includes a sample acquisition component and a stabilization matrix which includes one or more stabilizing reagents configured to selectively stabilize at least one bio-component selected from the group consisting of: RNA, DNA, and protein. The method further involves performing one or more assays on the stabilized bio-components in or on the sampling device at a location remote from where the first method step is carried out. The one or more stabilization reagents can be disposed on or integrated with a solid matrix and can be in a substantially dry state. The solid matrix can be configured to substantially stabilize RNA for at least 11 days at 37 degrees Celsius. The assays can be performed in or on the device, and can include one or more of: PCR, DNA sequencing, RNA expression analysis, and RT-PCR.

In another aspect, a method for performing analysis on one or more bio-components from a bio-sample from a subject is disclosed. The method involves obtaining a sampling device which includes a sample acquisition component and a stabilization matrix comprising one or more stabilizing reagents configured to selectively stabilize the one or more bio-components selected from the group consisting of: RNA, DNA, protein, and a combination thereof. The method further involves removing from the sampling device the stabilization matrix with the one or more bio-components, and performing one or more assays on or directly off of the stabilization matrix. The stabilization matrix can be removed from the sampling device at a location remote from one of the above-mentioned method steps.

In another aspect, a method is disclosed which involves receiving, under ambient conditions, a substantially dry solid matrix comprising one or more stabilization reagents that selectively stabilize one or more bio-components selected from the group consisting of: DNA, RNA and protein, and performing one or more assays directly off of the dry solid matrix for analyzing the selectively stabilized bio-components. The stabilization reagent can include a solid substrate comprising melezitose under a substantially dry state with water content of less than 2%. The stabilization reagent can be coupled to the sample acquisition component comprising a solid matrix for extraction and storage of nucleic acids from the biological sample, wherein RNA obtained from the solid matrix has a RIN of at least 4.

In another aspect, a device for point-of-care or self-administered collection and stabilization of a sample is disclosed and embodiments are illustrated herein. The device includes a sample acquisition component comprising a body and a plunger, wherein the body comprises a proximal end, a distal end, an outer body surface extending between the proximal and distal ends, a base comprising at least one aperture and attached to the distal end, and a lumen defined within the body, wherein the plunger is disposed within the lumen, wherein the plunger comprises a proximal end, a distal end, and at least one needle connected to either end, wherein the at least one needle is configured to pass through the at least one aperture in the base when the plunger is actuated. The device includes a sample stabilization component comprising a reagent and a substrate configured such that components of a bio-sample are extracted and stabilized as the bio-sample migrates through the matrix from a point of collection, wherein the sample stabilization component is disposed within the lumen of the body, such that actuation of the plunger drives the bio-sample through the matrix to further facilitate separation of the bio-sample.

In another aspect, a kit for collecting and stabilizing a sample is disclosed. The kit includes a sample acquisition component with one or more piercing elements configured for penetrating skin to expose blood, and a sample stabilization component, wherein the sample stabilization component comprises a solid substrate comprising melezitose under a substantially dry state. The solid substrate can further include one or more of a lysis reagent and a biomolecule stabilizing reagent. The melezitose can be present at a concentration in a range of 10 to 30%. The solid substrate can be configured for preserving enzyme activity. The kit can further include a plasma separation component.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 is a non-limiting list of tests that can be conducted on the sample.

DETAILED DESCRIPTION OF THE INVENTION

Introduction

Figure 1A:
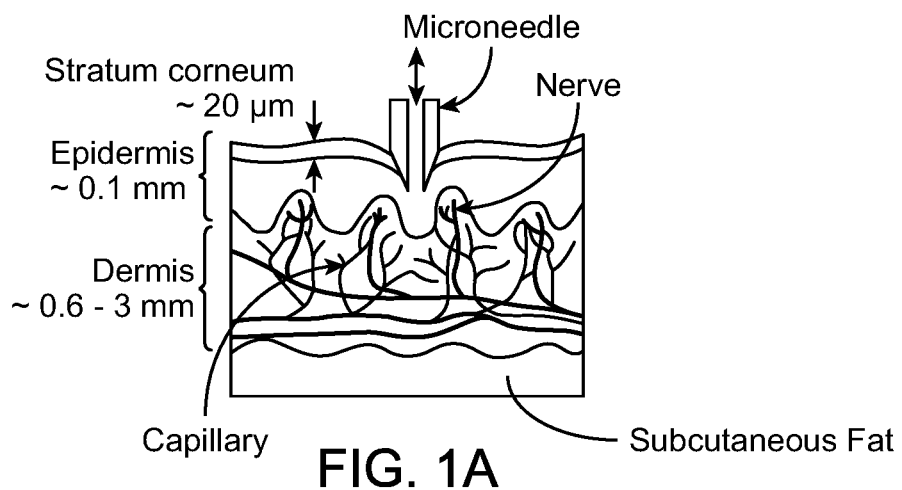
FIG. 1A, FIG. 1B, and FIG. 1C illustrate different sample acquisition components and piercing elements.

A first step towards improving the availability of bio-sample testing and diagnostic testing can involve the development of systems and methods that enable quick sample collection, stabilization and preservation of biological components such as DNA, RNA and/or proteins. Once stabilized, such bio components can be transferred to laboratories that can perform one or more biological assays on the bio components. Easier sample collection can be particularly beneficial for diagnosing clinical conditions. There can also be a benefit to having a subject collect, prepare, and optionally analyze their own blood sample without the assistance of a medical practitioner or access to a medical facility or to have an untrained individual collect and stabilize bio samples from a subject. Technological development in this area can make use of at least three components; first, new developments to provide simple tools for collecting biological samples, such as blood; second, new systems, devices and methods to provide simple user-friendly mechanisms for separating, stabilizing and/or storing collected samples or sample components; and, new compatible approaches for analyzing the samples provided through these new methods.

New technologies can be user-friendly and effective enough that acquisition, collection, optional separation and stabilization of the sample can be performed by trained and un-trained end users. Disclosed within are devices, systems and methods that overcome current limitations by addressing some of the aforementioned issues.

Devices, systems and methods disclosed herein, can provide easier sample collection systems, with user friendly sample collection, optional separation, stabilization and storage of samples. Furthermore, devices, systems, and methods can provide approaches and tools for laboratories to more easily receive, prepare and analyze samples. Provided herein are a compatible set of methods, tools, and systems that can enable samples to be easily collected, stored, pre-treated and prepared for analysis so that sample detection can be accomplished with reduced effort on behalf of the user, patient or sample provider. Devices, systems and methods disclosed herein can reduce the burdens of diagnostic testing by simplifying the process of collecting, optionally separating, and stabilizing bio-samples.

Simplifying the process for blood sample collection can involve devices, systems and methods that separate sample components. In some embodiments methods for collecting venous blood can rely on one or more dedicated medical professionals to oversee every step of the blood collection process; from collecting the samples to post-collection procedures which can include separation steps including centrifugation, followed by labeling and cold storage to stabilize samples until they are transferred to a laboratory for testing. In alternate embodiments, the herein disclosed systems and methods can be configured so that an end user can self administer blood sample collection and provide a stabilized sample to a detection facility for analysis.

The herein presented systems, devices and methods can comprise multiple components including (i) a sample acquisition component (SAC) for simple collection of one or more bio-samples (e.g., blood, urine, or environmental samples such as water or soil), (ii) one or more stabilization components for stabilizing bio-analytes from the one or more bio-samples (e.g., DNA, RNA, or protein), and (iii) optionally a separation component for separation of one or more sample components (e.g., plasma, or cells). A further component of the system or method disclosed herein can include one or more kits, devices, methods, and systems for processing samples and analyzing user-provided samples.

Devices, systems, methods, and kits can include a sample acquisition component (SAC) for acquiring the sample, as well as a sample stabilization component (SSC) for transferring, collecting, and stabilizing the sample. In some instances the sample stabilization component can be further equipped to separate one or more components of the sample prior to transferring the sample to a solid substrate for stabilization. SACs can be easy to use, enabling un-trained professionals to collect samples at a variety of locations, from the clinic to a patient's home or office. SACs can even enable a donor to collect their own sample at home, without the need to visit a medical clinic or a dedicated point of collection where sample collection can be done by a trainer or un-trained professional.

Non-limiting embodiments can include integrated and non-integrated combinations of components for sample acquisition, sample separation and sample stabilization. Embodiments can include a single integrated device with distinct internal components for stabilizing components of the sample. Additional integrated devices can include a single unit, or two or more units for separating components of the sample prior to selectively stabilizing sample components. Other embodiments can provide non-integrated components within a system or kit; components can include a sample acquisition component for acquiring the sample, and a separate sample collection component for stabilizing and optionally separating the sample. The sample stabilization component can include a solid stabilization matrix for selectively stabilizing and storing components of the sample, and it can also have a component for separating the sample prior to stabilization. In yet additional non-integrated systems or kits a sample stabilization component can be separate from the sample separation unit. Further embodiments can provide methods, devices, systems and kits for receiving, preparing, and/or treating the stabilized samples after the sample has been acquired, separated, and components of the sample have been selectively stabilized.

The terms "bio-sample" and "biological sample" can be used herein interchangeably throughout the specification. A biological sample can be blood or any excretory liquid. Non-limiting examples of the biological sample can include saliva, blood, serum, cerebrospinal fluid, semen, feces, plasma, urine, a suspension of cells, or a suspension of cells and viruses. In a non-limiting example, the biological samples can include plant or fungal samples. The present systems and methods can be applied to any biological samples from any organism including human. Bio-samples obtained from an organism can be blood, serum, plasma, synovial fluid, urine, tissue or lymph fluids. A biological sample can contain whole cells, lysed cells, plasma, red blood cells, skin cells, non-nucleic acids (e.g. proteins), nucleic acids (e.g. DNA/RNA) including circulating tumor DNA (ctDNA) and cell free DNA (cfDNA). Several embodiments can disclose methods, devices, and systems for collecting blood samples; however, the systems and methods disclosed herein are not intended to be limited to obtaining a bio-sample from an organism. For example, disclosed embodiments can be used on samples obtained from the environment. Non-limiting examples of environmental samples include water, soil and air samples. In some cases, a sample used in the methods, compositions, kits, devices, or systems provided herein is not a biological sample.

For the purposes of describing the devices, methods, systems, and kits disclosed herein, any individual that uses the devices, methods, systems, or kits to collect a sample can be referred to as the "end user". The individual, organism, or environment from which a sample is derived can be referred to as the "donor". Once the sample is collected it can be deployed to another facility for testing. At the facility the sample can undergo treatment steps that are selected for based on the devices, systems, methods or kits that were used.

Sample Acquisition Component (SAC)

Devices, systems, methods and kits described herein can include one or more sample acquisition components (SACs).

A sample acquired by a system provided herein can be, e.g., a biological sample from an organism, e.g., blood, serum, urine, saliva, tissue, hair, skin cells, semen, or a sample acquired from the environment, e.g., water sample, oil from well, or from food, e.g., milk. Samples can be liquid, solid or a combination of one or more liquids and one or more solids.

Sample volumes can be fixed by components of a unit, including but not limited to the device collection chamber, materials properties of the collection system, sample settings pre-determined by the user, specifications established during device manufacturing, or any combination thereof.

A SAC can include one or more devices for venous blood draw or capillary blood draw. To accomplish venous blood draw or capillary blood draw, the SAC can include one or more piercing elements. The one or more piercing elements can be hollow or solid, and the one or more piercing elements can be configured for pain-free and efficient sample transfer; adaptations can involve use of materials with specific composition, surface microstructure, mechanical properties, structural shapes or combination thereof. The one or more piercing elements can include one or more needles, micro-needles, or lancets (including pressure activated needles or lancets). The SAC can be optionally designed to minimize physical pain or discomfort to the user. An SAC can include micro-needle technology shown in FIG. 1A, which can allow for shallow penetration of the skin to generate blood flow. Examples for sample, e.g., blood collection, contemplated herein include those described in U.S. Pat. No. 9,033,898. The SAC can be single use. In some cases, a SAC is reusable.

A SAC can collect a volume of, e.g., <1 mL. For example, the SAC can be configured to collect a volume of blood e.g., under 1 mL, 500 µl, 400 µl, 300 µl, 200 µl, 100 µl, 90 µl, 80 µl, 70 µl, 60 µl, 50 µl, 40 µl, 30 µl, 20 µl or 10 µl.

A SACs can be designed to collect a sample volume of from about 1 mL to about 10 mL or from about 1 mL to about 100 mL. Examples of a SAC include a urine cup, a finger stick, or devices, such as those described, e.g., in US. Pub. Nos. 20130211289 and 20150211967.

A SAC can be a component of an integrated device designed for collecting, stabilizing and storing a sample. A SAC can be a separate component that is part of a kit or a system. A SAC can include a vial for collecting the sample.

A kit can include one or more of the following (e.g., when a SAC is non-integrated but is part of a kit): (i) one or more sample separation units, (ii) one or more sample stabilization units, (iii) one or more bio-sample separation and/or stabilization components. A kit used for blood samples can comprise a capillary or transfer tube for collecting a blood drop from a lanced or incised finger and subsequently dispensing the blood onto a device or separate unit for stabilizing or separating and stabilized sample components.

Figure 1B:
Figure 1C:
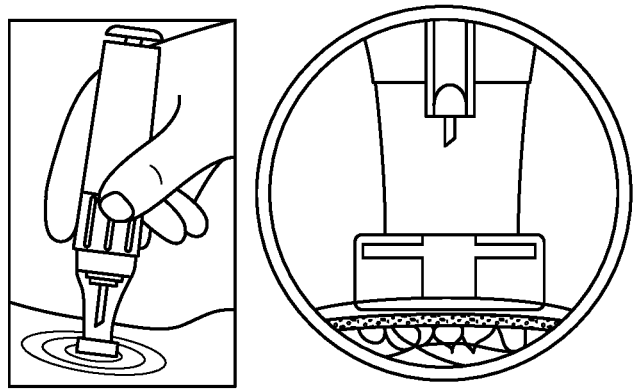
Figure 2:
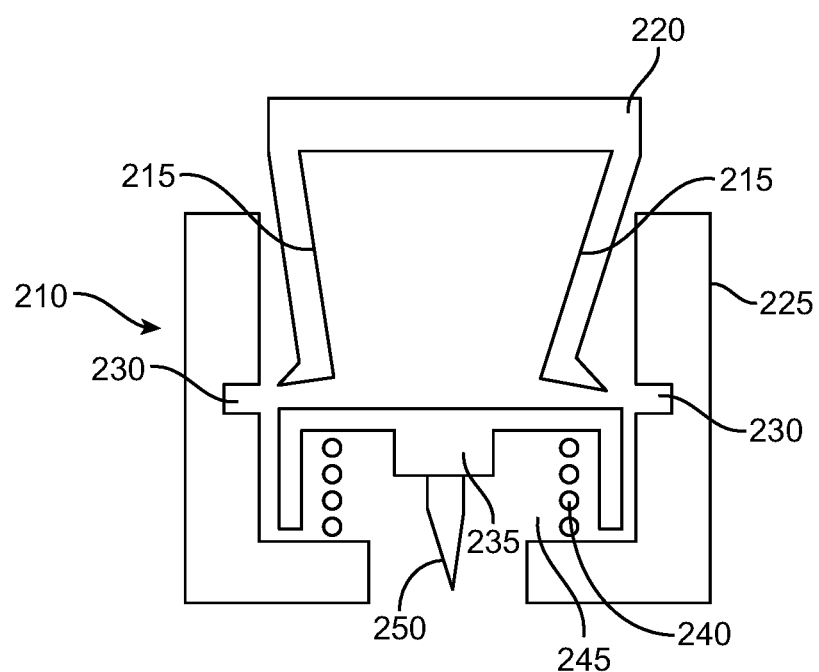
FIG. 2 illustrates an embodiment of a sample acquisition component.

Some embodiments of the sample acquisition component are illustrated in FIG. 1B, FIG. 1C and FIG. 2. As shown in FIG. 1B the SAC can be activated through a mechanical means. Manual activation can be performed by the donor or end user. FIG. 1C illustrates a SAC that can be activated with electrical means. The SAC, as shown, can uses vibration to induce blood flow.

The SAC can use a plunger to create a vacuum that drives the sample into one or more chambers in the device. As shown in FIG. 2, the sample acquisition component (SAC) can have a proximal end, a distal end, an outer surface and a lumen defined with the body 215. The base attached to the distal end of the body can comprise an outer face, an inner face and comprise one or more apertures 240. Additionally, the device can have a plunger 220 comprising a proximal and distal end, with the plunger configured to be user actuated. One or more piercing elements 250 can be fixed to the face of the plunger, and when the user actuates the SAC from the proximal end to the distal end of the device body, the one or more piercing elements can puncture the skin. A vacuum can be created upon withdrawal of the piercing elements. Blood can pool through the one or more apertures 240, and the one or more apertures can be configured to draw the sample into the lumen. The sample can move into the lumen and within the device, e.g., through spontaneous capillary-driven flow. Spontaneous capillary-driven flow can also be used to extract fluid from a pool or droplet on a surface, such as human skin, for a reservoir, or from another open microfluidic channel Spontaneous capillary driven flow can be used to collect the sample from the lance site; it can also be used to manipulate fluids from a reservoir within the device or between sample collection and preparation steps using complex open microfluidic channels. In alternative embodiments, spontaneous capillary-driven flow can be combined with other means of moving sample through the device. The apertures can be optionally adapted for, or optionally contain materials or structures adapted to draw the sample from the penetrated skin into the device. For example in one embodiment, the one or more piercing elements can partially retract into the one or more apertures wherein the properties of the one or more piercing elements itself draw the sample through the aperture and into the sample chamber, either through the one or more piercing elements if the one or more piercing elements is hollow or on the sides of the one or more piercing elements if the one or more piercing elements are solid. Embodiments of these components can be found in US. Pub. No. 20130211289.

Sample collection can occur from sample pooled at or above the skin surface, it can also optionally be collected from one or more reservoirs under the skin. The SAC can, for example, create a lancing motion which cuts into small but plentiful capillaries in the superficial vascular plexus under the epidermis e.g., at depth of 0.3-0.6 mm from the surface of the skin. This disclosure provides a system for mechanically massaging a lance site at other body locations by several different approaches, including oscillating an annular ring surrounding the wound to pump the blood surrounding the wound into the wound for extraction by a needle or capillary tube or oscillating paddles or other members adjacent the wound to achieve the desired blood flow. Further, bringing a drop of blood from the skin in other regions of the body, e.g., the thigh, to a small area on a test device can be difficult. An alternate embodiment of the described herein can work with the needle remaining in the wound and the needle being mechanically manipulated to promote the formation of a sample of body fluid in the wound.

Liquid sample can collect or pool into a collection chamber, after the collection chamber or in lieu of a collection chamber the sample can optionally be absorbed through one or more particles, materials, structures or filters with optimized porosity and absorptivity for drawing the sample into the device. Materials for drawing the sample into the devices herein can consist of any absorptive or adsorptive surfaces, or materials with modified surfaces; optional materials including but not limited to paper-based media, gels, beads, membranes, polymer based matrices or any combination thereof. For example in one embodiment, the SAC can comprise a body that defines a fluid flow path from an inlet opening, wherein the flow path includes a bed of a porous polymer monolith selected to adsorb biological particles or analytes from a matrix drawn or dispensed through the inlet opening and the bed. The porous polymer monolith can absorb biological particles or analytes for later preparation steps. Examples of sample collection on a porous monolith can be found in US Pub. No. US20150211967.

Figure 3:
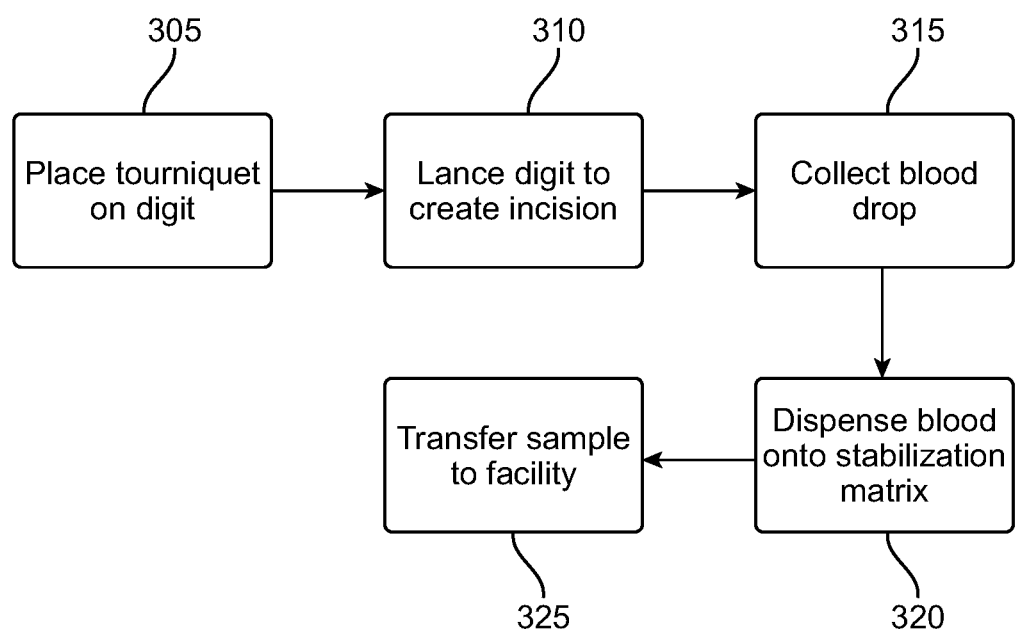
FIG. 3 is a flow diagram depicting a method for extracting a blood sample using a tourniquet.

Methods for using the sample acquisition component (SAC) can include piercing the skin with a SAC followed by milking or squeezing of a finger to extract a blood sample. The SAC can be used with a tourniquet or other components for facilitating sample acquisition. A tourniquet, rubber band, or elastic material can be placed around the first, second, or third digit of a subject's hand. Methods can be constructed to improve sample quality. As depicted in FIG. 3, steps can include placing a tourniquet on one of the digits of the donor's finger to apply pressure 305 and lancing the digit to create an incision 310. The method can also include optionally removing the first blood immediately after lancing while still applying pressure. Blood can be collected from the incision 315 by holding a capillary tube against a blood drop formed from the incision site. Blood collected in the capillary tube can be dispersed onto a separate component of the system 320, and the separate part of the component can be deployed to a different location or facility 325 for analysis. In certain embodiments the kit can include components and instructions for facilitating blood collection and efficiency. Methods can further comprise steps for preparing the hand and finger to insure proper blood flow including temperature and position, methods of applying the tourniquet to the finger, methods of sterilization, lancing, and actual blood collection. Methods for collecting blood samples are disclosed, e.g., in U.S. application Ser. No. 14/450,585.

Sample Stabilization Component

A sample acquired using a sample acquisition component, e.g, a SAC described herein, cancan be transferred to a sample stabilization component (SSC). A SSC can be any device or system that the sample is collected on or transferred to for stabilization and storage. The device or system can comprise channels and compartments for collecting and transferring the samples, and one or more units for separating and stabilizing sample.

In a non-integrated system, the sample acquisition component can be physically separate from the sample stabilization component. In these embodiments, transfer from the sample acquisition component to the sample stabilization component can occur through a variety of means including one or more: needles, capillary tubes, or through direct transfer of the sample from the donor site to the sample stabilization component. In instances where the sample acquisition component is a separate component from the sample stabilization component, application of a sample to a substrate can be achieved using a self-filling capillary for collection from the sample acquisition component, followed by sample transfer to the substrate.

The sample stabilization component can be integrated with the SAC. Integration between the sample stabilization component and the SAC can occur through a shared assembled interface. Sample can move from the sample acquisition component through channels, including microchannels, spontaneous capillary flow, wicking through absorbent materials or other means that allow sample to flow through the sample stabilization component towards or into the substrate with minimal effort on behalf of the end user. Microchannels can be constructed from a variety of materials with properties including adapted shapes with surface microstructures and material properties adapted to facilitate capillary action or other means of sample transfer through the device. Microchannels can comprise any means of transferring sample between chambers, including open microfluidic channels optimized for moving samples using spontaneous capillary flow. Examples of microchannels and devices comprising microchannels can be found in many of the incorporated references, including US Pub. No. 20140038306.

The sample stabilization component can include a structure with multiple layers. It can also have an interface for accepting transfer to one or more layers or to a substrate. The sample stabilization component can be configured for collecting one or more samples, separating components of a sample, stabilizing one or more samples, or any combination thereof. The SSC can further comprise a network of layers and capillary channels configured for transferring sample between multiple layers and into substrate, e.g., as provided for by U.S. application Ser. Nos. 14/340693 and 14/341,074.

The SSC can be coupled to the substrate in a variety of ways. The SSC can couple to the substrate in a way that enables contact with a layer for transferring the sample fluid from the integrated device to the substrate. The SSC can be configured such that the device is easily removable from the substrate. The system can further comprise a substrate frame having a region configured to receive the sample on the substrate. The substrate can be attached to the substrate frame in a way that makes it easy to remove the substrate from the system, and the substrate frame can be designed with a barcode to enable automated or semi-automated processing. The system can further be coupled to an external device, wherein the external device comprises a fluidic device, an analytical instrument, or both. In one or more embodiments, the sample stabilization component can be coupled to a substrate, wherein SSC is configured to transfer the sample fluid to the substrate. The substrate can comprise the substrate or the sample separation component. The SSC can either be attached directly to the substrate or to a substrate frame that holds the substrate. In some embodiments, the SSC can further couple to a substrate frame and a substrate cover. The substrate frame and substrate cover can include features to facilitate efficient fluid transfer to the substrate at a region of interest, e.g., at the center of the substrate. In some embodiments, the SSC is packaged with a sample storage substrate, wherein the sample stabilization component is pre-attached to the sample substrate. In some other embodiments, the SSC and substrate are packaged separately, wherein the user can assemble the substrate and the SSC for sample collection, transfer, stabilization and storage. The SSC can be further packaged with a sample acquisition component (SAC).

A SSC can be disposable or re-usable. For example, an SSC can be a single-use disposable device configured to collect the sample and transfer the sample fluid to a substrate and facilitate loading of the fluid sample through desirable areas of the substrate. The SSC can be configured for one time use to reduce or prevent contamination or spreading of infection via the collected sample. The SSC can be configured for reliable and reproducible collection, transfer and storage of biological samples.

After collection and transfer of the biological sample, the substrate can be configured to separate bio-sample components prior to transferring to the stabilization matrix for storage.

Sample Separation

The SSC can include a sample separation unit comprising one or more substrates, membranes, or filters for separating sample components. The sample separation unit can be integrated within the sample stabilization component, or it can be attached to or separate from the sample stabilization component.

Sample separation can occur at different points in the sample collection process. For example, in an integrated device sample separation can occur within the SSC, for non-integrated devices sample separation can occur outside of the SSC prior to transfer to the sample stabilization component. In other instances the sample can move through the SAC and into the sample separation unit before being transferred to the SSC which can transfer the separated sample to one or more substrates for stabilization and storage.

Sample separation can occur as an intermediate step between sample acquisition and transfer to a sample stabilization matrix. In some instances sample separation and stabilization can occur in one step without the need for user intervention. Sample separation can further occur sequentially or simultaneously with sample stabilization.

The sample acquisition and stabilization can require user action to proceed between one or more phases of the sample collection, optional separation, and stabilization process. An integrated device can require user action to activate sample acquisition, and move sample between separation, stabilization, and storage. Alternatively, user action can be required to initiate sample acquisition as well as one or more additional steps of the sample collection, separation or stabilization process. User action can include any number of actions, including pushing a button, tapping, shaking, rupture of internal parts, turning or rotating components of the device, forcing sample through one or more chambers and any number of other mechanisms. Movement through the phases can occur in tandem with sample collection, or can occur after sample collection. Anytime during or prior to the processing phases the entire sample or components of the sample can be exposed to any number of techniques or treatment strategies for pre-treatment of cells of biological components of the sample; potential treatment includes but is not limited to treatment with reagents, detergents, evaporative techniques, mechanical stress or any combination thereof.

The devices, methods, systems and kits disclosed herein can comprise one or more sample separation units. Sample separation units can be used, e.g., to separate plasma from blood, cells from a water sample, or cells from cell free components. For blood samples one or more components can be used to separate plasma or specific cells from other components of a blood sample. Alternatively, separation devices, methods and systems can selectively separate any number of sample components including cells, plasma, platelets, specific cell types, DNA, RNA, protein, inorganic materials, drugs, or any other components.

Non-limiting embodiments of the sample stabilization unit can employ sample separation components to separate other non-plasma components as well. Sample separation components can be connected to the sample acquisition component e.g., through one or more channels, including one or more microchannels, wicking of absorbent materials or other means that allow sample to flow through the device. The systems and methods for separating the sample are exemplary and non-limiting.

There can be many methods for performing separation, some of which use size, deformability, shape or any combination thereof. Separation can occur through one or more membranes, chambers, filters, polymers, or other materials. Membranes, substrates, filters and other components of the device can be chemically treated to selectively stabilize components, facilitate flow of sample, dry the sample, or any combination thereof. Alternative separation mechanisms can include liquid-liquid extraction, solid-liquid extraction, and selective precipitation of target or non-target elements, charge separation, binding affinity, or any combination thereof. Separation phase can be comprised of one or more steps, with each step relying on different mechanisms to separate the sample. One such mechanism can utilize size, shape or deformation to separate larger components from smaller ones. Cell separation can occur through a sorter that can for example rely on one or more filters or other size exclusion methods to separate components of the sample. Separation can also be conducted through selective binding wherein specific components are separated by binding events while the unbound elutant moves into or through alternate chambers.

In some methods, a single membrane can be used for separation and collection of one or more sample components from the bulk sample. Single membrane methods can use a device wherein samples can be applied to one end of the membrane and as the sample flows through a first component of the sample, for example cells, can be separated from a second component of the sample, for example plasma, based on the size of the membranes pores. After operation of the device the membrane containing the first component of the sample, cells in this example, can be severed from the portion containing the second component of the sample, plasma in this example, necessitating an additional step of severing the membranes. In another method, two separate membranes can be used for the separation and collection sample components; specifically, a first membrane for the separation of one component, for example blood cells, and a second membrane for collection of other components, for example plasma. These membranes can be arranged such that a distal end of the first membrane contacts a proximal end of the second membrane to facilitate the separation of a large component, for example cells, via the first membrane and the collection of a second smaller component, for example plasma, via the second membrane.

Figure 4A:
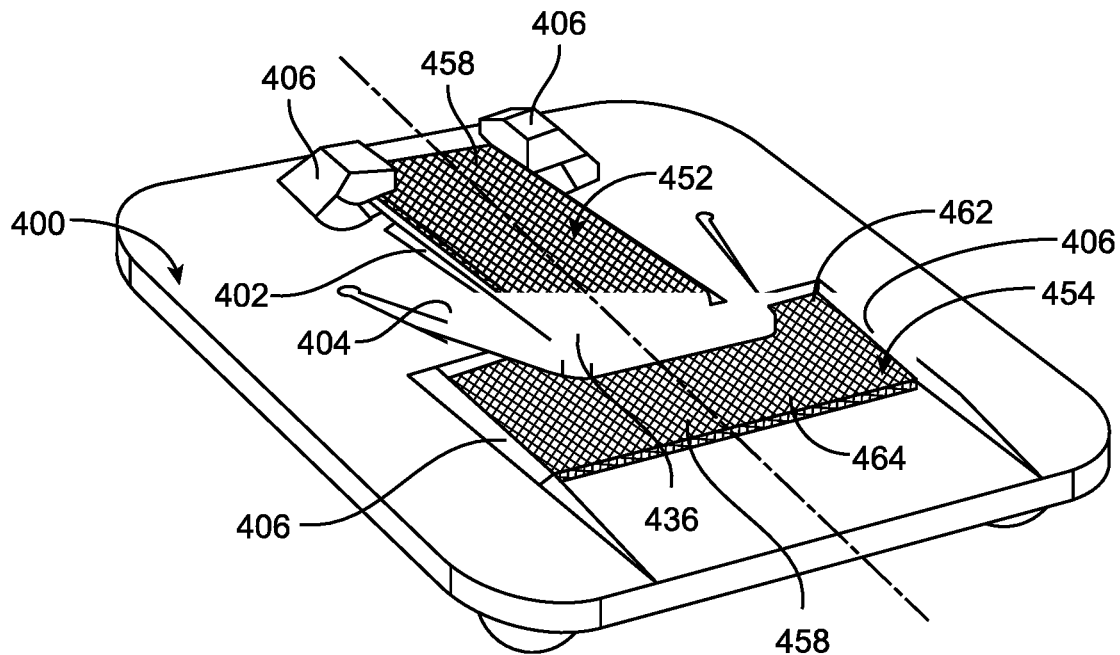
FIG. 4A and FIG. 4B illustrate an embodiment of the separation component.
Figure 4B:
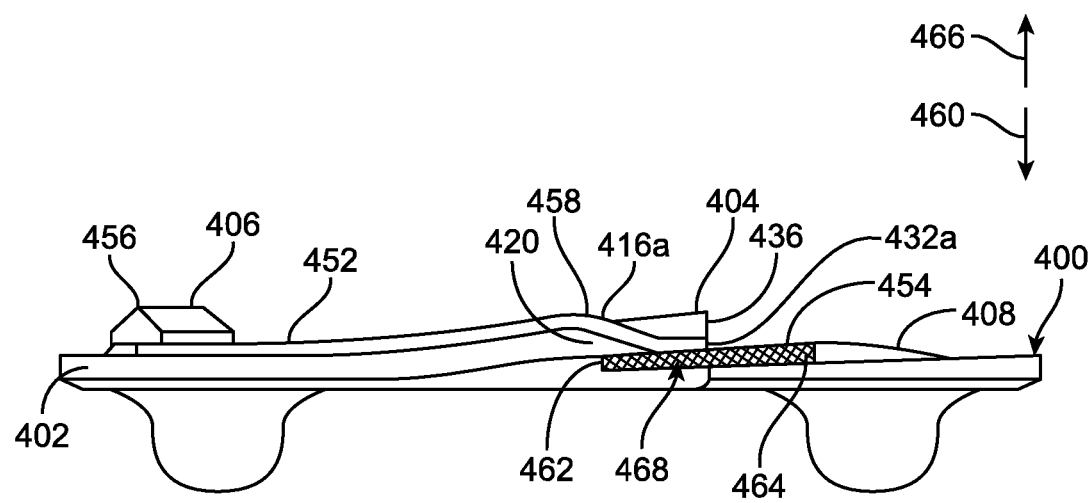

FIG. 4A and FIG. 4B illustrate a sample separation unit that can be used to separate samples prior to stabilization or in tandem with stabilization. Sample separation units can comprise a frame 400, a separation membrane 452, and a collection membrane 454. The frame can include an inner side disposed proximate to a first peripheral portion of the frame. The inner side 402 is formed from a plurality of first slots in the frame 416. The frame further includes an outer side 404 disposed surrounding at least a portion of the plurality of first slots 416. The outer side 404 is formed from a plurality of second slots in the frame 432. A distal end of the separation membrane 420 is disposed under the outer side, and a proximal end of the collection membrane is disposed under at least one of the outer side and inner side such that the proximal end of the collection membrane has an overlapping contact area 428 with the distal end of the separation membrane. Further, the outer side is configured to apply pressure on the separation and collection membranes about the overlapping contact area. The frame 400, separation membrane 452, and collection membrane 454, can be comprised of different materials. The frame 400 can be comprised of a polymer material such as polypropylene, nylon (polyamide), high density polyethylene (HDPE), and polyetheretherketone (PEEK); and it can be manufactured using an injection molding technique and has a uniform thickness. The separation membrane 452 can include suitable materials such as cellulose, a glass fiber, a cellulose acetate, a poly vinyl pyrrolidone, a polysulfone, a polyethersulfone, a polyester or combinations of these materials; and it can be designed to have a geometry compatible with the geometry of the frame 400, specifically, the geometry of the inner side 402 of the frame 400. The collection membrane 454 can include suitable materials such as cellulose, a glass fiber, a cellulose acetate, a poly vinyl pyrrolidone, a polysulfone, a polyethersulfone, polyester, or combinations of these materials; and the collection membrane can be chemically treated. Other embodiments and methods can include the step of displacing, such as by pressing downwards 460, an inner side of the frame 402 to insert a distal end 458 of a separation membrane 452 under the second distal end portion 436 of the outer side of the frame 404 via a first mid-slot 416b of the inner side 402. The method can further include the step of displacing the outer 404 and inner sides 402, for example by applying pressure by pushing upwards 466, to insert a proximal end 462 of a collection membrane 454 under at least one of the outer and the inner sides via a second mid-slot of the outer side 432b, such that the proximal end of the collection membrane has an overlapping contact area 468 with the distal end 458 of the separation membrane 452.

The separation machinery can be optional, for example it can be part of a modular system wherein the user or the manufacturer can insert a cartridge within the path of the sample. In one potential embodiment the sample can be transferred from any of the previously mentioned collection devices into a secondary chamber. The transfer can be facilitated by user action or it can happen spontaneously without user action.

Figure 5:
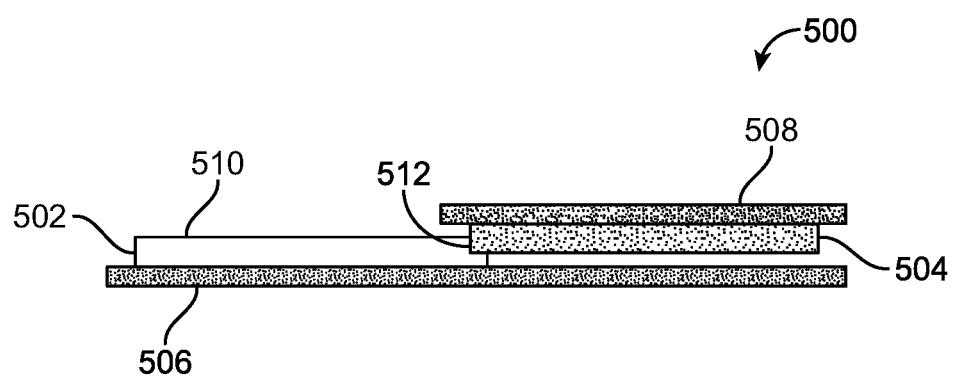
FIG. 5 illustrates another embodiment of the sample separation component.

The sample separation unit can use a filtration membrane to separate sample components. FIG. 5 illustrates a sample separation unit with a filtration membrane that separates out the non-cellular fraction of a biological sample. The filtration membrane 502 can have a sample application zone 510 and a transfer zone 512. The filtration membrane can be in direct contact with a solid matrix 504 via the transfer zone 512. A biological sample can be applied to the sample application zone 510 of the filtration membrane, and can be filtered as it moves through the filtration membrane. The filtration membrane can have a plurality of pores. Once the biological sample passes through the filtration membrane, resident intact cells within the biological sample can be retained by the filtration membrane, e.g., mostly at the sample application zone 510 and the non-cellular fraction can be passed through the pores to reach the transfer zone 512 and get transferred and collected onto the dry solid matrix. A filtration membrane can have pore sizes that can range from about 0.01 micron to about 5 micron. The filtration membrane can have a range of pore sizes, for example, between about 1 micron to about 2 micron. The pore size can vary between about 0.22 micron to about 2 microns. When a filtration membrane of 1 micron pore size is used, any other circulating eukaryotic cells and/or pathogenic cells having diameters greater than 1 micron can be retained in the filtration membrane and so will not reach the dry solid matrix upon filtration. Additional separation components are described in US Publ. No. 20150031035.

Filtration can occur at various points in the sample collection process. A non-cellular fraction of a sample can, for example, be filtered out from the biological sample at the point-of-collection itself. Filtration can be performed without any prior pre-treatment of the biological sample. Further filtration can be performed in absence of any stabilizing reagent.

Filtration membrane can be made from a variety of materials. The materials used to form the filtration membrane can be a natural material, a synthetic material, or a naturally occurring material that is synthetically modified. Suitable materials that can be used to make the filtration membrane include, but are not limited to, glass fiber, polyvinlyl alcohol-bound glass fiber, polyethersulfone, polypropylene, polyvinylidene fluoride, polycarbonate, cellulose acetate, nitrocellulose, hydrophilic expanded poly(tetrafluoroethylene), anodic aluminum oxide, track-etched polycarbonate, electrospun nanofibers or polyvinylpyrrolidone. In one example, the filtration membrane is formed from polyvinyl alcohol-bound glass fiber filter (MF1™ membrane, GE Healthcare). In another example, filtration membrane is formed from asymmetric polyethersulfone (Vivid™, Pall Corporation). In some embodiments, filtration membrane can be formed by a combination of two or more different polymers. For example, filtration membrane can be formed by a combination of polyethersulfone and polyvinylpyrrolidone (Primecare™, iPOC).

After filtration, the separated, non-cellular fraction can be collected onto a dry solid matrix by means of physical interaction. The non-cellular fraction can be collected on to dry solid matrix by means of adsorption or absorption.

Stabilization Matrix

Figure 6:
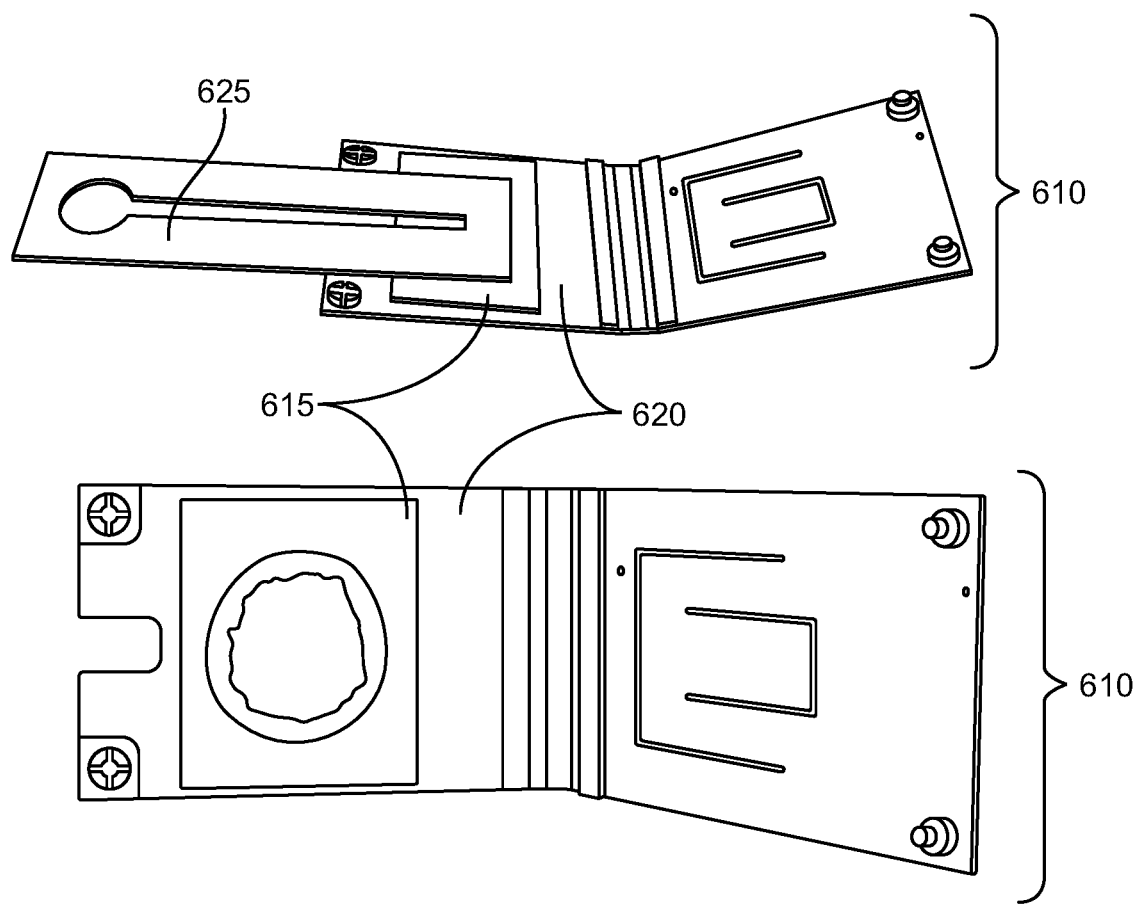
FIG. 6 illustrates a sample stabilization component with a stabilization matrix.

The SSC can be used to transfer, stabilize, and store target components of a bio-sample which can comprise target components such as nucleic acids, proteins, and respective fragments thereof. The SSC can receive, extract and stabilize one or more of these analytes onto a substrate that can be coupled to or housed within the sample stabilization component. FIG. 6 illustrates an example of a sample stabilization component 610 with a sample substrate or matrix 615 for preserving or stabilizing the sample. The substrate 615 can be held in place on one side of the device using a frame 620. The sample can be collected and transferred through a channel 625 to the mounted sample substrate.

The term "target components" as used herein, can refer to one or more molecules, e.g., biological molecules that can be detected or tested for, in a given diagnostic test. The target components for a particular test can need to be adequately preserved and stabilized for good quality diagnostic results.

The nature of the sample can for example depend upon the source of the material, e.g., biological material. For example, the source can be from a range of biological organisms including, but not limited to, virus, bacterium, plant and animal. The source can be a mammalian or a human subject. For mammalian and human sources, the sample can be selected from the group consisting of tissue, cell, blood, plasma, saliva and urine. In another aspect, the bio-sample is selected from the group consisting of biomolecules, synthetically-derived biomolecules, cellular components and biopharmaceutical drug.

The composition, stability and quality of target components can vary depending on their source, therefore to a variety of different substrates can be used to stabilize different components of the sample and prepare the sample for testing. The chemical nature and properties of the target components can vary depending on the origin of the sample, and the degree of required sample stabilization can depend on the diagnostic panel the sample is intended for. Some panels, for example, can require high concentration and low quality sample while others require low concentration and high quality sample. High quality reproducible test results can require high quality samples. The composition of the substrate as well as the substrate and methods for stabilizing sample can differ between assays and between target components or analytes.

Since the nature of target components can differ, the substrate or matrix composition can also be selected for or configured to specific target components. Sample sources and/or the diagnostic tests intended for a particular sample can also be variables that determine the composition of the substrate or matrix. For example, high quality diagnostic test results can require high quality or effective stabilization of target components. In some instances the composition of the substrate or stabilization matrix can be designed to specifically stabilize a particular target component (e.g. DNA, RNA or protein). The matrix can be further configured for use in a particular diagnostic test; for example, if the test requires higher concentration of a particular type of target component then the matrix can be designed to selectively release that target component.

Sample processing can be performed with the different types of tests and substrate compositions in mind. For example, a substrate or matrix designed for a specific target component or diagnostic test can have a color or code that indicates the type of assay it can be used for or with. The substrate can also incorporate one or more tags or labels, including barcodes, RFIDs, or other identifiers that allow the samples or results derived from the substrate to be connected with a particular end user or donor.

The term "substrate" or "stabilization matrix" can refer to any solid matrix including a substrate, or the sample separation component herein described. Substrate can be any solid material including one or more absorbent materials which can absorb a fluidic sample, such as blood.

The substrate or stabilization matrix can comprise one or more different solid components. The solid components can be kept in a substantially dry state of less than 10 wt % hydration. Examples of solid matrix substrate include but are not limited to, a natural material, a synthetic material, or a naturally occurring material that is synthetically modified. The substrate can comprises cellulose, nitrocellulose, modified porous nitrocellulose or cellulose based substrates, polyethyleneglycol-modified nitrocellulose, a cellulose acetate membrane, a nitrocellulose mixed ester membrane, a glass fiber, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, glass fiber membranes, quartz fiber membranes or combinations thereof. Suitable materials that can act as dry solid matrix include, but are not limited to, cellulose, cellulose acetate, nitrocellulose, carboxymethylcellulose, quartz fiber, hydrophilic polymers, polytetrafluroethylene, fiberglass and porous ceramics. Hydrophilic polymers can be polyester, polyamide or carbohydrate polymers.

The substrate or matrix can comprise one or more dried reagents impregnated therein. The one or more dried reagents can comprise protein stabilizing reagents, nucleic acid stabilizing reagents, cell-lysis reagents or combinations thereof. In one embodiment, the substrate is disposed on a substrate frame. Non-limiting examples of the sample substrate can include a porous sample substrate, Whatman FTA™ card, cellulose card, or combinations thereof. In some embodiments, the substrate can include at least one stabilizing reagent that preserves at least one biological sample analyte for transport or storage. Non-limiting examples of suitable reagents for storage media can include one or more of a weak base, a chelating agent and optionally, uric acid or a urate salt or the addition of a chaotropic salt, alone or in combination with a surfactant.

In some instances, the substrate can comprise a dry solid matrix comprised of cellulose. The cellulose-based dry solid matrix is devoid of any detergent. Cellulose-based dry solid matrix cannot be impregnated with any reagent. Cellulose-based dry solid matrix can be impregnated with a chaotropic salt. Examples of chaotropic salt include, but are not limited to, guanidine thiocyanate, guanidine chloride, guanidine hydrochloride, guanidine isothiocyanate, sodium thiocyanate, and sodium iodide. In some embodiments, the cellulose-based dry solid matrix is FTA™ Elute (GE Healthcare). Examples of sample stabilization components can be found, e.g., in US Pub. Nos. US20130289265 and US20130289257.

Substrate can be comprised of one or more layers of material. The substrate can be arranged into a solid matrix. Layers can be arranged to selectively extract specific biosample components. Solid matrix can be a single material, or it can be comprised of multiple materials.

Multiple sample stabilization units can be stored in or attached to a single sample stabilization component. A single sample stabilization unit can be stored in the sample stabilization component. Alternatively, two or more sample stabilization units can be linked together such that one or more components of the bio-sample can move through the different units. The sample stabilization matrix or substrate in any of the mentioned embodiments can have uniform or variable composition. The substrate, sample stabilization unit, or components of either the substrate or the sample stabilization unit can be tagged to indicate the type of target component(s) it is intended for, and/or the diagnostic test(s) for which a sample is intended.

The substrate can be constructed such that sample processing can occur within or adjacent to the sample stabilization component. In some embodiments a sample can move through a sample separation step before being exposed to one or more sample stabilization matrices. In some embodiments the acquisition, optional separation and stabilization steps occur in tandem.

For target components that are present in low concentrations, the substrate can be configured to enhance recovery. In these instances the solid substrate can comprise at least one surface coated with a chemical mixture that enhances the recovery of a biological material from the surface. The chemical mixture can comprise components selected from the group consisting of vinyl polymer and non-ionic detergent, vinyl polymer and protein, non-ionic synthetic polymer and non-ionic detergent, non-ionic synthetic polymer and protein, polyethylenemine (PEI) and non-ionic detergent, non-ionic detergent and protein, and polyethylenemine (PEI) and protein. The solid support can be selected from the group consisting of paper, glass microfiber and membrane. The support can be a paper, for example a cellulose paper including a 903 Neonatal STD card. The solid support can comprise a membrane selected from the group consisting of polyester, polyether sulfone (PES), polyamide (Nylon), polypropylene, polytet-rafluoroethylene (PTFE), polycarbonate, cellulose nitrate, cellulose acetate and aluminium oxide. The vinyl polymer can be polyvinyl pyrrolidone (PVP). The non-ionic detergent can be Tween 20. The protein can be selected from the group consisting of albumin and casein. The non-ionic synthetic polymer can be poly-2-ethyl-2-oxazoline (PEOX). The chemical mixture can comprise any combination of polyvinyl pyrrolidone (PVP), Tween 20, albumin, poly-2-ethyl-2-oxazoline (PEOX), polyethylen-emine (PEI), polyeth-ylenemine (PEI) or casein. Also provided herein are methods for recovering a material, e.g., biological material from a solid support comprising the steps of i) contacting a surface of a solid support, e.g., as described herein with a sample containing a biological material; ii) drying the sample on the surface of the solid support; iii) storing the solid support; and iv) extracting the material, e.g., biological material from the surface. In other aspects, step iii) comprises storing the paper support at a temperature in the range of about 15 to about 40° C. The paper support can be stored at a lower temperature depending on the thermal stability of the biological material. Methods of making the substrate can comprise coating at least one surface of the support with a solution of a chemical mixture that enhances the recovery of a biological material from the surface, wherein the chemical mixture is a mixture selected from the group consisting of polyvinyl pyrrolidone (PVP) and Tween 20, polyvinyl pyrrolidone (PVP) and albumin, Tween 20 and albumin, poly-2-ethyl-2-oxazoline (PEOX) and Tween 20, poly-2-ethyl-2-oxazoline PEOX and albumin, polyethylenemine (PEI) and Tween 20, and polyethylen-emine (PEI) and albumin. The sample stabilization component can provide a use of a solid support as described herein for enhancing the recovery of a material, e.g., biological material from a surface thereof, wherein the disclosed stabilization components and methods are disclosed, e.g., in US Publ. Nos. US20130323723 and US2013330750, the entireties of which are herein incorporated by reference.

The substrate or solid matrix can be configured to selectively preserve nucleic acids including RNA, DNA and fragments thereof. A solid matrix for selectively stabilizing nucleic acids can be comprised of at least one protein denaturant, and at least one acid or acid-titrated buffer reagent impregnated and stored in a dry state. The matrix can be configured to provide an acidic pH upon hydration, extract nucleic acids from a sample and/or preserve the nucleic acids in a substantially dry state at ambient temperature.

A stabilization matrix for extracting and stabilizing nucleic acids can comprise any combination of reagents including a protein denaturant, a reducing agent, buffer, a free-radical trap, a chaotropic agent, a detergent, or an RNase inhibitor in the solid matrix in a dried format. The RNase inhibitor can comprise a triphosphate salt, pyrophosphate salt an acid, or an acid-titrated buffer reagent. The stabilization matrix can further be impregnated with or in the presence of one or more reagents including enzyme inhibitors, free-radical scavengers, or chelating agents. The solid matrix can comprise a protein denaturant, a reducing agent, a buffer, and optionally a free-radical trap or RNase inhibitor.

One or more reagents can be impregnated and stored in a dry state. One or more dried reagents can be optionally rehydrated by the addition of buffer, water or sample. The matrix can further comprise a weak or strong protein denaturant. In certain aspects the solid matrix is a porous cellulose-based paper such as the commercially available 903, 31-ETF, or FTA Elute™. Performance of this method permits the storage of nucleic acids, e.g., RNA which can be an unstable biomolecule to store, in a dry format (e.g., on a solid matrix) under ambient temperatures. The solid matrix can be configured such that hydration of the matrix provides an acidic pH. As noted, in one or more embodiments, RNA quality can be determined by capillary electrophoresis of the extracted RNA through a bioanalyzer. The dry solid matrix can permit prolonged storage of one or more bio-components comprising nucleic acids (e.g., RNA, DNA) in a dry format under ambient conditions. In other aspects, a dry solid matrix for ambient extraction and storage of nucleic acids (e.g., RNA, DNA) from a sample comprises a thiocyanate salt, a reducing agent, a buffer, and optionally a free-radical trap or RNase inhibitor present in a solid matrix in a dried format. A dry solid matrix for extraction and storage of nucleic acids (e.g., RNA, DNA) from a sample comprises at least one metal thiocyanate salt, wherein at least one metal thiocyanate salt is not guanidinium thiocyanate (GuSCN), a reducing agent, a buffer, and optionally a free-radical trap or RNase inhibitor. The solid matrices can comprise nucleic acids (e.g., RNA, DNA) in a dry format can be subjected to a process to release the nucleic acids from the solid matrix in an intact format that is suitable for further analyses of the collected nucleic acid samples.

RNA quality can be quantified as an RIN number, wherein the RIN can be calculated by an algorithmic assessment of the amounts of various RNAs present within the extracted RNA. High-quality cellular RNA can exhibit a RIN value approaching 10. In one or more embodiments, the RNA extracted from the dry matrix has a RIN value of at least 4. In some embodiments, the matrix provides for ambient extraction and stabilization of a bio-sample and produces intact, high quality RNA with a RIN value in a range from about 4 to about 10, or in some embodiments, the RIN value is in a range from about 5 to about 8. The matrix can be a porous non-dissolvable dry material configured to provide a pH between about 2 and about 7 upon hydration for extracting RNA. The matrix can stabilize the extracted RNA with an RNA Integrity Number (RIN) of at least 4.

Methods for extracting and storing nucleic acids from a sample can comprise steps of providing the sample to a dry solid matrix comprising a protein denaturant and an acid or acid titrated buffer reagent; generating an acidic pH upon hydration for extraction of nucleic acids from the sample; drying the matrix comprising the extracted nucleic acids; and storing the extracted nucleic acids on the matrix in a substantially dry state at ambient temperature. Examples of the aforementioned sample stabilization components can be found, .e.g, in US Pub. No. US20130338351.

A sample stabilization unit can include a solid matrix for collection and stabilization of non-nucleic acid components, for example proteins. In these instances, the substrate can be configured to extract and stabilize proteins or peptides from a biological sample for preservation at ambient temperature. In one such embodiment, the solid substrate for collection, stabilization and elution of biomolecules can comprise a trisaccharide under a substantially dry state. The trisaccharide can be selected from melezitose, raffinose, maltotriulose, isomaltotriose, nigerotriose, maltotriose, ketose or combinations thereof. One or more embodiments of a solid substrate can further comprise a melezitose under a substantially dry state. Melezitose can be a non-reducing trisaccharide sugar, having a molecular weight of 504.44 g/mol. In one or more embodiments, the solid substrate can comprise melezitose, wherein a concentration of the melezitose is an amount less than 30%. The melezitose can be impregnated in the substrate; the substrate can also be passively coated or covalently-modified with melezitose. In one or more examples, the substrate is further impregnated with one or more reagents, such as one or more lysis reagents, one or more buffer reagents or one or more reducing agents. In some embodiments, the one or more impregnated reagents comprise cell lytic reagents, biomolecule stabilizing reagents such as protein-stabilizing reagents, protein storage chemicals and combinations thereof impregnated therein under a substantially dry state. Examples of the systems described above and other embodiments are disclosed, .e.g., in US20140234942, the entirety of which is incorporated by reference.

Other substrates for stabilizing proteins can comprise a solid paper based matrix comprising cellulose fibers and/or glass fibers and a hydrophilic or water soluble branched carbohydrate polymer. Surface weight of the solid based matrix can be 40-800 g/m$^2$. Hydrophilic or water soluble branched carbohydrate polymer can be 4-30 wt % of the matrix. The hydrophilic or water soluble branched carbohydrate polymer can have an average molecular weight of 15-800 kDa, such as 20-500 kDa. The branched carbohydrate polymer can include a dextran. Dextrans can be branched (16)-linked glucans. The branched carbohydrate polymer can comprise a copolymer of a mono- or disaccharide with a bifunctional epoxide reagent. Such polymers can be highly branched due to the multitude of reactive hydroxyl groups on each mono/disaccharide. Depending on the reaction conditions used, the degree of branching can be from about 0.2 up to almost 1. The content of water extractables in said paper can be 0-25 wt %, e.g., 0.1-5 wt % or 3-20 wt %. Very low amounts of extractables can be achieved when the carbohydrate polymer is covalently coupled to the paper fibers and/or crosslinked to itself. In some embodiments, the paper comprises 5-300 micromole/g, e.g., 5-50, 5-100 or 50-300 micromole/g negatively or positively charged groups. Negatively charged groups can be e.g. carboxylate groups, sulfonate groups or sulfate groups, while positively charged groups can be e.g. amine or quaternary ammonium groups. The presence of these groups can improve the protective effect of the branched carbohydrate polymer.

Methods for removing sample can comprise a step of storing the dried paper with the sample, e.g., biological sample for at least one week, such as at least one month or at least one year. In some embodiments the method comprises a step of extracting at least one protein from said paper after storage and analyzing said protein. The extraction can be made e.g. by punching out a small part of the paper with dried sample and immersing these in an aqueous liquid. In some embodiments the protein is analyzed in step by an immunoassay, by mass spectrometry or an enzyme activity assay. An example of the substrate disclosed above is disclosed, e.g., in US Appn. No. US20140302521.

The sample stabilization component can comprise at least one dried sample, e.g., at least one dried biological sample, such as a dried blood sample. Blood and other biological materials, e.g. serum, plasma, urine, cerebrospinal fluid, bone marrow, biopsies etc. can be applied to the sample stabilization component and dried for storage and subsequent analysis or other use. The dried sample, e.g., biological sample can be a pharmaceutical formulation or a diagnostic reagent, comprising at least one protein or other sensitive biomolecule. In another aspect the sample stabilization component can comprise a paper card, with one or more sample application areas printed or otherwise indicated on the card. There can be indicator dyes in these areas to show if a non-colored sample has been applied or not. The device can also include a card holder, to e.g. facilitate automated handling in racks etc. and it can include various forms of sampling features to facilitate the collection of the sample.

Other examples of stabilization matrix or stabilization components that can be used in the devices herein include, but are not limited to Gentegra-RNA, Gentegra-DNA (Gentegra, Pleasanton Calif.), as further illustrated in U.S. Pat. No. 8,951,719; DNA Stable Plus, as further illustrated in U.S. Pat. No. 8,519,125; RNAgard Blood System (Biomatria, San Diego, Calif.).

In some embodiments, the solid matrix can selectively stabilize blood plasma components. Plasma components can include cell-free DNA, cell-free RNA, protein, hormones, and other metabolites, which can be selectively stabilized on the solid matrix. Plasma components can be isolated from whole blood and stabilized on a solid matrix. A solid matrix can be overlapping with or a component of a variety of different devices and techniques. Plasma components can be separated from whole blood samples using a variety of different devices and techniques. Techniques can include lateral flow assays, vertical flow assays, and centrifugation.

A solid matrix can be integrated with or a component of a variety of plasma separation devices or techniques. A solid matrix can be overlapping with or a component of a variety of different devices, such as a plasma separation membrane for example Vivid™ plasma separation membrane. A solid matrix can partially overlap with plasma separation device such as a plasma separation membrane. Examples of devices and techniques for plasma separation are disclosed in patents or patent publications, herein incorporated by reference, including U.S. Pat. Nos. 6,045,899; 5,906,742; 6,565,782; 7,125,493; 6,939,468; EP 0,946,354; EP 0,846,024; U.S. Pat. Nos. 6,440,306; 6,110,369; 5,979,670; 5,846,422; 6,277,281; EP 1,118,377; EP 0,696,935; EP 1,089,077, US 20130210078, US 20150031035.

In various devices and techniques, a separation membrane can be used. The separation membrane can be comprised of polycarbonate, glass fiber, or others recognized by one having skill in the art. Membranes can comprise a solid matrix. Membranes can have variable pore sizes. Separation membranes can have pore diameters of about 1 μm, about 2 μm, about 4 μm, about 6 μm, about 8 μm, about 10 μm, about 12 μm, about 14 μm, about 16 μm, about 18 μm, about 20 μm. A separation membrane can have pores with diameters of about 2 μm to about 4 μm. A separation membrane can have pores that are about 2 μm in diameter.

Plasma separation can be implemented for a wide variety of sample volumes. Plasma sample volumes can be variable depending on the application for which a solid matrix is used. Sample volumes can be greater than about 100 μL, about 150 μL, about 200 μL, about 250 μL, about 300 μL, about 350 μL, about 400 μL, about 450 μL, about 500 μL, about 550 μL, about 600 μL, about 650 μL, about 700 μL, about 750 μL, about 800 μL, about 850 μL, about 900 μL, about 950 μL, or about 1000 μL. Sample volumes can range from about 250 μL to about 500 μL.

Preparation of Bio-Components

In some embodiments the user or operator can remove components of the system for analysis, for example before sending the sample off to a facility for analysis. The facility can be a CLIA facility, a laboratory, medical office or external dedicated facility. At facility, the samples can be used in any diagnostic tests including but not limited to common panels, thyroid tests, cancer diagnostic tests, tests and screens for cardiovascular disease, genetic diseases/prenatal testing and infectious disease. A non-limiting list of applicable tests is herein included as FIG. 7 with this filing.

The devices and systems for acquiring, collecting, separating and stabilizing samples can be modular; comprising distinct compartments or components. The distinct components can or can not be easily removed or separated.

Separable or removable components can include the sample substrate, or a sample separation component.

The devices herein (e.g., sample acquisition components and sample stabilization component) can be transported together to a laboratory for further analysis, e.g., of the bio-components. Alternatively, the stabilization component (e.g., substrate or substrate) can be shipped without a sample acquisition component to a laboratory for further analysis of the bio-components. In some instances, treatment and analysis can be performed on the deployed device, systems or substrate, and either the stabilization component or a component of the device or system can be transported to a healthcare provider or other party interested in the results of the test. Once a bio-sample is received at a location for analysis, the substrate, or components of the sample separation component can be removed. These components can be tagged and/or labeled to indicate the composition or target component that is stabilized on the matrix. Using the tag as an identifier the membranes or substrates can be sorted and prepared for the target test.

Systems and processes for receiving and processing the samples can vary depending on the identity, stability, source or other features of the deployed samples. The quality of a bio-sample component can directly impact the quality, reproducibility and reliability of a diagnostic test result. The aforementioned systems, devices, and methods for sample acquisition, collection, stabilization, and optional separation, can impact the sample composition, stability, concentration, and processing. For example the volume, size, quantity, stability and purity of a bio-sample can vary depending on the sample source and the components used to collect the sample. The quality of the samples and by extension the quality of the diagnostic results can be specific the kits, systems, devices and methods for acquiring the sample; therefore, methods, kits, and systems are also disclosed for receiving, processing, treating and/or preparing components of the bio-sample prior to analysis.

Components processed from the sample can include but are not limited to DNA/RNA including cell-free DNA and circulating-tumor DNA, proteins, antigens, antibodies, lipids including HDL/LDL, and any combination thereof. The bio-sample or target components can be extracted using any of the conventional nucleic acid extraction methods. Non-limiting examples of extraction methods that can include but are not limited to, electroelution, gelatin extraction, silica or glass bead extraction, guanidine-thiocyanate-plienol solution extraction, guanidinium thiocyanate acid-based extraction, centrifugation through sodium iodide or similar gradient, centrifugation with buffer, or phenol-chloroform-based extraction. For nucleic acid analysis the extraction step can help remove impurities such as proteins and concentrate the circulating nucleic acids, Extracted circulating nucleic acids can be inspected using methods such as agarose gel electrophoresis, spectrophotometry, fluorometry, or liquid chromatography.

DNA or nucleotides extracted from the sample can be prepared at a lab facility using various methods for reducing error and producing significant signal with limited sample size. Nucleic acid samples can be treated or subjected to various methods for efficient amplification of the desired target nucleic acid (e.g., "DNA template" or "nucleic acid template"). Modified primers can be designed to minimize or prevent the production of unwanted primer-dimers and chimeric products observed with other nucleic acid amplification methods and kits. Novel primer design methods can avoid the production of spurious nucleic acid amplification products. The methods and kits described used for analyzing the sample can comprise "AT GenomiPhi," ATGenomiPhi can use modified hexamers are of the general formula: +N+N(atN)(atN)(atN)*N, wherein "+" precedes an LNA base, as described above, and (atN) represents a random mixture of 2-amino-dA, dC, d(i, and 2-thio-dT. Other hexamers can comprise the formula (atN)(atN)(atN)(atN)(atN)*N, wherein the notations are consistent between these two hexamer designs. The use of these hexamers in nucleic acid amplification techniques can address, minimize or eliminate the problems associated with the production of primer-dimer formation and chimeric nucleic acids observed in traditional methods by inhibiting the ability of the random hexamers to anneal with one another, by increasing the melting $T_m$ of the primers, improving the binding efficiency of the hexamer to the target nucleic acid via the addition of LNAs and 2-amino-dA to the primers, and preventing annealing of the target DNA to itself through the incorporation of 2-thio-dT into the random hexamers. Moreover, the primer modifications can increase their binding strength to the target nucleic acid and permit the utilization of more stringent hybridization buffers that further minimize the likelihood of the production of primer-dimers and chimeric nucleic acid products. These and other methods of DNA amplification methods can be found, e.g., in US Appn. No. US20130210078.

DNA derived from a sample can be analyzed using one or more methods for generating single-stranded DNA circles from a biological sample. The laboratory analyzing the sample can use a method comprising the steps of: treating the biological sample with an extractant to release nucleic acids, thereby forming a sample mixture; neutralizing the extractant; denaturing the released nucleic acids to generate single-stranded nucleic acids; and contacting the single-stranded nucleic acids with a ligase that is capable of template-independent, intramolecular ligation of a single-stranded DNA sequence to generate single-stranded DNA circles. The steps of the method can be performed without any intermediate nucleic acid isolation or nucleic acid purification. In certain embodiments, the steps can be performed in a sequential manner in a single reaction vessel. In certain embodiments, the single-stranded DNA circles can be amplified to enable subsequent analysis of the biological sample. In certain embodiments, the sample mixture can be dried on solid matrix prior to the neutralizing step. In certain embodiments, damage to the DNA can be repaired enzymatically prior to the denaturing step. In other aspects, a method is provided for analyzing a sample, e.g., biological sample. Thus, the single-stranded DNA circles generated according to certain embodiments of the method are amplified, and the amplification product is analyzed. The analysis can be performed by, for example, targeted sequencing of the amplified product. In another aspect, a method is provided for detecting chromosomal rearrangement breakpoints from a biological sample. Thus, the single-stranded DNA circles generated according to certain embodiments described herein are amplified, and the amplification product is analyzed, e.g., by sequencing. Any chromosomal rearrangement breakpoints can be identified by comparing the sequences to a known reference sequence. In yet another aspect, a kit can be provided that comprises an extractant for treating a biological sample to release nucleic acids; a reagent for neutralizing the extractant; and a ligase that is capable of template-independent, intramolecular ligation of a single-stranded DNA sequence. These and other method of DNA amplification methods can be found, e.g., in PCT Appn. No. WO US2015/50760.

Methods for generating a single-stranded DNA circle from a linear DNA can be used on the collected sample. The methods can comprise steps for providing a linear DNA, end-repairing the linear DNA by incubating it with a polynucleotide kinase in the presence of a phosphate donor to generate a ligatable DNA sequence having a phosphate group at a 5' terminal end and a hydroxyl group at a 3' terminal end, and performing an intra-molecular ligation of the repaired, ligatable DNA sequence with a ligase in order to generate the single-stranded DNA circle. Steps can be performed in a single reaction vessel without any intervening isolation or purification steps. The phosphate donor can be a guanosine triphosphate (GTP), a cytidine triphosphate (CTP), a uridine triphosphate (UTP), a deoxythymidine triphosphate (dTTP) or a combination thereof. The linear DNA can either be double-stranded or single-stranded DNA. DNA can be a segment of fragmented DNA such as circulating DNA. The ligatable DNA, if in double-stranded form, can need to be denatured prior to intra-molecular ligation reaction. A pre-adenylated ligase that is capable of template-independent, Ultra-molecular ligation of single-stranded DNA sequences can be employed for the ligation reaction. In other embodiments, the method for generating a single-stranded DNA circle from a linear DNA can employ a DNA pre-adenylation step prior to an intra-molecular ligation step. The linear DNA can optionally be incubated with a polynucleotide kinase in the presence of adenosine triphosphate (ATP) to generate a ligatable DNA sequence that comprises a phosphate group at a 5' terminal end and a hydroxyl group at a 3' terminal end. Generation of a ligatable DNA sequence from the linear DNA can be preferred if the linear DNA is in a highly fragmented form. The linear DNA or the ligatable DNA sequence can then be incubated with an adenylating enzyme in presence of ATP to generate a 5' adenylated DNA sequence. The 5' adenylated DNA sequence can be incubated with a non-adenylated ligase, which is capable of template-independent intra-molecular ligation of the 5' adenylated DNA sequence to generate the single-stranded DNA circle. All steps of the method can be performed in a single reaction vessel without any intervening isolation or purification steps. ATP can be removed from the reaction mixture (e.g, by treating the reaction mixture with a phosphatase) before the intra-molecular ligation reaction if the non-adenylated ligase is an ATP-dependent ligase. If the 5' adenylated DNA is in double-stranded form, it can need to be denatured prior to the intra-molecular ligation reaction. These and other method of DNA circularization and amplification methods can be found, e.g., in US Appn. No. US20150031086.

Sample treatment can involve steps to prepare RNA for analysis. The methods can involve the production of a nucleic acid structure and its subsequent use in the purification and amplification of nucleic acid. The methods can require a DNA sequence that comprises a double stranded region and a single stranded region. The single stranded region can be complementary to the RNA sequence of interest. The RNA sequence can then hybridized to the single stranded region of the DNA sequence and then the two sequences can be ligated to produce an RNA-DNA molecule. Methods can include steps whereby the 3' end of RNA is ligated to a double stranded DNA oligonucleotide containing a promoter sequence. This double stranded DNA oligonucleotide can contain a promoter for RNA polymerase within the double stranded region that is followed by a segment of single stranded DNA forming a 3' overhang. When the 3' overhang contains a string of thymidine residues, the single stranded portion of the double stranded DNA can hybridize to the 3' end of messenger RNA (mRNA) poly(A) tails. After the addition of ligase mRNA can have one strand of double stranded DNA sequence ligated to the 3' end. When an RNA polymerase is added, the RNA-DNA hybrid molecules can be efficiently transcribed to synthesize cRNA. As transcription reactions using RNA polymerase can transcribe each template multiple times, this method can allow for effective RNA amplification. Another method similar to that described above can involve the ligation of the DNA oligonucleotide to the RNA as described. However, the DNA oligonucleotide can either attach to a solid support or contain an affinity tag. This can allow for very efficient covalent attachment and/or capture of RNA molecules, which can be used for any of a variety of purposes. Additional methods can utilize ligation and subsequent transcription to create complementary RNA containing a user-defined sequence at the 5' end of the cRNA. This sequence "tag" can be placed between the RNA polymerase promoter and the 3' end of the ligated RNA molecule. The user-defined sequence can be used for purification or identification or other sequence specific manipulations of cRNA. If cRNA product is subsequently ligated and re-amplified according to the described method, the resulting doubly-amplified product can be "sense", with respect to the original sense template and this new product can have two separate user-defined sequences located at the 5' ends. These sequences can be used for synthesis of cDNA, allowing for full-length synthesis and directional cloning. Those skilled in the art will understand that either with or without the user defined sequences this double amplification method can provide a significant increase in RNA quantity, allowing for analysis of samples previously too small for consideration. These and other methods for amplification of DNA fragments can be found, e.g., in US Appn. No. US20080003602.

Additional methods for analysis of the bio-sample can focus on nucleic acids present in a region of interest in a biological sample, and provide protein expression information for many proteins as well as add to the DNA sequence information. Additional methods for sample analysis can focus on homogeneous subsection of a heterogeneous sample. Specific subpopulations of cells within mixed populations can be accurately identified from predetermined selection criteria and analyzed. Mutations can be identified, which can be useful for diagnosis and/or prognosis or for further investigation of drug targets. These and other methods for DNA amplification can be found, e.g., in PCT Appn. No. US2015/50760.

Elution of Nucleic Acids

In some cases, nucleic acids, e.g., DNA or RNA, in a sample (e.g., a biological sample), are applied to a stabilization matrix (e.g., nucleic acid stabilization matrix), the sample is optionally dried on the stabilization matrix, and the nucleic acid on the stabilization matrix, e.g., DNA or RNA, are eluted from the stabilization matrix. In some instances, a dried biological sample is stabilized on a stabilization matrix capable of stabilizing a nucleic acid, e.g., as described herein. In some instances, a method comprises the steps of: (a) contacting, e.g., spotting a sample, e.g., a biological sample, comprising a nucleic acid, e.g., DNA or RNA, on a nucleic acid stabilization matrix, (b) optionally drying the sample, e.g., biological sample, on the nucleic acid stabilization matrix, (c) optionally contacting the nucleic acid stabilization matrix comprising nucleic acid with a lysis buffer, (d) optionally contacting the nucleic acid stabilization matrix comprising nucleic acid with a nucleic acid binding buffer (optionally containing an organic solvent), e.g., by submerging the nucleic acid stabilization matrix comprising nucleic acid in the binding buffer; (e) optionally contacting the nucleic acid stabilization matrix comprising nucleic acid with a wash buffer, e.g., by submerging the nucleic acid stabilization matrix in the wash buffer, and (f) contacting the nucleic acid stabilization matrix comprising nucleic acid with an elution buffer, e.g., by submerging the nucleic acid stabilization matrix comprising nucleic acid in the elution buffer, to elute the nucleic acid from the stabilization matrix.

In some cases, nucleic acid, e.g., RNA or DNA, can be extracted from a stabilization matrix, e.g., a paper stabilization matrix, e.g., using an extraction buffer. The extracted nucleic acid, e.g., RNA or DNA, can be bound to a second matrix, e.g., a second solid support, e.g., beads, e.g., magnetic beads. The binding to a second matrix, e.g., a second solid support, e.g., beads, e.g., magnetic beads, can occur in a binding buffer. Nucleic acid, e.g., RNA or DNA, on the second matrix can be washed with one or more wash buffers. Nucleic acid on the second matrix can be treated with an enzyme solution comprising, e.g., a DNase, RNase, or protease, to degrade a specific type of molecule (e.g., RNA, DNA, or protein). Nucleic acid on the solid matrix can be eluted from the solid matrix using, e.g., an elution buffer.

The elution can be performed on at least a portion of the stabilization matrix comprising a sample, e.g., a dried biological sample. In some cases, a portion of the stabilization matrix can be separated from the rest of the stabilization matrix, e.g., a portion of a stabilization matrix can be punched out of the stabilization matrix, and nucleic acids in the separated portion can be eluted. The punches can be about 0.5, 1, 2, 3, 4, 5, 6, 7, 8, 9, 10, 15, 20, 25, 30, 35, 40, 45, 50, 55, or 60 mm in diameter. The punches can be from about 10 to about 60, from about 10 to about 50, from about 10 to about 40, from about 10 to about 30, from about 10 to about 20, from about 1 to about 10, from about 2 to about 9, from about 3 to about 8, from about 4 to about 7, from about 5 to about 6, from about 3 to about 6, from about 1 to about 4, from about 1 to about 3, or from about 1 to about 2 mm in diameter. In some cases, a stabilization matrix comprising nucleic acid is not separated into portions before the nucleic acid is eluted from the stabilization matrix.

In some cases, a nucleic acid stabilization matrix comprising nucleic acid can be contacted with a lysis buffer. In some cases, the binding and retention of a nucleic acid to a stabilization matrix can be enhanced through contacting the stabilization matrix with a binding buffer. In some cases, a portion of the stabilization matrix is contacted with a nucleic acid binding buffer. In some instances, the nucleic acid binding buffer can comprise beads. In some cases, the stabilization matrix is contacted with a wash buffer, e.g., to remove impurities. In some instances, the nucleic acid can be eluted by contacting the stabilization matrix with an elution buffer.

In some instances, the nucleic acid lysis buffer, binding buffer, wash buffer, or elution buffer can comprise a commercially available buffer. For instance, a buffer can comprise TRIzol® manufactured by Thermofisher®, Buffer RLT manufactured by Qiagen®, Buffer RLN manufactured by Qiagen®, RNA Lysis Buffer (RLA) manufactured by Promega, PureYield™ Cell Lysis Solution (CLA) manufactured by Promega, PureYield™ Endotoxin Removal Wash manufactured by Promega, PureZOL™ RNA isolation reagent (Bio-Rad™), RNA Lysis Buffer or DNA/RNA Binding Buffer manufactured by Zymo Research Corp, or RNA Capture Buffer manufactured by Pierce™.

In some instances, the nucleic acid lysis buffer, binding buffer, wash buffer, or elution buffer can comprise one or more buffering agents (or pH buffer), one or more salts, one or more reducing agents, one or more chelators, one or more surfactants, one or more enzymes, one or more protein denaturants, one or more blocking reagents, one or more organic solvents, or any combination thereof. For example, the nucleic acid lysis buffer, binding buffer, wash buffer, or elution buffer can comprise one or more protein denaturants and one or more reducing agents. The nucleic acid lysis buffer, binding buffer, wash buffer, or elution buffer can comprise can comprise one or more protein denaturants, one or more reducing agents, and one or more enzymes. The nucleic acid lysis buffer, binding buffer, wash buffer, or elution buffer can comprise one or more buffering agents, one or more protein denaturants, one or more reducing agents, and one or more enzymes. The nucleic acid lysis buffer, binding buffer, wash buffer, or elution buffer can comprise one or more salts and one or more buffers. The nucleic acid lysis buffer, binding buffer, wash buffer, or elution buffer can comprise one or more salts, one or more buffers, and one or more organic solvents. The nucleic acid lysis buffer, binding buffer, wash buffer, or elution buffer can comprise one or more buffers and one or more enzymes. The nucleic acid lysis buffer, binding buffer, wash buffer, or elution buffer can comprise one or more buffers and one or more chelating agents. The nucleic acid lysis buffer, binding buffer, wash buffer, or elution buffer can comprise one or more buffers, one or more chelating agents, and one or more organic solvents.

The one or more buffering agents can be, e.g., saline, citrate, phosphate, phosphate buffered saline, acetate, glycine, tris(hydroxymethyl)aminomethane (tris) hydrochloride, tris buffered saline (TBS), 34[1,3-dihydroxy-2-(hydroxymethyl)propan-2-yl]aminolpropane-1-sulfonic acid (TAPS), bicine, tricine, 34[1,3-dihydroxy-2-(hydroxymethyl)propan-2-yl]amino1-2-hydroxypropane-1-sulfonic acid (TAPSO), 4-(2-hydroxyethyl)-1-piperazineethanesulfonic acid (HEPES), piperazine-N,N'-bis(2-ethanesulfonic acid) (PIPES), 3-(N-morpholino)propanesulfonic acid (MOPS), 2-(N-morpholino)ethanesulfonic acid (MES), 2-[[1,3-dihydroxy-2-(hydroxymethyl)propan-2-yl]amino] ethanesulfonic acid (TES), cacodylate, glycine, carbonate, or any combination thereof. The one or more buffering agents can be present at a concentration of from about 0.1 mM to about 500, from about 0.1 mM to about 400 mM, from about 0.1 mM to about 300 mM, from about 0.1 mM to about 200 mM, from about 0.1 mM to about 100 mM, from about 0.1 mM to about 50 mM, from about 0.1 mM to about 25 mM, from about 0.1 mM to about 20 mM, from about 0.1 mM to about 15 mM, from about 0.1 mM to about 10 mM, from about 0.1 mM to about 5 mM, from about 0.1 mM to about 4 mM, from about 0.1 mM to about 3 mM, from about 0.1 mM to about 2 mM, from about 0.1 mM to about 1 mM, from about 0.1 mM to about 0.9 mM, from about 0.1 mM to about 0.8 mM, from about 0.1 mM to about 0.7 mM, from about 0.1 mM to about 0.6 mM, from about 0.1 mM to about 0.5 mM, from about 0.1 mM to about 0.4 mM, from about 0.1 mM to about 0.3 mM, or from about 0.1 mM to about 0.2 mM. The buffering agent can be present at a concentration of less than 500 mM, less than 400 mM, less than 300 mM, less than 200 mM, less than 100 mM, less than 50 mM, less than 25 mM, less than 20 mM, less than 15 mM, less than 10 mM, less than 5 mM, less than 4 mM, less than 3 mM, less than 2 mM, less than 1 mM, less than 0.9 mM, less than 0.8 mM, less than 0.7 mM, less than 0.6 mM, less than 0.5 mM, less than 0.4 mM, less than 0.3 mM, less than 0.2 mM, or less than 0.1 mM. The buffering agent can be present at a concentration of more than 500 mM, more than 400 mM, more than 300 mM, more than 200 mM, more than 100 mM, more than 50 mM, more than 25 mM, more than 20 mM, more than 15 mM, more than 10 mM, more than 5 mM, more than 4 mM, more than 3 mM, more than 2 mM, more than 1 mM, more than 0.9 mM, more than 0.8 mM, more than 0.7 mM, more than 0.6 mM, more than 0.5 mM, more than 0.4 mM, more than 0.3 mM, more than 0.2 mM, or more than 0.1 mM.

The one or more salts can be, e.g., sodium chloride, sodium acetate, sodium bicarbonate, sodium bisulfate, sodium bromide, potassium chloride, potassium acetate, potassium bicarbonate, potassium bisulfate, potassium bromate, potassium bromide, or potassium carbonate. The one or more salts can be at a concentration of about 0.1 mM, 5 mM, 10 mM, 25 mM, 50 mM, 100 mM, 250 mM, 500 mM, 750 mM, or 1000 mM in a buffer. The one or more salts can be at a concentration of less than 0.1 mM, 5 mM, 10 mM, 25 mM, 50 mM, 100 mM, 250 mM, 500 mM, 750 mM, or 1000 mM in a buffer. The one or more salts can be at a concentration of at least 0.1 mM, 5 mM, 10 mM, 25 mM, 50 mM, 100 mM, 250 mM, 500 mM, 750 mM, or 1000 mM.

The one or more reducing agents can be, e.g., beta-mercaptoethanol (BME), 2-aminoethanethiol (2MEA-HCl (cysteamine-HCl)), dithiothreitol (DTT), glutathione (GSH), tris(2-carboxyethyl)phosphine (TECP), or any combination thereof. The concentration of the one or more reducing agents can be about 0.1 mM, 0.5 mM, 1 mM, 10 mM, 50 mM, 100 mM, 250 mM, or 500 mM. The concentration of the one or more reducing agents can be less than 0.5 mM, 1 mM, 10 mM, 50 mM, 100 mM, 250 mM, or 500 mM. For example, the concentration of DTT can be from about 0.05 mM to about 100 mM, from about 0.5 mM to about 50 mM, or from about 5 mM to about 10 mM. The concentration of TCEP can be from about 0.05 mM to about 50 mM, from about 0.5 mM to about 50 mM, or from about 0.5 mM to about 5 mM. The concentration of BME can be from about 0.05% to about 10%, from about 0.5% to about 5%, or from about 1% to about 10%. The concentration of GSH can be from about 0.05 mM to about 25 mM, from about 0.5 mM to about 10 mM, or from about 5 mM to about 10 mM. The concentration of the one or more reducing agents can be about 1 mM, 10 mM, 50 mM, 100 mM, 250 mM, or 500 mM.

The one or more chelators can be, e.g., a carbohydrate; a lipid; a steroid; an amino acid or related compound; a phosphate; a nucleotide; a tetrapyrrol; a ferrioxamines; an ionophor; a phenolic; or a synthetic chelator such as 2,2'-bipyridyl, dimercaptopropanol, ethylenediaminetetraacetic acid (EDTA), ethylenedioxy-diethylene-dinitrilo-tetraacetic acid, ethylene glycol-bis-(2-aminoethyl)-N,N,N', N'-tetraacetic acid (EGTA), a metal nitrilotriacetic acid (NTA), salicylic acid, or triethanolamine (TEA). The concentration of the one or more chelating agents in a buffer can be about 0.1 mM, 1 mM, 5 mM, 10 mM, 20 mM, or 25 mM. The concentration of the one or more chelating agents in a buffer can be less than 0.1 mM, 1 mM, 5 mM, 10 mM, 20 mM, or 25 mM. The concentration of the one or more chelating agents in a buffer can be more than 0.1 mM, 1 mM, 5 mM, 10 mM, 20 mM, or 25 mM.

The one or more surfactants can be, e.g., an anionic, cationic, nonionic or amphoteric type. The one or more surfactants can be polyethoxylated alcohols; polyoxyethylene sorbitan; octoxynol such as Triton X 100™ (polyethylene glycol p-(1,1,3,3-tetramethylbutyl)-phenyl ether); polysorbates such as Tween™ 20 ((e.g., polysorbate 20) or Tween™ 80 (polysorbate 80); sodium dodecyl sulfate; sodium lauryl sulfate; nonylphenol ethoxylate such as Tergitol™; cyclodextrins; or any combination thereof. The one or more surfactants can be present at a concentration of less than 0.001%, less than 0.005%, less than 0.01%, less than 0.015%, less than 0.02%, less than 0.025%, less than 0.03%, less than 0.035%, less than 0.04%, less than 0.045%, less than 0.05%, less than 0.055%, less than 0.06%, less than 0.065%, less than 0.07%, less than 0.075%, less than 0.08%, less than 0.085%, less than 0.09%, less than 0.095%, less than 0.1%, less than 0.15%, less than 0.2%, less than 0.25%, less than 0.3%, less than 0.35%, less than 0.4%, less than 0.45%, less than 0.5%, less than 0.55%, less than 0.6%, less than 0.65%, less than 0.7%, less than 0.75%, less than 0.8%, less than 0.85%, less than 0.9%, less than 0.95%, or less than 0.1% by volume relative to the total volume of the elution buffer. The one or more surfactants can be at a concentration of about 0.01%, 0.05%, 0.1%, 0.5%, 1%, 5%, or 10%. The one or more surfactants can be at a concentration of less than 0.01%, 0.05%, 0.1%, 0.5%, 1%, 5%, or 10%. The one or more surfactants can be at a concentration of more than 0.01%, 0.05%, 0.1%, 0.5%, 1%, 5%, or 10%.

The one or more protein denaturants can be, e.g., a chaotropic agent, e.g., a chaotropic salt. A chaotropic agent can be butanol, ethanol, guanidine chloride, guanidine hydrochloride, guanidine isothiocyanate, lithium perchlorate, lithium acetate, magnesium chloride, phenol, propanol, sodium iodide, sodium thiocyanate, thiourea, urea, or any combination thereof. The concentration of the chaotropic agent in a buffer can be about 0.1 mM, 1 mM, 10 mM, 100 mM, 1 M, 6 M, or 8 M. The concentration of the chaotropic agent in a buffer can be at least 0.1 mM, 1 mM, 10 mM, 100 mM, 1 M, 6 M, or 8 M. The concentration of the chaotropic agent in a buffer can be less than 0.1 mM, 1 mM, 10 mM, 100 mM, 1 M, 6 M, or 8 M.

The nucleic acid lysis buffer, binding buffer, wash buffer or elution buffer can further comprise one or more enzymes. A lysis buffer, binding buffer, wash buffer or elution buffer can comprise DNase or RNase in amounts sufficient to remove DNA or RNA impurities, respectively, from each other. A lysis buffer, binding buffer, wash buffer or elution buffer can comprise lysis enzymes such as hen egg white lysozyme, T4 lysozyme and the like, as well as enzymes such as carbohydrases, phytases, and proteases such as trypsin, Proteinase K, pepsin, chymotrypsin, papain, bromelain, subtilisin, or elastase. A protease can be a serine protease, a cysteine protease, a threonine protease, an aspartic protease, a glutamic protease, or a metalloprotease, or an asparagine peptide lyase.

The nucleic acid lysis buffer, binding buffer, wash buffer or elution buffer can be an aqueous solution having a pH from about 2 to about 10, from about 2 to about 9, from about 2 to about 8, from about 2 to about 7, from about 2 to about 6, from about 2 to about 5, from about 2 to about 4, or from about 2 to about 3. The nucleic acid lysis buffer, binding buffer, wash buffer or elution buffer can be an aqueous solution having a pH from about 6 to about 8, from about 6 to about 7.9, between about 6 to about 7.8, between about 6 to about 7.7, between about 6 to about 7.6, between about 6 to about 7.5, between about 6 to about 7.4, between about 6 to about 7.3, from about 6 to about 7.2, from about 6 to about 7.1, from about 6 to about 7, from about 6 to about 6.9, from about 6 to about 6.8, from about 6 to about 6.7, from about 6 to about 6.6, from about 6 to about 6.5, from about 6 to about 6.4, from about 6 to about 6.3, from about 6 to about 6.2, or from about 6 to about 6.1. The nucleic acid lysis buffer, binding buffer, wash buffer or elution buffer can be an aqueous solution having a pH of at least about 3, at least about 4, at least about 5, at least about 6, at least about 7, at least about 8, at least about 9, or at least about 10.

The nucleic acid lysis buffer, binding buffer, wash buffer, or elution buffer can further comprise additional ingredients. For example, a lysis buffer, binding buffer, wash buffer, or elution buffer can comprise a protein blocking agent that minimizes non-specific binding such as bovine serum albumin, fetal bovine serum, and the like. A lysis buffer, binding buffer, wash buffer, or elution buffer can comprise additional nucleic acids (to include DNA or RNA) from an organism distinct from the subject such as bacterial DNA, bacterial DNA, yeast DNA, yeast RNA, mammalian nucleic acids including primate nucleic acids such as human or chimpanzee DNA, or non-mammalian nucleic acids including nucleic acids from fish such as herring, mackerel, krill, or salmon DNA and the like.

A lysis buffer, binding buffer, wash buffer, or elution buffer can comprise an amount of one or more organic solvents, e.g., to enhance binding of a nucleic acid to the stabilization matrix. The one or more organic solvents can be methanol, ethanol, DMSO, DMF, dioxane, tetrahydrofuran, propanol, isopropanol, butanol, t-butanol, or pentanol, acetone and the like. In some instances, a binding buffer can comprise less than 0.01%, less than 0.05%, less than 0.1%, less than 0.15%, less than 0.2%, less than 0.25%, less than 0.3%, less than 0.35%, less than 0.4%, less than 0.45%, less than 0.5%, less than 0.55%, less than 0.6%, less than 0.65%, less than 0.7%, less than 0.75%, less than 0.8%, less than 0.85%, less than 0.9%, less than 0.95%, less than 1%, less than 1.5%, less than 2%, less than 2.5%, less than 3%, less than 3.5%, less than 4%, less than 4.5%, less than 5%, less than 5.5%, less than 6%, less than 6.5%, less than 7%, less than 7.5%, less than 8%, less than 8.5%, less than 9%, less than 9.5%, less than 10%, less than 11%, less than 12%, less than 13%, less than 14%, less than 15%, less than 16%, less than 17%, less than 18%, less than 19%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 99%, or 100% of an organic solvent by volume relative to the total volume of the solution. The organic solvent can be at a concentration of at least 0.1%, 1%, 10%, 50%, 75%, or 100%. The organic solvent can be at a concentration of about 0.1%, 1%, 10%, 50%, 75%, or 100%.

The stabilization matrix, or the portion of the stabilization matrix, can be contacted with a volume of the nucleic acid binding buffer, wash buffer or elution buffer of less than 5 µL, less than 10 µL, less than 15 µL, less than 20 µL, less than 25 µL, less than 30 µL, less than 35 µL, less than 40 µL, less than 45 µL, less than 50 µL, less than 55 µL, less than 60 µL, less than 65 µL, less than 70 µL, less than 75 µL, less than 80 µL, less than 85 µL, less than 90 µL, less than 95 µL, less than 100 µL, less than 110 µL, less than 120 µL, less than 130 µL, less than 140 µL, less than 150 µL, less than 160 µL, less than 170 µL, less than 180 µL, less than 190 µL, less than 200 µL, less than 250 µL, less than 300 µL, less than 350 µL, less than 400 µL, less than 450 µL, less than 500 µL, less than 550 µL, less than 600 µL, less than 650 µL, less than 700 µL, less than 750 µL, less than 800 µL, less than 850 µL, less than 900 µL, less than 950 µL, less than 1,000 µL, less than 1.5 mL, less than 2 mL, less than 2.5 mL, less than 3 mL, less than 3.5 mL, less than 4 mL, less than 4.5 mL, less than 5 mL, less than 5.5 mL, less than 6 mL, less than 6.5 mL, less than 7 mL, less than 7.5 mL, less than 8 mL, less than 8.5 mL, less than 9 mL, less than 9.5 mL, or less than 10 mL. The stabilization matrix, or portion of the stabilization matrix, can be contacted with about 0.1 mL, 0.2 mL, 0.5 mL, 0.7 mL, 1 mL, 2 mL, 5 mL, 7 mL, or 10 mL of buffer. The stabilization matrix, or portion of the stabilization matrix, can be contacted with at least 0.1 mL, 0.2 mL, 0.5 mL, 0.7 mL, 1 mL, 2 mL, 5 mL, 7 mL, or 10 mL of buffer.

The volume of binding buffer, wash buffer, or elution buffer contacted with the stabilization matrix can be dependent on the surface area of the stabilization matrix. The amount of binding buffer, wash buffer, or elution buffer can be less than 1 $\mu L/mm^2$, less than 2 $\mu L/mm^2$, less than 3 $\mu L/mm^2$, less than 4 $\mu L/mm^2$, less than 5 $\mu L/mm^2$, less than 6 $\mu L/mm^2$, less than 7 $\mu L/mm^2$, less than 8 $\mu L/mm^2$, less than 9 $\mu L/mm^2$, less than 10 $\mu L/mm^2$, less than 12 $\mu L/mm^2$, less than 14 $\mu L/mm^2$, less than 16 $\mu L/mm^2$, less than 18 $\mu L/mm^2$, less than 20 $\mu L/mm^2$, less than 25 $\mu L/mm^2$, less than 30 $\mu L/mm^2$, less than 35 $\mu L/mm^2$, less than 40 $\mu L/mm^2$, less than 45 $\mu L/mm^2$, less than 50 $\mu L/mm^2$, less than 55 $\mu L/mm^2$, less than 60 $\mu L/mm^2$, less than 65 $\mu L/mm^2$, less than 70 $\mu L/mm^2$, less than 75 $\mu L/mm^2$, less than 80 $\mu L/mm^2$, less than 85 $\mu L/mm^2$, less than 90 $\mu L/mm^2$, less than 95 $\mu L/mm^2$, less than 100 $\mu L/mm^2$, less than 150 $\mu L/mm^2$, less than 200 $\mu L/mm^2$, less than 250 $\mu L/mm^2$, less than 300 $\mu L/mm^2$, less than 350 $\mu L/mm^2$, less than 400 $\mu L/mm^2$, less than 450 $\mu L/mm^2$, less than 500 $\mu L/mm^2$, less than 550 $\mu L/mm^2$, less than 600 $\mu L/mm^2$, less than 650 $\mu L/mm^2$, less than 700 $\mu L/mm^2$, less than 750 $\mu L/mm^2$, less than 800 $\mu L/mm^2$, less than 850 $\mu L/mm^2$, less than 900 $\mu L/mm^2$, less than 950 $\mu L/mm^2$, or less than 1,000 $\mu L/mm^2$. In some cases, the amount of binding buffer, wash buffer, or elution buffer can be from about 10 $\mu L/mm^2$, to about 1,000 $\mu L/mm^2$, from about 10 $\mu L/mm^2$ to about 900 $\mu L/mm^2$, from about 10 $\mu L/mm^2$ to about 800 $\mu L/mm^2$, from about 10 $\mu L/mm^2$ to about 700 $\mu L/mm^2$, from about 10 $\mu L/mm^2$ to about 600 $\mu L/mm^2$, from about 10 $\mu L/mm^2$ to about 500 $\mu L/mm^2$, from about 10 $\mu L/mm^2$ to about 400 $\mu L/mm^2$, from about 10 $\mu L/mm^2$ to about 300 $\mu L/mm^2$, from about 10 $\mu L/mm^2$ to about 200 $\mu L/mm^2$, from about 10 $\mu L/mm^2$ to about 100 $\mu L/mm^2$, from about 10 $\mu L/mm^2$ to about 90 $\mu L/mm^2$, from about 10 $\mu L/mm^2$ to about 80 $\mu L/mm^2$, from about 10 $\mu L/mm^2$ to about 70 $\mu L/mm^2$, from about 10 $\mu L/mm^2$ to about 60 $\mu L/mm^2$, from about 10 $\mu L/mm^2$ to about 50 $\mu L/mm^2$, from about 10 $\mu L/mm^2$ to about 40 $\mu L/mm^2$, from about 10 $\mu L/mm^2$ to about 30 $\mu L/mm^2$, or from about 10 $\mu L/mm^2$ to about 20 $\mu L/mm^2$.

The lysis, binding, washing or elution of the nucleic acid can be performed in the presence or absence of agitation from an agitation source. An agitation source can be a rocker, vortexer, mixer, shaker and the like. In some cases, an agitation source can be set to a constant speed. The speed can be less than 1 rotations per minute (rpm), less than 5 rpm, less than 10 rpm, less than 15 rpm, less than 20 rpm, less than 25 rpm, less than 30 rpm, less than 35 rpm, less than 40 rpm, less than 45 rpm, less than 50 rpm, less than 55 rpm, less than 60 rpm, less than 65 rpm, less than 70 rpm, less than 75 rpm, less than 80 rpm, less than 85 rpm, less than 90 rpm, less than 95 rpm, less than 100 rpm, less than 150 rpm, less than 200 rpm, less than 250 rpm, less than 300 rpm, less than 350 rpm, less than 400 rpm, less than 450 rpm, less than 500 rpm, less than 550 rpm, less than 600 rpm, less than 650 rpm, less than 700 rpm, less than 750 rpm, less than 800 rpm, less than 850 rpm, less than 900 rpm, less than 950 rpm, less than 1,000 rpm, less than 1,500 rpm, less than 2,000 rpm, less than 2,500 rpm, less than 3,000 rpm, less than 3,500 rpm, less than 4,000 rpm, less than 4,500 rpm, less than 5,000 rpm, less than 5,500 rpm, less than 6,000 rpm, less than 6,500 rpm, less than 7,000 rpm, less than 7,500 rpm, less than 8,000 rpm, less than 8,500 rpm, less than 9,000 rpm, less than 9,500 rpm, or less than 10,000 rpm. The speed can be about 50 rpm 100 rpm, 200 rpm, 300 rpm, 400 rpm, 500 rpm, 600 rpm, 700 rpm, 800 rpm, 900 rpm, 1000 rpm, 1500 rpm, or 5000 rpm. The speed can be at least 50 rpm 100 rpm, 200 rpm, 300 rpm, 400 rpm, 500 rpm, 600 rpm, 700 rpm, 800 rpm, 900 rpm, 1000 rpm, 1500 rpm, or 5000 rpm.

The binding, washing or elution can be performed at a temperature of about 0° C., less than 1° C., less than 2° C., less than 3° C., less than 4° C., less than 5° C., less than 6° C., less than 7° C., less than 8° C., less than 9° C., less than 10° C., less than 11° C., less than 12° C., less than 13° C., less than 14° C., less than 15° C., less than 16° C., less than 17° C., less than 18° C., less than 19° C., less than 20° C., less than 21° C., less than 22° C., less than 23° C., less than 24° C., less than 25° C., less than 26° C., less than 27° C., less than 28° C., less than 29° C., less than 30° C., less than 31° C., less than 32° C., less than 33° C., less than 34° C., less than 35° C., less than 36° C., less than 37° C., less than 38° C., less than 39° C., less than 40° C., less than 45° C., less than 50° C., less than 55° C., less than 60° C., less than 65° C., less than 70° C., less than 75° C., less than 80° C., less than 85° C., less than 90° C., less than 95° C., or about 100° C. In some cases, the binding, washing or elution can be performed at a temperature of from about 10° C. to about 100° C., from about 10° C. to about 95° C., from about 10° C. to about 90° C., from about 10° C. to about 85° C., from about 10° C. to about 80° C., from about 10° C. to about 75° C., from about 10° C. to about 70° C., from about 10° C. to about 65° C., from about 10° C. to about 60° C., from about 10° C. to about 55° C., or from about 10° C. to about 50° C. In some cases, the lysis, binding, washing or elution can be performed at a temperature of from about 20° C. to about 50° C., from about 20° C. to about 48° C., from about 20° C. to about 46° C., from about 20° C. to about 44° C., from about 20° C. to about 42° C., from about 20° C. to about 40° C., from about 20° C. to about 38° C., from about 20° C. to about 36° C., from about 20° C. to about 34° C., from about 20° C. to about 32° C., from about 20° C. to about 30° C., from about 20° C. to about 28° C., from about 20° C. to about 26° C., from about 20° C. to about 24° C., or from about 20° C. to about 22° C. The temperature can be about 10° C., 20° C., 25° C., 30° C., 37° C., 50° C., or 65° C.

The lysis, binding, washing or elution can be performed for less than 1, less than 5, less than 10, less than 15, less than 20, less than 25, less than 30, less than 35, less than 40, less than 45, less than 50, less than 55, or less than 60 minutes. The binding, washing or elution can be performed for less than 0.5, less than 1, less than 1.5, less than 2, less than 2.5, less than 3, less than 3.5, less than 4, less than 4.5, less than 5, less than 5.5, less than 6, less than 6.5, less than 7, less than 7.5, less than 8, less than 8.5, less than 9, less than 9.5, less than 10, less than 10.5, less than 11, less than 11.5, or less than 12 hours, less than 18 hrs, less than 1 day, less than 1.5 days, less than 2 days, less than 2.5 days, less than 3 days, less than 3.5 days, less than 4 days, less than 4.5 days, less than 5 days, less than 5.5 days, less than 6 days, less than 6.5 days, or less than 7 days. The lysis, binding, washing, or elution can be performed for about 0.25 hr, 0.5 hr, 1 hr, 2 hr, 5 hr, 10 hr, 12 hr, 18 hr, 24 hr, 3 days, or 1 week, or more. The lysis, binding, washing, or elution can be performed for at least 0.25 hr, 0.5 hr, 1 hr, 2 hr, 5 hr, 10 hr, 12 hr, 18 hr, 24 hr, 3 days, or 1 week.

The eluted nucleic acid can be transferred to a container for storage or further processing, or can be transferred to an assay vessel for characterization.

Elution of Proteins

Protein can be eluted from a matrix, e.g., a matrix described herein. A sample, e.g., a biological sample, can be stabilized on a stabilization matrix capable of stabilizing a protein, e.g., as described herein, prior to elution. The elution can comprise contacting the stabilization matrix with an elution buffer. The contacting can comprise incubating (e.g., with agitation) the stabilization matrix in the elution buffer to elute the protein from the stabilization matrix. Before elution, the stabilization matrix can be contacted with a binding and or wash buffer.

The elution can be performed on at least a portion of the stabilization matrix comprising a sample, e.g., a dried biological sample. In some cases, a portion of the stabilization matrix can be separated from the rest of the stabilization matrix and used for further processing. In some cases, the portion is more than 5%, 15%, 25%, 35%, 45%, 55%, 65%, 75%, 85%, or 95% of the stabilization matrix. In some cases, the portion is less than 5%, 15%, 25%, 35%, 45%, 55%, 65%, 75%, 85%, or 95% of the stabilization matrix. The portion of a stabilization matrix can be punched out of the stabilization matrix, and proteins in the separated portions can be eluted. The portion separated for further processing can comprise 100%, or about 90%, 80%, 70%, 60%, 50%, or less of a sample that was applied to the matrix. The punches can be about 0.5, 1, 2, 3, 4, 5, 6, 7, 8, 9, 10, 15, 20, 25, 30, 35, 40, 45, 50, 55, or 60 mm in diameter. The punches can be at most 0.5, 1, 2, 3, 4, 5, 6, 7, 8, 9, 10, 15, 20, 25, 30, 35, 40, 45, 50, 55, or 60 mm in diameter. The punches can be from about 10 to about 60, from about 10 to about 60, from about 10 to about 60, from about 10 to about 30, from about 10 to about 20, from about 1 to about 10, from about 2 to about 9, from about 3 to about 8, from about 4 to about 7, from about 3 to about 6, from about 4 to about 5, from about 1 to about 4, from about 1 to about 3, from about or from about 1 to about 2 mm in diameter. In some cases, a stabilization matrix comprising protein is not separated into portions before the nucleic acid is eluted from the stabilization matrix.

Protein can be eluted from the stabilization matrix, or portion of the stabilization matrix, by contacting the stabilization matrix, or portion of the stabilization matrix, with an appropriate elution buffer. The elution buffer can comprise one or more buffering agents, one or more surfactants, one or more polyols, one or more salts, one or more blocking agents, one or more reducing agents, one or more organic solvents, one or more chelating agents, one or more salts, e.g., described herein, or any combination thereof. For example, the elution buffer can comprise one or more buffers and one or more polyols. The elution buffer can comprise one or more buffers and one or more surfactants. The elution buffer can comprise one or more buffers and one or more salts. The elution buffer can comprise one or more buffers and one or more reducing agents. The elution buffer can comprise one or more buffers, one or more surfactants, and one or more polyols. The elution buffer can comprise one or more buffers, one or more surfactants, and one or more salts. The elution buffer can comprise one or more buffers, one or more salts, and one or more reducing agents. The elution buffer can comprise one or more buffers, one or more surfactants, and one or more chelating agents. The elution buffer can comprise one or more buffers, one or more salts, one or more reducing agents, one or more chelating agents, one or more surfactants, and one or more polyols.

The one or more buffering agents can be, e.g., saline, citrate, phosphate, phosphate buffered saline (PBS), acetate, glycine, tris(hydroxymethyl)aminomethane (tris) hydrochloride, tris buffered saline (TBS), 3-[[1,3-dihydroxy-2-(hydroxymethyl)propan-2-yl]amino]propane-1-sulfonic acid (TAPS), bicine, tricine, 3-[[1,3-dihydroxy-2-(hydroxymethyl)propan-2-yl]amino]-2-hydroxypropane-1-sulfonic acid (TAPSO), 4-(2-hydroxyethyl)-1-piperazineethanesulfonic acid (HEPES), piperazine-N,N'-bis(2-ethanesulfonic acid) (PIPES), 3-(N-morpholino)propanesulfonic acid (MOPS), 2-(N-morpholino)ethanesulfonic acid (MES), 2-[[1,3-dihydroxy-2-(hydroxymethyl)propan-2-yl]amino]ethanesulfonic acid (TES), cacodylate, glycine, carbonate, or any combination thereof. The buffering agent can be present at a concentration of from about 0.1 mM to about 500, from about 0.1 mM to about 400 mM, from about 0.1 mM to about 300 mM, from about 0.1 mM to about 200 mM, from about 0.1 mM to about 100 mM, from about 0.1 mM to about 50 mM, from about 0.1 mM to about 25 mM, from about 0.1 mM to about 20 mM, from about 0.1 mM to about 15 mM, from about 0.1 mM to about 10 mM, from about 0.1 mM to about 5 mM, from about 0.1 mM to about 4 mM, from about 0.1 mM to about 3 mM, from about 0.1 mM to about 2 mM, from about 0.1 mM to about 1 mM, from about 0.1 mM to about 0.9 mM, from about 0.1 mM to about 0.8 mM, from about 0.1 mM to about 0.7 mM, from about 0.1 mM to about 0.6 mM, from about 0.1 mM to about 0.5 mM, from about 0.1 mM to about 0.4 mM, from about 0.1 mM to about 0.3 mM, or from about 0.1 mM to about 0.2 mM. The buffering agent can be present at a concentration of less than 500 mM, less than 400 mM, less than 300 mM, less than 200 mM, less than 100 mM, less than 50 mM, less than 25 mM, less than 20 mM, less than 15 mM, less than 10 mM, less than 5 mM, less than 4 mM, less than 3 mM, less than 2 mM, less than 1 mM, less than 0.9 mM, less than 0.8 mM, less than 0.7 mM, less than 0.6 mM, less than 0.5 mM, less than 0.4 mM, less than 0.3 mM, less than 0.2 mM, or less than 0.1 mM. The buffering agent can be present at about 0.1 mM, 1 mM, 10 mM, 25 mM, or 50 mM. The buffering agent can be present at at least 0.1 mM, 1 mM, 10 mM, 25 mM, or 50 mM.

A one or more surfactants can be, e.g., an anionic, cationic, nonionic or amphoteric type. The one or more surfactants can be, e.g., polyethoxylated alcohols; polyoxyethylene sorbitan; octoxynol such as Triton X 100™ (polyethylene glycol p-(1,1,3,3-tetramethylbutyl)-phenyl ether); polysorbates such as Tween™ 20 ((e.g., polysorbate 20) or Tween™ 80 (polysorbate 80); sodium dodecyl sulfate; sodium lauryl sulfate; nonylphenol ethoxylate such as Tergitol™; cyclodextrins; or any combination thereof. Each of the one or more surfactants can be present at a concentration of less than 0.001%, less than 0.005%, less than 0.01%, less than 0.015%, less than 0.02%, less than 0.025%, less than 0.03%, less than 0.035%, less than 0.04%, less than 0.045%, less than 0.05%, less than 0.055%, less than 0.06%, less than 0.065%, less than 0.07%, less than 0.075%, less than 0.08%, less than 0.085%, less than 0.09%, less than 0.095%, less than 0.1%, less than 0.15%, less than 0.2%, less than 0.25%, less than 0.3%, less than 0.35%, less than 0.4%, less than 0.45%, less than 0.5%, less than 0.55%, less than 0.6%, less than 0.65%, less than 0.7%, less than 0.75%, less than 0.8%, less than 0.85%, less than 0.9%, less than 0.95%, less than 0.1%, less than 1%, less than 2%, less than 3% or by volume relative to the total volume of the elution buffer. The one or more surfactants can be present at a concentration of about 0.01%, 0.05%, 0.1%, 0.5%, 1%, 5%, or 10%. The one or more surfactants can be present at a concentration of at least 0.01%, 0.05%, 0.1%, 0.5%, 1%, 5%, or 10%. The one or more surfactants can be present at a concentration of from about 0.01% to 1%, from about 0.05% to 1%, from about 0.1% to 1%, from about 0.15% to 1%, from about 0.2% to 1%, from about 0.25% to 1%, from about 0.3% to 1%, from about 0.35% to 1%, from about 0.4% to 1%, from about 0.45% to 1%, from about 0.5% to 1%, from about 0.55% to 1%, from about 0.6% to 1%, from about 0.65% to 1%, from about 0.7% to 1%, from about 0.75% to 1%, from about 0.8% to 1%, from about 0.85% to 1%, from about 0.9% to 1%, or from about 0.95% to 1%, The elution buffer can be an aqueous solution having a pH from about 2 to about 10, from about 2 to about 9, from about 2 to about 8, from about 2 to about 7, from about 2 to about 6, from about 2 to about 5, from about 2 to about 4, or from about 2 to about 3. The elution buffer can be an aqueous solution having a pH from about 6 to about 8, from about 6 to about 7.9, from about 6 to about 7.8, from about 6 to about 7.7, from about 6 to about 7.6, from about 6 to about 7.5, from about 6 to about 7.4, from about 6 to about 7.3, from about 6 to about 7.2, from about 6 to about 7.1, from about 6 to about 7, from about 6 to about 6.9, from about 6 to about 6.8, from about 6 to about 6.7, from about 6 to about 6.6, from about 6 to about 6.5, from about 6 to about 6.4, from about 6 to about 6.3, from about 6 to about 6.2, or from about 6 to about 6.1. The elution buffer can be an aqueous solution having a pH of at least about 3, at least about 4, at least about 5, at least about 6, at least about 7, at least about 8, at least about 9, or at least about 10. The pH can be about 6, 6.5, 7, 7.5, 8, or 8.5.

In some instances, the one or more polyols can be a glycol such as ethylene glycol or propylene glycol, or a glycol polymer such as polyethylene glycol (PEG) of various weights such as PEG300, PEG400, PEG600, PEG1000, PEG3000, and PEG6000. In some instances, the one or more polyols can be a sugar. In some cases, the sugar can be sucrose, glucose, fructose, trehalose, maltose, galactose, lactose or any combination thereof. In some instances, the one or more polyols can be a sugar alcohol. In some cases, the sugar alcohol can be glycerol, erythritol, threitol, xylitol, sorbitol and the like.

The one or more salts can be sodium chloride, sodium acetate, sodium bicarbonate, sodium bisulfate, sodium bromide, potassium chloride, potassium acetate, potassium bicarbonate, potassium bisulfate, potassium bromate, potassium bromide, or potassium carbonate. The one or more salts can be at a concentration of about 0.1 mM, 5 mM, 10 mM, 25 mM, 50 mM, 100 mM, 250 mM, 500 mM, or 750 mM. The one or more salts can be at a concentration of less than 0.1 mM, 5 mM, 10 mM, 25 mM, 50 mM, 100 mM, 250 mM, 500 mM, or 750 mM. The one or more salts can be at a concentration of at least 0.1 mM, 5 mM, 10 mM, 25 mM, 50 mM, 100 mM, 250 mM, 500 mM, 750 mM, or 1000 mM.

The one or more blocking agents can be bovine serum albumin, fetal bovine serum, and the like.

The one or more organic solvents can be, e.g., methanol, ethanol, DMSO, DMF, dioxane, tetrahydrofuran, propanol, isopropanol, butanol, t-butanol, or pentanol, acetone and the like. The elution buffer can comprise less than 0.01%, less than 0.05%, less than 0.1%, less than 0.15%, less than 0.2%, less than 0.25%, less than 0.3%, less than 0.35%, less than 0.4%, less than 0.45%, less than 0.5%, less than 0.55%, less than 0.6%, less than 0.65%, less than 0.7%, less than 0.75%, less than 0.8%, less than 0.85%, less than 0.9%, less than 0.95%, less than 1%, less than 1.5%, less than 2%, less than 2.5%, less than 3%, less than 3.5%, less than 4%, less than 4.5%, less than 5%, less than 5.5%, less than 6%, less than 6.5%, less than 7%, less than 7.5%, less than 8%, less than 8.5%, less than 9%, less than 9.5%, less than 10%, less than 11%, less than 12%, less than 13%, less than 14%, less than 15%, less than 16%, less than 17%, less than 18%, less than 19%, less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 99%, or 100% of an organic solvent by volume relative to the total volume of the solution. The concentration of the one or more organic solvents in the elution buffer can be at least 1%, 5%, 10%, 50%, 75%, or 100%. The concentration of the one or more organic solvents in the elution buffer can be about 1%, 5%, 10%, 50%, 75%, or 100%

The stabilization matrix, or portion of the stabilization matrix, can be contacted with a volume of the elution buffer of about, or less than 5 µL, less than 10 µL, less than 15 µL, less than 20 µL, less than 25 µL, less than 30 µL, less than 35 µL, less than 40 µL, less than 45 µL, less than 50 µL, less than 55 µL, less than 60 µL, less than 65 µL, less than 70 µL, less than 75 µL, less than 80 µL, less than 85 µL, less than 90 µL, less than 95 µL, less than 100 µL, less than 110 µL, less than 120 µL, less than 130 µL, less than 140 µL, less than 150 µL, less than 160 µL, less than 170 µL, less than 180 µL, less than 190 µL, less than 200 µL, less than 250 µL, less than 300 µL, less than 350 µL, less than 400 µL, less than 450 µL, less than 500 µL, less than 550 µL, less than 600 µL, less than 650 µL, less than 700 µL, less than 750 µL, less than 800 µL, less than 850 µL, less than 900 µL, less than 950 µL, less than 1,000 µL less than 1.5 mL, less than 2 mL, less than 2.5 mL, less than 3 mL, less than 3.5 mL, less than 4 mL, less than 4.5 mL, less than 5 mL, less than 5.5 mL, less than 6 mL, less than 6.5 mL, less than 7 mL, less than 7.5 mL, less than 8 mL, less than 8.5 mL, less than 9 mL, less than 9.5 mL, or less than 10 mL. The stabilization matrix, or portion of the stabilization matrix, can be contacted with about 0.1 mL, 0.2 mL, 0.5 mL, 0.7 mL, 1 mL, 2 mL, 5 mL, 7 mL, or 10 mL, or more of elution buffer. The stabilization matrix, or portion of the stabilization matrix, can be contacted with at least 0.1 mL, 0.2 mL, 0.5 mL, 0.7 mL, 1 mL, 2 mL, 5 mL, 7 mL, or 10 mL of elution buffer.

The volume of elution contacted with the stabilization matrix can be dependent on the surface area of the stabilization matrix. The amount of elution buffer can be less than 1 µL/mm$^2$, less than 2 µL/mm$^2$, less than 3 µL/mm$^2$, less than 4 µL/mm$^2$, less than 5 µL/mm$^2$, less than 6 µL/mm$^2$, less than 7 µL/mm$^2$, less than 8 µL/mm$^2$, less than 9 µL/mm$^2$, less than 10 µL/mm$^2$, less than 12 µL/mm$^2$, less than 14 µL/mm$^2$, less than 16 µL/mm$^2$, less than 18 µL/mm$^2$, less than 20 µL/mm$^2$, less than 25 µL/mm$^2$, less than 30 µL/mm$^2$, less than 35 µL/mm$^2$, less than 40 µL/mm$^2$, less than 45 µL/mm$^2$, less than 50 µL/mm$^2$, less than 55 µL/mm$^2$, less than 60 µL/mm$^2$, less than 65 µL/mm$^2$, less than 70 µL/mm$^2$, less than 75 µL/mm$^2$, less than 80 µL/mm$^2$, less than 85 µL/mm$^2$, less than 90 µL/mm$^2$, less than 95 µL/mm$^2$, less than 100 µL/mm$^2$, less than 150 µL/mm$^2$, less than 200 µL/mm$^2$, less than 250 µL/mm$^2$, less than 300 µL/mm$^2$, less than 350 µL/mm$^2$, less than 400 µL/mm$^2$, less than 450 µL/mm$^2$, less than 500 µL/mm$^2$, less than 550 µL/mm$^2$, less than 600 µL/mm$^2$, less than 650 µL/mm$^2$, less than 700 µL/mm$^2$, less than 750 µL/mm$^2$, less than 800 µL/mm$^2$, less than 850 µL/mm$^2$, less than 900 µL/mm$^2$, less than 950 µL/mm$^2$, or less than 1,000 µL/mm$^2$. In some cases, the amount of elution buffer can be from about 10 µL/mm$^2$ to about 1,000 µL/mm$^2$, from about 10 µL/mm$^2$ to about 900 µL/mm$^2$, from about 10 µL/mm$^2$ to about 800 µL/mm$^2$, from about 10 µL/mm$^2$ to about 700 µL/mm$^2$, from about 10 µL/mm$^2$ to about 600 µL/mm$^2$, from about 10 µL/mm$^2$ to about 500 µL/mm$^2$, from about 10 µL/mm$^2$ to about 400 µL/mm$^2$, from about 10 µL/mm$^2$ to about 300 µL/mm$^2$, from about 10 µL/mm$^2$ to about 200 µL/mm$^2$, from about 10 µL/mm$^2$ to about 100 µL/mm$^2$, from about 10 µL/mm$^2$ to about 90 µL/mm$^2$, from about 10 µL/mm$^2$ to about 80 µL/mm$^2$, from about 10 µL/mm$^2$ to about 70 µL/mm$^2$, from about 10 µL/mm$^2$ to about 60 µL/mm$^2$, from about 10 µL/mm$^2$ to about 50 µL/mm$^2$, from about 10 µL/mm$^2$ to about 40 µL/mm$^2$, from about 10 µL/mm$^2$ to about 30 µL/mm$^2$, or from about 10 µL/mm$^2$ to about 20 µL/mm$^2$.

The protein can be eluted from the stabilization matrix by incubating the stabilization matrix in the elution buffer in the presence or absence of agitation from an agitation source. An agitation source can be a rocker, vortexer, mixer, shaker and the like. In some cases, an agitation source can be set to a constant speed. The speed can be less than 1 rotations per minute (rpm), less than 5 rpm, less than 10 rpm, less than 15 rpm, less than 20 rpm, less than 25 rpm, less than 30 rpm, less than 35 rpm, less than 40 rpm, less than 45 rpm, less than 50 rpm, less than 55 rpm, less than 60 rpm, less than 65 rpm, less than 70 rpm, less than 75 rpm, less than 80 rpm, less than 85 rpm, less than 90 rpm, less than 95 rpm, less than 100 rpm, less than 150 rpm, less than 200 rpm, less than 250 rpm, less than 300 rpm, less than 350 rpm, less than 400 rpm, less than 450 rpm, less than 500 rpm, less than 550 rpm, less than 600 rpm, less than 650 rpm, less than 700 rpm, less than 750 rpm, less than 800 rpm, less than 850 rpm, less than 900 rpm, less than 950 rpm, less than 1,000 rpm, less than 1,500 rpm, less than 2,000 rpm, less than 2,500 rpm, less than 3,000 rpm, less than 3,500 rpm, less than 4,000 rpm, less than 4,500 rpm, less than 5,000 rpm, less than 5,500 rpm, less than 6,000 rpm, less than 6,500 rpm, less than 7,000 rpm, less than 7,500 rpm, less than 8,000 rpm, less than 8,500 rpm, less than 9,000 rpm, less than 9,500 rpm, or less than 10,000 rpm. The speed can be about 50 rpm 100 rpm, 200 rpm, 300 rpm, 400 rpm, 500 rpm, 600 rpm, 700 rpm, 800 rpm, 900 rpm, 1000 rpm, 1500 rpm, or 5000 rpm. The speed can be at least 50 rpm 100 rpm, 200 rpm, 300 rpm, 400 rpm, 500 rpm, 600 rpm, 700 rpm, 800 rpm, 900 rpm, 1000 rpm, 1500 rpm, or 5000 rpm.

The elution can be performed at a temperature of about 0° C., less than 1° C., less than 2° C., less than 3° C., less than 4° C., less than 5° C., less than 6° C., less than 7° C., less than 8° C., less than 9° C., less than 10° C., less than 11° C., less than 12° C., less than 13° C., less than 14° C., less than 15° C., less than 16° C., less than 17° C., less than 18° C., less than 19° C., less than 20° C., less than 21° C., less than 22° C., less than 23° C., less than 24° C., less than 25° C., less than 26° C., less than 27° C., less than 28° C., less than 29° C., less than 30° C., less than 31° C., less than 32° C., less than 33° C., less than 34° C., less than 35° C., less than 36° C., less than 37° C., less than 38° C., less than 39° C., less than 40° C., less than 45° C., less than 50° C., less than 55° C., less than 60° C., less than 65° C., less than 70° C., less than 75° C., less than 80° C., less than 85° C., less than 90° C., less than 95° C., or about 100° C. The elution can be performed at a temperature of from about 10° C. to about 100° C., from about 10° C. to about 95° C., from about 10° C. to about 90° C., from about 10° C. to about 85° C., from about 10° C. to about 80° C., from about 10° C. to about 75° C., from about 10° C. to about 70° C., from about 10° C. to about 65° C., from about 10° C. to about 60° C., from about 10° C. to about 55° C., from about 10° C. to about 50° C.

from about 20° C. to about 50° C., from about 20° C. to about 48° C., from about 20° C. to about 46° C., from about 20° C. to about 44° C., from about 20° C. to about 42° C., from about 20° C. to about 40° C., from about 20° C. to about 38° C., from about 20° C. to about 36° C., from about 20° C. to about 34° C., from about 20° C. to about 32° C., from about 20° C. to about 30° C., from about 20° C. to about 28° C., from about 20° C. to about 26° C., from about 20° C. to about 24° C., or from about 20° C. to about 22° C. The elution be performed at about 10° C., 20° C., 25° C., 30° C., 37° C., 50° C., or 65° C.

The elution (e.g., agitation) can be performed for less than 1, less than 5, less than 10, less than 15, less than 20, less than 25, less than 30, less than 35, less than 40, less than 45, less than 50, less than 55, or less than 60 minutes. The elution can be performed for less than 0.5, less than 1, less than 1.5, less than 2, less than 2.5, less than 3, less than 3.5, less than 4, less than 4.5, less than 5, less than 5.5, less than 6, less than 6.5, less than 7, less than 7.5, less than 8, less than 8.5, less than 9, less than 9.5, less than 10, less than 10.5, less than 11, less than 11.5, or less than 12 hours. The elution can be performed for less than 0.1 days, less than 0.2 days, less than 0.3 days, less than 0.4 days, less than 0.5 days, less than 0.6 days, less than 0.7 days, less than 0.8 days, less than 0.9 days, less than 1 days, less than 1.5 days, less than 2 days, less than 2.5 days, less than 3 days, less than 3.5 days, less than 4 days, less than 4.5 days, less than 5 days, less than 5.5 days, less than 6 days, less than 6.5 days, or less than 7 days. The elution (e.g., agitation) can be performed for about 0.25 hr, 0.5 hr, 1 hr, 2 hr, 5 hr, 10 hr, 12 hr, 18 hr, 24 hr, 3 days, or 1 week. The elution (e.g., agitation) can be performed for at least 0.25 hr, 0.5 hr, 1 hr, 2 hr, 5 hr, 10 hr, 12 hr, 18 hr, 24 hr, 3 days, or 1 week. Table 1 lists examples of protein elution buffers.

The stack can comprise the same matrix, e.g., each matrix in the stack can have the same composition. The stack can comprise matrices with different compositions, e.g., a matrix configured for stabilizing a nucleic acid can be on top of a matrix configured to stabilize protein, or vice versa. The types of matrices in the stack an alternate; e.g., a matrix configured to stabilize a protein, a matrix configured to stabilize a nucleic acid, followed by a matrix configured to stabilize a protein, etc. The volume applied to a top matrix can pass through at least 2, 3, 4, 5, 6, 7, 8, 9, or 10 layers of matrices. Using multiple matrices can increase yield of recovery of a desired biomolecule, e.g., nucleic acid or polypeptide.

A sample can pass through a plurality of matrices, but the matrices do not contact each other. For example, a sample can be applied to a matrix configured to stabilize a nucleic acid, the nucleic acid can be eluted from the matrix configured to stabilize the nucleic acid and be applied to a matrix configured to stabilize a protein. The matrix configured to stabilize the protein can be used, e.g., to remove contaminates, e.g., protein contaminates from the nucleic acid. A sample can be applied to a matrix configured to stabilize a protein, and the protein can be eluted from the matrix configured to stabilize the protein and be applied to a matrix configured to stabilize a nucleic acid. The matrix configured to stabilize the nucleic acid can be used, e.g., to remove contaminates, e.g., nucleic acid contaminates, from the protein.

TABLE 1

Examples of protein elution buffers

| | | | | | |
|---|---|---|---|---|---|
| Buffer 1 | TBS | | 0.1% Triton-X 100 | 10 mM DTT | 0.5 mM EDTA |
| Buffer 2 | TBS | | 0.1% Triton-X 100 | | |
| Buffer 3 | TBS | | | | 0.5 mM EDTA |
| Buffer 4 | TBS | | | 10 mM DTT | |
| Buffer 5 | 25 mM Tris pH 7.0 | 100 mM KCl | 0.1% Triton-X 100 | | |
| Buffer 6 | 25 mM Tris pH 7.5 | 50 mM NaCl | | 10 mM DTT | 0.5 mM EDTA |
| Buffer 7 | 25 mM Tris pH 7.6 | | 0.1% Triton-X 100 | | |
| Buffer 8 | 25 mM Tris pH 8.0 | | | 10 mM DTT | |
| Buffer 9 | 25 mM HEPES | 100 mM KCl | 0.05% Tween 20 | | |
| Buffer 10 | 25 mM HEPES | 50 mM NaCl | | | |
| Buffer 11 | 10 mM HEPES | | 0.1% Tween 80 | | |
| Buffer 12 | 10 mM HEPES | | | | |
| Buffer 13 | PBS | | 0.05% Tween 20 | | |
| Buffer 14 | PBS | | | 10 mM DTT | |
| Buffer 15 | PBS | | | | 0.5 mM EDTA |
| Buffer 16 | PBS | | 0.1% Tween 80 | | |
| Buffer 17 | 50 mM Tris pH 7.5 | 25 mM KCl | 0.05% Tween 20 | | |
| Buffer 18 | 50 mM Tris pH 7.0 | 25 mM KCl | 0.1% Tween 80 | | |
| Buffer 19 | 50 mM Tris pH 8.0 | 100 mM NaCl | | | 0.5 mM EDTA |
| Buffer 20 | 50 mM Tris pH 8.5 | 150 mM NaCl | | | |

The eluted protein can be transferred to a container for storage or further processing, or can be transferred to an assay vessel for characterization.

Uses of Matrices

A sample can be applied to one matrix (e.g., one layer). A sample can be applied to a top matrix, and at least a part of the sample can contact a second matrix, e.g., a second matrix below the top matrix. Matrices can be stacked, e.g., with about, or at least 2, 3, 4, 5, 6, 7, 8, 9, 10, 20, 50, or 100 layers.

EXAMPLES

Example 1

Methods and Kits for Tagged Sample Collection and Preparation

Sample acquisition and stabilization components are deployed to end users. The sample stabilization components are specifically configured for a designated set of diagnostic tests; in particular they are configured for specific target component. For example, DNA, RNA and protein target components each have different substrate composition and identifying color. Tests configured for an RNA target component have a red stabilization matrix, tests configured for DNA have a green stabilization matrix, and tests configured for a protein target component have a blue stabilization matrix. Furthermore, each deployed system has a unique barcode; this barcode is used to sort and separate the samples by type (RNA/DNA/Protein) for batching of the samples, and for connecting the sample results with the identifying information corresponding to the donor from which the sample came. The sample stabilization components have multiple barcode labels, one that remains permanently fixed to the sample stabilization component and several removable adhesive labels for easy processing. The labels display the unique barcode associated with the deployed system. After the sample acquisition and stabilization system has been used to acquire the sample, the system is returned to a facility where it is collected. The fixed barcode is used to mechanically separate the received systems by substrate type. For example, all the sample stabilization components with red stabilization matrix are collected together and assembled into batches of 96. Assays are performed based on the sample color tag. A batch of 96 red samples are collected together, two labels from each of the samples are transferred to two sets 96 RNAse-free tubes each assembled in order based on the order they were scanned in. Each rack of 96 labeled sample tubes are set-up and organized identically. The sample stabilization components for each of the 96 samples is opened in the order they were scanned in and the red colored substrate is removed and placed, like a filter, onto a rim disposed within the RNAse-free sample tubes with the corresponding sample barcode label. This is done until the substrate for each of the 96 samples is in the correctly labeled and corresponding 96 sample tubes. A "red kit" designed for the target components from the red substrate is opened, revealing red-topped containers of RNase-free PCR buffers, reagents and other molecular components, the bottles each have step numbers on them as well, so that they can be easily and quickly used to perform the different treatment steps for the red samples. An aliquot of the "step 1 red reagent" is added to the top of the red colored substrate in each of the 96 labeled tubes, the tubes are closed and the reagents are left for a few minutes to soak into the substrate. After the reagents and buffers have soaked in, the sample is centrifuged—driving the contents of the substrate into the liquid solution that forms at the bottom of the sample tube. Another aliquot of the "step 1 red reagent" is added again to the top of the substrate and the centrifugation is repeated. The tubes are opened and the solid substrate is removed from each sample; then an aliquot of "step 2 red reagent", comprising a buffered solution containing DNA molecules that are partially double-stranded with a single stranded region that is complementary to target component RNA, is added to the liquid solution. The tubes are closed and placed in a PCR machine at a temperature that encourages Brownian motion without inducing denaturation of the double stranded DNA molecule; at this temperature RNA from the substrate hybridizes with the single stranded region of the DNA molecule. The DNA molecule has a promoter for RNA polymerase within the double stranded region and the 3' overhang of the single stranded region has a string of thymidine residues. The poly(A) tails of the 3' end of messenger RNA (mRNA) from the red substrate hybridize with the thymine residue overhangs of the DNA molecule. The tubes are then opened and an aliquot of the "step 3 red reagent" comprising ligase enzymes and buffer, is added to the tube. The samples are heated and ligation occurs between the mRNA and the double stranded DNA molecule, forming a double stranded RNA-DNA molecule with the entire mRNA incorporated as one strand of the molecule. The tube is opened and an aliquot of "step 4 red reagent" comprising RNA polymerase is added to each of the 96 tubes, the tubes are closed and 32 PCR cycles of repeated denaturation and annealing are run on the sample to amplify the RNA templates and produce a library of anti-sense cRNA. An aliquot of the amplified cRNA PCR product is transferred to each of the corresponding 96 empty labeled sample tubes, and an aliquot of "step 1 red reagent" is added to the second rack of 96 empty labeled tubes. Steps 2-4 are repeated resulting in ligation and polymerization, this time the resulting in sense strands of the mRNA. These sense strands are then sequenced using standard sequencing protocols, the results are analyzed using standard gene expression profile methods and the barcode number is used as an identifier to determine the donor associated with the given results.

Other kits for performing similar batches of analysis also available; a green kit works for green substrate components which selectively stabilize DNA and blue kits work for blue substrate components which selectively stabilize proteins. Different methods are used to treat samples from each of these different substrates.

Example 2

Kit with Lancet and Tourniquet with Sample Separation Component

A kit is deployed to an end user or donor. The kit comprises a crystalline-activated pouch for warming hands, a lancet, a tourniquet, alcohol pads, gauze, pressure activated lancet, a self-filling capillary and a sample stabilization component with integrated sample separation unit and sample stabilization matrix. The end user warms donor hands to encourage stimulation of blood flow prior to lancing; this is accomplished by activating a crystalline-activated hand-warmer pouch and holding it between digits of the hand. The donor's hands are relaxed and positioned below the heart and muscles, while the donor sits comfortably in a chair with hand and arms loosely positioned on the arm of the chair. A tourniquet is placed on the donor's non-dominant hand and a site is selected on the donor's middle finger. A rubber band tourniquet is wrapped around the last digit of the finger and then twisted to continue to loop around the finger several times creating a tourniquet. A loop is left available for easy removal. Pressure builds at the fingertip and the fingertip appear slightly red and engorged. Sterilization of the sample site is done; first a side of the fingertip is chosen and then an alcohol pad is swiped past the area before the area is dried with a piece of sterile gauze. The donor holds and pulls on the free loop of the tourniquet during lancing. Lancing process can depend on the type and source of lancet provided. The protective cap of the lancet is removed and the lancet is placed toward the side of the sterilized finger. The lancet is placed to avoid the center of the fingertip, which is calloused and contains a higher density of nerve endings. The lancet is pressed down until the spring in the lancet is engaged and a clicking noise is heard indicating that the skin has been pierced. The first evidence of blood is immediately removed after lancing, and mild but constant pressure is applied to the finger A self-filling capillary is held horizontal to the incision site and touched against the forming blood droplet using the self-filling capillary (e.g. Microsafe®, Safe-Tec Clinical Products, LLC, Ivyland Pa.), the capillary self-fill to a black line printed on the plastic shaft and then self-stops. A plastic bulb is present, and it is not depressed during the filling step. When the collected blood reaches the black line and stops filling, pressure is be withdrawn from the fingertip, and the free loop of the rubber band is released to reduce the pressure of the finger tourniquet. Blood is dispensed to the sample stabilization component; the sample stabilization component is placed on a flat surface, and the blood on the outside of the capillary is wiped with clean with sterile gauze. The filled capillary is held upright over the bottom of the sample stabilization component and the collected sample is being dispensed slowly and evenly pressing on a plastic bulb of the filled capillary. The capillary is fixed in place over the bottom of the sample stabilization component while dispensing. The capillary is discarded when all blood is dispensed onto the sample stabilization component. Post-procedure, the blood sampling component is left undisturbed while the finger tourniquet is completely removed and the incision site is cleaned. Pressure is applied to the incision using sterile gauze to stop bleeding and the hand is raised above the heart to assist in clotting. The sample stabilization component is left undisturbed for approximately 5-10 minutes post-procedure and observed to determine if the blood drop is still raised on the filter and if filter still appears "wet." In this case a separation component is used, so the raised "wet" droplet of blood is observed, and then straw-color plasma starts to appear on the top of the sample separation component. The appearance of sample separation is used to indicate that the sample can be placed back into a storage container. The blood sampling component is labeled using a barcode label, and left at room temperature. The storage container is sealed and deposited in the mail.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for collecting a bio-sample from a subject, the method comprising
    obtaining an integrated sample acquisition and sample stabilization device comprising: (i) a sample acquisition component, wherein the sample acquisition component comprises piercing elements; and (ii) more than one paper stabilization matrix, wherein the more than one paper stabilization matrices are stacked and do not contact each other; wherein the more than one paper stabilization matrices are separated by one or more solid supports wherein the one or more solid supports do not comprise filters;
    applying the device to a skin of the subject;
    actuating the sample acquisition component causing the piercing elements to puncture the skin of the subject;
    withdrawing the piercing elements under vacuum, causing the bio-sample to enter an opening in the sample acquisition component; and
    moving the bio-sample from the opening in the sample acquisition component through a channel onto the more than one paper stabilization matrices that are stacked and do not contact each other, wherein the bio-sample is collected on the more than one paper stabilization matrices, wherein during the moving, the more than one paper stabilization matrices are stacked and do not contact each other,
    wherein the moving the bio-sample from the opening in the sample acquisition component through the channel onto the more than one paper stabilization matrices that are stacked and do not contact each other occurs by vacuum.

2. The method of claim 1, wherein the moving the bio-sample comprises moving more than 100 µl of the bio-sample.

3. The method of claim 2, wherein the bio-sample comprises a volume of under 500 µL.

4. The method of claim 1, wherein the more than one paper stabilization matrices are porous matrices comprising cellulose, cellulose acetate, glass fiber, or a combination thereof.

5. The method of claim 1, further comprising removing from the integrated sample acquisition and sample stabilization device the more than one paper stabilization matrices comprising the collected bio-sample.

6. The method of claim 1, wherein the bio-sample is blood.

7. The method of claim 6, further comprising inducing blood flow in the subject prior to piercing the subject with the piercing elements.

8. The method of claim 1, wherein each matrix of the more than one paper stabilization matrices comprises a same composition.

9. The method of claim 1, wherein the channel is one channel.

10. The method of claim 1, wherein the more than one paper stabilization matrices are two paper stabilization matrices.

11. The method of claim 1, wherein one or more stabilizing reagents are disposed on or integrated with the more than one paper stabilization matrices, and the more than one paper stabilization matrices are in a substantially dry state of less than 10% by weight hydration.

12. The method of claim 1, wherein the more than one paper stabilization matrices are configured to substantially stabilize RNA for at least 11 days at 37 degrees Celsius.

13. The method of claim 1, further comprising removing from the integrated sample acquisition and sample stabilization device the more than one paper stabilization matrices comprising the collected bio-sample.

14. The method of claim 1, further comprising performing an assay on the collected bio-sample.

15. The method of claim 1, wherein the more than one paper stabilization matrices comprising the collected bio-sample are stored for at least one week.

16. The method of claim 1, wherein the more than one paper stabilization matrices are substantially dry with a water content of less than 2%.

17. The method of claim 1, further comprising eluting the collected bio-sample from the more than one paper stabilization matrices.

18. The method of claim 1, wherein moving the bio-sample from an opening in the sample acquisition component through the channel onto the more than one paper stabilization matrices also occurs by spontaneous capillary flow, wicking through absorbent materials, or a combination thereof.

19. The method of claim 1, further comprising inducing blood flow in the subject prior to piercing the subject with the piercing elements.

20. The method of claim 1, wherein the piercing elements are connected to a spring.

* * * * *